United States Patent
Neeper et al.

(10) Patent No.: US 7,211,569 B2
(45) Date of Patent: *May 1, 2007

(54) SYNTHETIC HUMAN PAPILLOMA VIRUS GENES

(75) Inventors: Michael P Neeper, Collegeville, PA (US); William L. McClements, Doylestown, PA (US); Kathrin U. Jansen, Doylestown, PA (US); Loren D. Schultz, Harleysville, PA (US); Ling Chen, Blue Bell, PA (US); Xin-Min Wang, Schwenksville, PA (US)

(73) Assignee: Merck & Co., Inc., Rahway, NJ (US)

( * ) Notice: Subject to any disclaimer, the term of this patent is extended or adjusted under 35 U.S.C. 154(b) by 390 days.

This patent is subject to a terminal disclaimer.

(21) Appl. No.: 10/728,131

(22) Filed: Dec. 4, 2003

(65) Prior Publication Data

US 2005/0075303 A1    Apr. 7, 2005

Related U.S. Application Data

(63) Continuation of application No. 09/642,405, filed on Aug. 21, 2000, now Pat. No. 7,001,995.

(60) Provisional application No. 60/210,143, filed on Jun. 7, 2000, now abandoned, provisional application No. 60/150,728, filed on Aug. 25, 1999, now abandoned.

(51) Int. Cl.
  *A61K 48/00*  (2006.01)
  *C07H 21/04*  (2006.01)

(52) U.S. Cl. .................. 514/44; 435/69.1; 435/320.1; 536/23.1; 424/93.21

(58) Field of Classification Search .............. None
See application file for complete search history.

(56) References Cited

U.S. PATENT DOCUMENTS

| | | | |
|---|---|---|---|
| 5,679,509 | A | 10/1997 | Wheeler et al. |
| 5,820,870 | A | 10/1998 | Joyce et al. |
| 6,019,978 | A | 2/2000 | Ertl et al. |
| 6,123,948 | A | 9/2000 | Whittle et al. |
| 6,159,729 | A | 12/2000 | Hofmann et al. |
| 7,001,995 | B1 * | 2/2006 | Neeper et al. ............ 435/69.1 |

FOREIGN PATENT DOCUMENTS

WO    WO 96 00583    1/1996
WO    WO 96 39178    12/1996

OTHER PUBLICATIONS

Zhou Jian, et al.—Journal of Virology, vol. 73, No. 6, pp. 4972-4982, 1999.
Afghan, R. K., et al.—Immunology, vol. 95, No. Suppl. 1, p. 106, 1998.
Kotecha, M. T., et al.—Immunology, vol. 95, No. Suppl. 1P. 107, 1998.
Xu, Jianqing, et al.—Zhonghua Weishengwuxue He Mainyixue Zazhi, vol. 19, No. 3, 1999.
Smahel Michal, et al.—Oncology Reports, vol. 6, No. 1, pp. 211-215, 1999.
Nimako Mercy, et al.—Cancer Research, vol. 57, No. 21, pp. 4855-4861, 1997.
Borysiewicz, L. K., et al.—Lancet, vol. 347, No. 9014, pp. 1523-1527, 1996.
Toes Rene, E. M., et al.—Proceedings of the National Academy of Sciences of the United States, vol. 94, No. 26, pp. 14660-14665, 1997.
Hi Z, et al.—Virology, vol. 270, No. 1, pp. 146-161, 2000.
Chen Chien-Hung, et al.—Vaccine, vol. 18, No. 19, pp. 2015-2022, 2000.
Donnelly, et al.—Protection Aganist Papillomavirus . . . , pp. 314-320, 1996.
Bodey, et al.—Failure of Cancer Vaccines, pp. 2665-2676, 2000.
McCluskie, et al.—Route and Method of Delivery of DNA, 1999.
Orkin, et al.—Report and Reommendations of the Panel, pp. 1-41, 1995.
Rudinger—Characteristics of the Amino Acids, pp. 1-8, 1976.
Bowie, et al.—Deciphering the Message in Protein Sequences, Vo.. 247, 1990.
Chemical Compound (Encyclopaedia Britannica Online), 2001.
Moingeon, et al.—Challenges and Issues in New Vaccine, pp. 173-175, vol. 23, No. 4, 2002.
Bubenik, J. Int. J. Onocol., 2002;20:207.
Nakano et al.- J. Virol, vol. 71; pp. 101-109, 1997.
vol. No. 5, 1998 Biochemistry and Molecular Biology International, pp. 1005-1009.

* cited by examiner

*Primary Examiner*—Q. Janice Li
(74) *Attorney, Agent, or Firm*—Alysia A. Finnegan; Joanne M. Giesser

(57) ABSTRACT

Synthetic DNA molecules encoding papillomavirus proteins are provided. The codons of the synthetic molecules are codons preferred by the projected host cell. The synthetic molecules may be used as a polynucleotide vaccine which provides effective immunoprophylaxis against papillomavirus infection through stimulation of neutralizing antibody and cell-mediated immunity.

4 Claims, 30 Drawing Sheets

SEQ.ID.NO.:1 Sequence of the Codon-Optimized HPV16L1

ATGAGCCTGTGGCTGCCCAGCGAGGCCACCGTGTACCTGCCTCCCGTGCCCGTGAGCAAG
GTGGTGAGCACCGACGAGTACGTGGCCCGCACCAACATCTACTACCACGCCGGCACCAGC
CGCCTGCTGGCCGTGGGCCACCCCTACTTCCCCATCAAGAAGCCCAACAACAACAAGATC
CTGGTGCCCAAGGTGAGCGGCCTGCAGTACCGCGTGTTCCGCATCCACCTGCCCGACCCC
AACAAGTTCGGCTTCCCCGACACAAGCTTCTACAACCCCGACACCCAGCGCCTGGTGTGG
GCCTGCGTGGGCGTGGAGGTGGGCCGCGGCCAGCCCCTGGGCGTGGGCATCAGCGGCCAC
CCCCTGCTGAACAAGCTGGACGACACCGAGAACGCCAGCGCCTACGCCGCCAACGCCGGC
GTGGACAACCGCGAGTGCATCAGCATGGACTACAAGCAGACCCAGCTGTGCCTGATCGGC
TGCAAGCCTCCCATCGGCGAGCACTGGGGCAAGGGCAGCCCCTGCACCAACGTGGCCGTG
AACCCCGGCGACTGCCCTCCCCTGGAGCTGATCAACACCGTGATCCAGGACGGCGACATG
GTGGACACCGGCTTCGGCGCCATGGACTTCACCACCCTGCAGGCCAACAAGAGCGAGGTG
CCCCTGGACATCTGCACCAGCATCTGCAAGTACCCCGACTACATCAAGATGGTGAGCGAG
CCCTACGGCGACAGCCTGTTCTTCTACCTGCGCCGCGAGCAGATGTTCGTGCGCCACCTG
TTCAACCGCGCCGGCGCCGTGGGCGAGAACGTGCCCGACGACCTGTACATCAAGGGCAGC
GGCAGCACCGCCAACCTGGCCAGCAGCAACTACTTCCCCACTCCCAGCGGCAGCATGGTG
ACCAGCGACGCCCAAATCTTCAACAAGCCCTACTGGCTGCAGCGCGCCCAGGGCCACAAC
AACGGCATCTGCTGGGGCAACCAGCTGTTCGTGACCGTGGTGGACACCACCCGCAGCACC
AACATGAGCCTGTGCGCCGCCATCAGCACCAGCGAGACCACCTACAAGAACACCAACTTC
AAGGAGTACCTGCGCCACGGCGAGGAGTACGACCTGCAGTTCATCTTCCAGCTGTGCAAG
ATCACCCTGACCGCCGACGTGATGACCTACATCCACAGCATGAACAGCACCATCCTGGAG
GACTGGAACTTCGGCCTGCAGCCCCCTCCCGGCGGTACCCTGGAGGACACCTACCGCTTC
GTGACCAGCCAGGCCATCGCCTGCCAGAAGCACACCCCTCCCGCTCCCAAGGAGGATCCC
CTGAAGAAGTACACCTTCTGGGAGGTGAACCTGAAGGAGAAGTTCAGCGCCGACCTGGAC
CAGTTCCCCCTGGGCCGCAAGTTCCTGCTGCAGGCCGGCCTGAAGGCCAAGCCCAAGTTC
ACCCTGGGCAAGCGCAAGGCCACCCCCACCACCAGCAGCACCAGCACCACCGCCAAGCGC
AAGAAGCGCAAGCTGTAA

FIG.1

SEQ.ID.NO.:2 Codon-Optimized HPV16 E1-G482D,W439R Mutant:

ATGGCCGACCCCGCCGGCACCAACGGCGAGGAGGGCACCGGCTGCAACGGCTGGTTCTAC
GTGGAGGCCGTGGTGGAGAAGAAGACCGGCGACGCCATCAGCGACGACGAGAACGAGAAC
GACAGCGACACCGGCGAGGACCTGGTGGACTTCATCGTGAACGACAACGACTACCTGACC
CAGGCCGAGACCGAGACCGCCCACGCCCTGTTCACCGCCCAGGAGGCCAAGCAGCACCGC
GACGCCGTGCAGGTGCTGAAGCGCAAGTACCTGGGCAGCCCCCTGAGCGACATCAGCGGC
TGCGTCGACAACAACATCAGCCCCCGCCTGAAGGCCATCTGCATCGAGAAGCAGAGCCGC
GCCGCCAAGCGCCGCCTGTTCGAGAGCGAGGACAGCGGCTACGGCAACACCGAGGTGGAG
ACCCAGCAGATGCTGCAGGTGGAGGGCCGCCACGAGACCGAGACCCCCTGCAGCCAGTAC
AGCGGCGGCAGCGGCGGCGGCTGCAGCCAGTACAGCAGCGGCAGCGGCGGCGAGGGCGTG
AGCGAGCGCCACACCATCTGCCAGACCCCTCTGACCAACATCCTGAACGTGCTGAAGACC
AGCAACGCCAAGGCCGCCATGCTGGCCAAGTTCAAGGAGCTGTACGGCGTGAGCTTCAGC
GAGCTGGTGCGCCCCTTCAAGAGCAACAAGAGCACCTGCTGCGACTGGTGCATCGCCGCC
TTCGGCCTGACCCCCAGCATCGCCGACAGCATCAAGACCCTGCTGCAGCAGTACTGCCTG
TACCTGCACATCCAGAGCCTGGCCTGCAGCTGGGGCATGGTGGTGCTGCTGCTGGTGCGC
TACAAGTGCGGCAAGAACCGCGAGACCATCGAGAAGCTGCTGAGCAAGCTGCTGTGCGTG
AGCCCCATGTGCATGATGATCGAGCCTCCCAAGCTTCGCAGCACCGCCGCCGCCCTGTAC
TGGTACAAGACCGGCATCAGCAACATCAGCGAGGTGTACGGCGACACCCCCGAGTGGATC
CAGCGCCAGACCGTGCTGCAGCACAGCTTCAACGACTGCACCTTCGAGCTGAGCCAGATG
GTGCAGTGGGCCTACGACAACGACATCGTGGACGACAGCGAGATCGCCTACAAGTACGCC
CAGCTGGCCGACACCAACAGCAACGCCAGCGCCTTCCTGAAGAGCAACAGCCAGGCCAAG
ATCGTGAAGGACTGCGCCACCATGTGCCGCCACTACAAGCGCGCCGAGAAGAAGCAGATG
AGCATGAGCCAGTGGATCAAGTACCGCTGCGACCGCGTGGACGACGGCGGCGACCGCAAG
CAGATCGTGATGTTCCTGCGCTACCAGGGCGTGGAATTCATGAGCTTCCTGACCGCCCTG
AAGCGCTTCCTGCAGGGCATCCCCAAGAAGAACTGCATCCTGCTGTACGGCGCCGCCAAC
ACCGACAAGAGCCTGTTCGGCATGAGCCTGATGAAGTTCCTGCAGGGCAGCGTGATCTGC
TTCGTGAACAGCAAGAGCCACTTCTGGCTGCAGCCCCTGGCCGACGCCAAGATCGGCATG
CTGGACGACGCCACCGTGCCCTGCTGGAACTACATCGACGACAACCTGCGCAACGCCCTG
GACGGCAACCTGGTGAGCATGGACGTGAAGCACCGCCCCCTGGTGCAGCTGAAGTGCCCT
CCCCTGCTGATCACCAGCAACATCAACGCCGGCACCGACAGCCGCTGGCCCTACCTGCAC
AACCGCCTGGTGGTGTTCACCTTCCCCAACGAGTTCCCCTTCGACGAGAACGGTAACCCC
GTGTACGAGCTGAACGACAAGAACTGGAAGAGCTTCTTCAGCCGCACCTGGAGCCGCCTG
AGCCTGCACGAGGACGAGGACAAGGAGAACGACGGCGACAGCCTGCCCACCTTCAAGTGC
GTGAGCGGCCAGAACACCAACACCCTGTAA

FIG.2

SEQ.ID.NO.:3 Sequence of the Codon-Optimized HPV16E2-E39A,I73A Mutant:

ATGGAGACCCTGTGCCAGCGCCTGAACGTGTGCCAGGACAAGATCCTGACCCACTACGAG
AACGACAGCACCGACCTGCGCGACCACATCGACTACTGGAAGCACATGCGCCTGGCCTGC
GCCATCTACTACAAGGCCCGCGAGATGGGCTTCAAGCACATCAACCACCAGGTGGTGCCC
ACCCTGGCCGTGAGCAAGAACAAGGCCCTGCAGGCCGCCGAGCTGCAGCTGACCCTGGAG
ACCATCTACAACAGCCAGTACAGCAACGAGAAGTGGACCCTGCAGGACGTGAGCCTGGAG
GTGTACCTGACCGCCCCCACCGGCTGCATCAAGAAGCACGGCTACACCGTGGAGGTGCAG
TTCGACGGCGACATCTGCAACACCATGCACTACACCAACTGGACCCACATCTACATCTGC
GAGGAGGCCAGCGTGACCGTGGTGGAGGGCCAGGTGGACTACTACGGCCTGTACTACGTG
CACGAGGGCATCCGCACCTACTTCGTGCAGTTCAAGGACGACGCCGAGAAGTACAGCAAG
AACAAGGTGTGGGAGGTGCACGCCGGCGGCCAGGTGATCCTGTGCCCCACCAGCGTGTTC
AGCAGCAACGAGGTGAGCAGCCCCGAGACCATCCGCCAGCACCTGGCCAACCACAGCGCC
GCCACCCACACCAAGGCCGTGGCCCTGGGCACCGAGGAGACCCAGACCACCATCCAGCGC
CCCCGCAGCGAGCCCGACACCGGCAACCCCTGCCACACCACCAAGCTGCTGCACCGCGAC
AGCGTGGACAGCGCCCCCATCCTGACCGCCTTCAACAGCAGCCACAAGGGCCGCATCAAC
TGCAACAGCAACACCACCCCCATCGTGCACCTGAAGGGCGACGCCAACACCCTGAAGTGC
CTGCGCTACCGCTTCAAGAAGCACTGCAAGCTGTACACCGCCGTGAGCAGCACCTGGCAC
TGGACCGGCCACAACGTGAAGCACAAGAGCGCCATCGTGACCCTGACCTACGACAGCGAG
TGGCAGCGCGACCAGTTCCTGAGCCAGGTGAAGATCCCCAAGACCATCACCGTGAGCACC
GGCTTCATGAGCATCTAA

FIG. 3

SEQ.ID.NO.:4 Codon-Optimized HPV16E7-C24G,E26 Mutant:

ATGCACGGCGACACCCCCACCCTGCACGAGTACATGCTGGACCTGCAGCCCGAGACCACC
GACCTGTACGGCTACGGCCAGCTGAACGACAGCAGCGAGGAGGAGGACGAGATCGACGGC
CCCGCCGGCCAGGCCGAGCCCGACCGCGCCCACTACAACATCGTGACCTTCTGCTGCAAG
TGCGACAGCACCCTGCGCCTGTGCGTGCAGAGCACCCACGTGGACATCCGCACCCTGGAG
GACCTGCTGATGGGCACCCTGGGCATCGTGTGCCCCATCTGCAGCCAGAAGCCCTAA

FIG. 4

SEQ.ID.NO.:5 Codon-Optimized HPV6a E7 Gene:

ATGCACGGCCGCCACGTGACCCTGAAGGACATCGTGCTGGACCTGCAGCCTCCCGACCCC
GTGGGCCTGCACTGCTACGAGCAGCTGGTGGACAGCAGCGAGGACGAGGTGGACGAGGTG
GACGGCCAGGACAGCCAGCCCCTGAAGCAGCACTTCCAGATCGTGACCTGCTGCTGCGGC
TGCGACAGCAACGTGCGCCTGGTGGTGCAGTGCACCGAGACCGACATCCGCGAGGTGCAG
CAGCTCCTGCTGGGTACCCTGAACATCGTGTGCCCCATCTGCGCTCCCAAGACCTAA

FIG.5

SEQ.ID.NO.:6 Codon-Optimized HPV18 E7 Gene:

ATGCACGGCCCCAAGGCCACCCTGCAGGACATCGTGCTGCACCTGGAGCCCCAGAACGAG
ATCCCCGTGGACCTGCTGTGCCACGAGCAGCTGAGCGACAGCGAGGAGGAGAACGACGAG
ATCGACGGCGTGAACCACCAGCACCTGCCCGCTCGCAGGGCCGAGCCCCAGCGCCACACC
ATGCTGTGCATGTGCTGCAAGTGCGAGGCCCGCATCGAGCTGGTGGTGGAGAGCAGCGCT
GACGACCTGCGCGCCTTCCAGCAGCTGTTCCTGAACACCCTGAGCTTCGTGTGCCCCTGG
TGCGCCAGCCAGCAGTAA

FIG.6

SEQ.ID.NO.:7 Codon-Optimized HPV6a E2 Gene:

ATGGAGGCCATCGCCAAGCGCCTGGACGCCTGCCAGGAGCAGCTGCTGGAGCTGTACGAG
GAGAACAGCACCGACCTGCACAAGCACGTGCTGCACTGGAAGTGCATGCGCCACGAGAGC
GTGCTGCTGTACAAGGCCAAGCAGATGGGCCTGAGCCACATCGGCATGCAGGTGGTGCCT
CCTCTGAAGGTGAGCGAGGCCAAGGGCCACAACGCCATCGAGATGCAGATGCACCTCGAG
AGCCTGCTGCGCACCGAGTACAGCATGGAGCCCTGGACCCTGCAGGAGACCAGCTACGAG
ATGTGGCAGACCCCTCCCAAGCGCTGCTTCAAGAAGCGCGGCAAGACCGTGGAGGTGAAG
TTCGACGGCTGCGCCAACAACACCATGGACTACGTGGTGTGGACCGACGTGTACGTGCAG
GACAACGACACCTGGGTGAAGGTGCACAGCATGGTGGACGCCAAGGGCATCTACTACACC
TGTGGCCAGTTCAAGACCTACTACGTGAACTTCGTGAAGGAGGCCGAGAAGTACGGCAGC
ACCAAGCACTGGGAGGTGTGCTACGGCAGCACCGTGATCTGCAGCCCCGCTAGCGTGAGC
AGCACCACCCAGGAGGTGAGCATCCCCGAGAGCACCACCTACACTCCCGCCCAGACCAGC
ACCCTGGTGAGCAGCAGCACCAAGGAGGACGCCGTGCAGACCCCTCCTCGCAAGCGCGCC
CGCGGCGTGCAGCAGAGCCCCTGCAACGCCCTGTGCGTGGCCCACATCGGCCCCGTGGAT
AGCGGCAACCACAACCTGATCACCAACAACCACGACCAGCACCAGCGCCGCAACAACAGC
AACAGCAGCGCCACTCCCATCGTGCAGTTCCAGGGCGAGAGCAACTGCCTGAAGTGCTTC
CGCTACCGCCTGAACGATCGCCACCGCCACCTGTTCGACCTGATCAGCAGCACCTGGCAC
TGGGCCAGCAGCAAGGCTCCCCACAAGCACGCCATCGTGACCGTGACCTACGACAGCGAG
GAGCAGCGCCAGCAGTTCCTGGACGTGGTGAAGATCCCTCCCACCATCAGCCACAAGCTG
GGCTTCATGAGCCTGCACCTGCTGTAA

FIG.7

SEQ.ID.NO.:8 Codon-Optimized HPV18 E2 Gene:

ATGCAGACTCCCAAGGAGACCCTGAGCGAGCGCCTGAGCGCCCTGCAGGACAAGATCATC
GACCACTACGAGAACGACAGCAAGGACATCGACAGCCAGATCCAGTACTGGCAGCTGATC
CGCTGGGAGAACGCCATCTTCTTCGCCGCTCGCGAGCACGGGATCCAGACCCTGAACCAC
CAGGTGGTGCCCGCCTACAACATCAGCAAGAGCAAGGCCCACAAGGCCATCGAGCTGCAG
ATGGCCCTGCAGGGCCTGGCCCAGAGCGCCTACAAGACCGAGGACTGGACCCTGCAGGAC
ACCTGCGAGGAGCTGTGGAACACCGAGCCCACCCACTGCTTCAAGAAGGGAGGCCAGACC
GTGCAGGTGTACTTCGACGGCAACAAGGACAACTGCATGAACTACGTGGCCTGGGACAGC
GTGTACTACATGACCGACGCCGGCACCTGGGACAAGACCGCCACCTGCGTGAGCCACCGC
GGCCTGTACTACGTGAAGGAGGGCTACAACACCTTCTACATCGAGTTCAAGAGCGAGTGC
GAGAAGTACGGCAACACCGGCACCTGGGAGGTGCACTTCGGCAACAACGTGATCGACTGC
AACGACAGCATGTGCAGCACCAGCGACGACACCGTGAGCGCCACCCAGCTGGTGAAGCAG
CTGCAGCACACTCCCAGCCCCTACAGCAGCACCGTGAGCGTGGGCACCGCCAAGACCTAC
GGCCAGACCAGCGCCGCCACTCGCCCTGGCCACTGCGGCCTGGCCGAGAAGCAGCACTGC
GGGCCCGTGAACCCTCTGCTGGGCGCCGCCACCGCCACCGGCAACAACAAGCGCCGCAAG
CTGTGCAGCGGCAACACCACTCCCATCATCCACCTGAAGGGCGACCGCAACAGCCTGAAG
TGCCTGCGGTACCGCCTGCGCAAGCACAGCGACCACTACCGCGACATCAGCAGCACCTGG
CACTGGACCGGCGCCGGGAACGAGAAGACCGGCATCCTGACCGTGACCTACCACAGCGAG
ACCCAGCGCACCAAGTTCCTGAACACCGTGGCCATCCCCGACAGCGTGCAGATCCTGGTG
GGCTACATGACCATGTAA

FIG.8

Comparison of protein expression of
native and synthetic HPV16 L1 genes

Comparison of protein expression of native and synthetic HPV 16 E1 genes a. mock
b. lacZ
c. synthetic 16 E2 isolate 6
d. synthetic 16 E2 isolate 11
e native 16 E2

Comparison of protein expression of native and synthetic HPV16 E7 genes a. mock
b. lacZ
c. synthetic HPV16 E7 isolate 2
d. synthetic HPV16 E7 isolate 4
e. native HPV16 E7

HPV16 L1 Gene-Building Oligomers

MN4A1 (SEQ.ID.NO:9)  5' ATG AGC CTG TGG CTG CCC AGC GAG GCC ACC GTG TAC
CTG CCT CCC GTG CCC GTG AGC AAG GTG GTG AGC ACC GAC GAG TAC GTG GCC CGC ACC
AAC ATC TAC TAC CAC GCC GGC ACC AGC CGC CTG CTG  3'

MN4A3 (SEQ.ID.NO:10)  5' CGC ATC CAC CTG CCC GAC CCC AAC AAG TTC GGC TTC
CCC GAC ACA AGC TTC TAC AAC CCC GAC ACC CAG CGC CTG GTG TGG GCC TGC GTG GGC
GTG GAG GTG GGC CGC GGC CAG CCC CTG GGC GTG GGC  3'

MN4A5 (SEQ.ID.NO:11)  5' GAG TGC ATC AGC ATG GAC TAC AAG CAG ACC CAG CTG TGC CTG ATC GGC TGC AAG CCT CCC ATC GGC GAG CAC TGG GGC AAG GGC AGC CCC TGC ACC AAC GTG GCC GTG AAC CCC GGC GAC TGC CCT CCC 3'

MN4A7 (SEQ.ID.NO:12) 5' GCC AAC AAG AGC GAG GTG CCC CTG GAC ATC TGC ACC AGC ATC TGC AAG TAC CCC GAC TAC ATC AAG ATG GTG AGC GAG CCC TAC GGC GAC AGC CTG TTC TTC TAC CTG CGC CGC GAG CAG ATG TTC GTG CGC 3'

MN4A9 (SEQ.ID.NO:13) 5' GCC AGC AGC AAC TAC TTC CCC ACT CCC AGC GGC AGC ATG GTG ACC AGC GAC GCC CAA ATC TTC AAC AAG CCC TAC TGG CTG CAG CGC GCC CAG GGC CAC AAC AAC GGC ATC TGC TGG GGC AAC CAG CTG 3'

MN4A11 (SEQ.ID.NO:14) 5' GAG TAC CTG CGC CAC GGC GAG GAG TAC GAC CTG CAG TTC ATC TTC CAG CTG TGC AAG ATC ACC CTG ACC GCC GAC GTG ATG ACC TAC ATC CAC AGC ATG AAC AGC ACC ATC CTG GAG GAC TGG AAC TTC GGC CTG 3'

MN4A13 (SEQ.ID.NO:15) 5' GCT CCC AAG GAG GAT CCC CTG AAG AAG TAC ACC TTC TGG GAG GTG AAC CTG AAG GAG AAG TTC AGC GCC GAC CTG GAC CAG TTC CCC CTG GGC CGC AAG TTC CTG CTG CAG GCC GGC CTG AAG GCC AAG CCC AAG 3'

MN4A2 (SEQ.ID.NO:16) 5' GTT GGG GTC GGG CAG GTG GAT GCG GAA CAC GCG GTA CTG CAG GCC GCT CAC CTT GGG CAC CAG GAT CTT GTT GTT GTT GGG CTT CTT GAT GGG GAA GTA GGG GTG GCC CAC GGC CAG CAG GCG GCT GGT GCC GGC 3'

FIG.17A

MN4A4 (SEQ.ID.NO:17) 5' CTT GTA GTC CAT GCT GAT GCA CTC GCG GTT GTC CAC GCC GGC GTT GGC GGC GTA GGC GCT GGC GTT CTC GGT GTC GTC CAG CTT GTT CAG CAG GGG GTG GCC GCT GAT GCC CAC GCC CAG GGG CTG GCC GCG 3'

MN4A6 (SEQ.ID.NO:18) 5' CAG GGG CAC CTC GCT CTT GTT GGC CTG CAG GGT GGT GAA GTC CAT GGC GCC GAA GCC GGT GTC CAC CAT GTC GCC GTC CTG GAT CAC GGT GTT GAT CAG CTC CAG GGG AGG GCA GTC GCC GGG GTT CAC 3'

MN4A8 (SEQ.ID.NO:19) 5' GGG AGT GGG GAA GTA GTT GCT GCT GGC CAG GTT GGC GGT GCT GCC GCT GCC CTT GAT GTA CAG GTC GTC GGG CAC GTT CTC GCC CAC GGC GCC GGC GCG GTT GAA CAG GTG GCG CAC GAA CAT CTG CTC GCG 3'

MN4A10 (SEQ.ID.NO:20) 5' CTC CTC GCC GTG GCG CAG GTA CTC CTT GAA GTT GGT GTT CTT GTA GGT GGT CTC GCT GGT GCT GAT GGC GGC GCA CAG GCT CAT GTT GGT GCT GCG GGT GGT GTC CAC CAC GGT CAC GAA CAG CTG GTT GCC CCA GCA GAT GCC 3'

MN4A12 (SEQ.ID.NO:21) 5' CTT CAG GGG ATC CTC CTT GGG AGC GGG AGG GGT GTG CTT CTG GCA GGC GAT GGC CTG GCT GGT CAC GAA GCG GTA GGT GTC CTC CAG GGT ACC GCC GGG AGG GGG CTG CAG GCC GAA GTT CCA GTC CTC CAG 3'

MN4A14 (SEQ.ID.NO:22) 5' CAC TAG AGA TCT GAA TTC TTA CAG CTT GCG CTT CTT GCG CTT GGC GGT GGT GCT GGT GCT GCT GGT GGT GGG GGT GGC CTT GCG CTT GCC CAG GGT GAA CTT GGG CTT GGC CTT CAG GCC GGC 3'

MN595 (SEQ.ID.NO:23) 5' CGC GGC CAG CCC CTG GGC GTG 3'

MN596 (SEQ.ID.NO:24) 5' GCC CAC GCC CAG GGG CTG GCC GCG 3'

MN597 (SEQ.ID.NO:25) 5' GCC AAC AAG AGC GAG GTG CCC 3'

MN598 (SEQ.ID.NO:26) 5' CAG GGG CAC CTC GCT CTT GTT GGC 3'

MN599 (SEQ.ID.NO:27) 5' GCC AGC AGC AAC TAC TTC CCC AC 3'

MN600 (SEQ.ID.NO:28) 5' GGG AGT GGG GAA GTA GTT GCT GC 3'

MN601 (SEQ.ID.NO:29) 5' CTG GAG GAC TGG AAC TTC GGC CTG 3'

MN602 (SEQ.ID.NO:30) 5' CAG GCC GAA GTT CCA GTC CTC CAG 3'

MN603 (SEQ.ID.NO:31) 5' CAC TAG AGA TCT GAA TTC TTA CAG C 3'

MN604 (SEQ.ID.NO:32) 5' CAT CTC AGA TCT GCC ACC ATG AGC CTG TGG CTG CCC AG 3'

FIG.17B

HPV16E1 Gene-building Oligomers

MN605 (SEQ.ID.NO:33)  5' ATG GCC GAC CCC GCC GGC ACC AAC GGC GAG GAG GGC ACC
GGC TGC AAC GGC TGG TTC TAC GTG GAG GCC GTG GTG GAG AAG AAG ACC GGC GAC GCC ATC
AGC GAC GAC GAG AAC GAG AAC GAC AGC GAC    3'

MN606 (SEQ.ID.NO:34)  5' GTG CTG CTT GGC CTC CTG GGC GGT GAA CAG GGC GTG GGC
GGT CTC GGT CTC GGC CTG GGT CAG GTA GTC GTT GTC GTT CAC GAT GAA GTC CAC CAG GTC
CTC GCC GGT GTC GCT GTC GTT CTC GTT CTC GTC   3'

MN607(SEQ.ID.NO:35)  5' GCC CAG GAG GCC AAG CAG CAC CGC GAC GCC GTG CAG GTG CTG
AAG CGC AAG TAC CTG GGC AGC CCC CTG AGC GAC ATC AGC GGC TGC GTC GAC AAC AAC ATC
AGC CCC CGC CTG AAG GCC ATC TGC ATC GAG   3'

MN608 (SEQ.ID.NO:36) 5' CTC GTG GCG GCC CTC CAC CTG CAG CAT CTG CTG GGT CTC CAC
CTC GGT GTT GCC GTA GCC GCT GTC CTC GCT CTC GAA CAG GCG GCG CTT GGC GGC GCG GCT
CTG CTT CTC GAT GCA GAT GGC CTT CAG GC    3'

MN609 (SEQ.ID.NO:37)  5' CAG GTG GAG GGC CGC CAC GAG ACC GAG ACC CCC TGC AGC
CAG TAC AGC GGC GGC AGC GGC GGC GGC TGC AGC CAG TAC AGC AGC GGC AGC GGC GGC GAG
GGC GTG AGC GAG CGC CAC ACC ATC TGC CAG ACC    3'

MN610 (SEQ.ID.NO:38):  5' CTT GAA GGG GCG CAC CAG CTC GCT GAA GCT CAC GCC GTA CAG CTC CTT GAA CTT GGC CAG CAT GGC GGC CTT GGC GTT GCT GGT CTT CAG CAC GTT CAG GAT GTT GGT CAG AGG GGT CTG GCA GAT GGT GTG GCG 3'

MN611 (SEQ.ID.NO:39) 5' GAG CTG GTG CGC CCC TTC AAG AGC AAC AAG AGC ACC TGC TGC GAC TGG TGC ATC GCC GCC TTC GGC CTG ACC CCC AGC ATC GCC GAC AGC ATC AAG ACC CTG CTG CAG CAG TAC TGC CTG TAC CTG CAC ATC CAG 3'

MN612 (SEQ.ID.NO:40) 5' CAT GGG GCT CAC GCA CAG CAG CTT GCT CAG CAG CTT CTC GAT GGT CTC GCG GTT CTT GCC GCA CTT GTA GCG CAC CAG CAG CAG CAC CAC CAT GCC CCA GCT GCA GGC CAG GCT CTG GAT GTG CAG GTA CAG GCA G 3'

FIG.18A

MN613 (SEQ.ID.NO:41)  5' CTG CTG TGC GTG AGC CCC ATG TGC ATG ATG ATC GAG CCT CCC AAG CTT CGC AGC ACC GCC GCC GCC CTG TAC TGG TAC AAG ACC GGC ATC AGC AAC ATC AGC GAG GTG TAC GGC GAC ACC CCC GAG TGG ATC  3'

MN614 (SEQ.ID.NO:42)  5' GGC GAT CTC GCT GTC GTC CAC GAT GTC GTT GTC GTA GGC CCA CTG CAC CAT CTG GCT CAG CTC GAA GGT GCA GTC GTT GAA GCT GTG CTG CAG CAC GGT CTG GCG CTG GAT CCA CTC GGG GGT GTC GCC  3'

MN615 (SEQ.ID.NO:43):  5' GTG GAC GAC AGC GAG ATC GCC TAC AAG TAC GCC CAG CTG GCC GAC ACC AAC AGC AAC GCC AGC GCC TTC CTG AAG AGC AAC AGC CA GGC CAA GAT CGT GAA GGA CTG CGC CAC CAT GTG CCG CCA CTA C 3'

MN616 (SEQ.ID.NO:44)  5' GTA GCG CAG GAA CAT CAC GAT CTG CTT GCG GTC GCC GCC GTC GTC CAC GCG GTC GCA GCG GTA CTT GAT CCA CTG GCT CAT GCT CAT CTG CTT CTT CTC GGC GCG CTT GTA GTG GCG GCA CAT GGT GGC  3'

MN617 (SEQ.ID.NO:45)  5' CAG ATC GTG ATG TTC CTG CGC TAC CAG GGC GTG AAA TTC ATG AGC TTC CTG ACC GCC CTG AAG CGC TTC CTG CAG GGC ATC CCC AAG AAG AAC TGC ATC CTG CTG TAC GGC GCC GCC AAC ACC GAC AAG  3'

MN618 (SEQ.ID.NO:46)  5' GCC GAT CTT GGC GTC GGC CAG GGG CTG CAG CCA GAA GTG GCT CTT GCT GTT CAC GAA GCA GAT CAC GCT GCC CTG CAG GAA CTT CAT CAG GCT CAT GCC GAA CAG GCT CTT GTC GGT GTT GGC GGC GCCG  3'

MN619 (SEQ.ID.NO:47)  5' CTG GCC GAC GCC AAG ATC GGC ATG CTG GAC GAC GCC ACC GTG CCC TGC TGG AAC TAC ATC GAC GAC AAC CTG CGC AAC GCC CTG GAC GGC AAC CTG GTG AGC ATG GAC GTG AAG CAC CGC CCC CTG GTG  3'

MN620 (SEQ.ID.NO:48)  5' GAA CTC GTT GGG GAA GGT GAA CAC CAC CAG GCG GTT GTG CAG GTA GGG CCA GCG GCT GTC GGT GCC GGC GTT GAT GTT GCT GGT GAT CAG CAG GGG AGG GCA CTT CAG CTG CAC CAG GGG GCG GTG CTT CAC  3'

FIG.18B

MN621 (SEQ.ID.NO:49)  5' GTG TTC ACC TTC CCC AAC GAG TTC CCC TTC GAC GAG AAC GGT AAC CCC GTG TAC GAG CTG AAC GAC AAG AAC TGG AAG AGC TTC TTC AGC CGC ACC TGG AGC CGC CTG AGC CTG CAC GAG GAC GAG  3'

MN622 (SEQ.ID.NO:50)  5' CAT GAG AGA TCT TTA CAG GGT GTT GGT GTT CTG GCC GCT CAC GCA CTT GAA GGT GGG CAG GCT GTC GCC GTC GTT CTC CTT GTC CTC GTC CTC GTG CAG GCT CAG  3'

MN623 (SEQ.ID.NO:51)  5' GCC TGA AGG CCA TCT GCA TCG AG  3'

MN624 (SEQ.ID.NO:52)  5' CTC GAT GCA GAT GGC CTT CAG GC  3'

MN625 (SEQ.ID.NO:53)  5' GAG CTG GTG CGC CCC TTC AAG  3'

MN626 (SEQ.ID.NO:54)  5' CTT GAA GGG GCG CAC CAG CTC  3'

MN627 (SEQ.ID.NO:55)  5' CTG CTG TGC GTG AGC CCC ATG  3'

MN628 (SEQ.ID.NO:56)  5' CAT GGG GCT CAC GCA CAG CAG  3'

MN629 (SEQ.ID.NO:57)  5' GCC ACC ATG TGC CGC CAC TAC  3'

MN630 (SEQ.ID.NO:58)  5' GTA GTG GCG GCA CAT GGT GGC  3'

MN631 (SEQ.ID.NO:59)  5' CTG GCC GAC GCC AAG ATC GGC  3'

MN632 (SEQ.ID.NO:60)  5' GCC GAT CTT GGC GTC GGC CAG  3'

MN633 (SEQ.ID.NO:61)  5' GTG TTC ACC TTC CCC AAC GAG TTC  3'

MN634 (SEQ.ID.NO:62)  5' GAA CTC GTT GGG GAA GGT GAA CAC  3'

MN635 (SEQ.ID.NO:63)  5' CAT GAG AGA TCT TTA CAG GGT GTT G  3'

MN636 (SEQ.ID.NO:64)  5' CAT CTC AGA TCT GCC ACC ATG GCC GAC CCC GCC GGC AC  3'

FIG.18C

Oligonucleotides used in the generation of synthetic HPV 16 E2

13856-307-2A (SEQ.ID.NO:65)  5' ATG GAG ACC CTG TGC CAG CGC CTG AAC GTG TGC CAG GAC AAG ATC CTG ACC CAC TAC GAG AAC GAC AGC ACC GAC CTG CGC GAC CAC ATC GAC TAC TGG  3'

13856-307-2C (SEQ.ID.NO:66)  5' CCA CCA GGT GGT GCC CAC CCT GGC CGT GAG CAA GAA CAA GGC CCT GCA GGC CGC CGA GCT GCA GCT GAC CCT GGA GAC GAT CTA CAA CAG CCA GTA CAG CAA CG  3'

13856-307-2E (SEQ.ID.NO:67)  5' CCG GCT GCA TCA AGA AGC ACG GCT ACA CCG TGG AGG TGC AGT TCG ACG GCG ACA TCT GCA ACA CCA TGC ACT ACA CCA ACT GGA CCC ACA TTT ACA TCT GTG AGG AGG  3'

13856-307-2G (SEQ.ID.NO:68)  5' CGT GCA CGA GGG GAT CCG CAC CTA CTT CGT GCA GTT CAA GGA CGA CGC CGA GAA GTA CAG CAA GAA CAA GGT GTG GGA GGT GCA CGC CGG AGG CCA GGT GAT CC  3'

13856-307-2I (SEQ.ID.NO:69)  5' GGC CAA CCA CAG CGC CGC CAC CCA CAC CAA GGC CGT GGC CCT GGG CAC CGA GGA GAC CCA GAC CAC AAT CCA GCG CCC TCG CAG CGA GCC CGA CAC CGG CAA CCC CTG CC  3'

13856-307-2K (SEQ.ID.NO:70)  5' GCC ACA AGG GCC GGA TCA ACT GCA ACA GCA ACA CCA CCC CTA TCG TGC ACC TGA AGG GCG ACG CCA ACA CCC TGA AGT GCC TGC GGT ACC GCT TCA AGA AGC ACT GC  3'

13856-307-2B (SEQ.ID.NO:71)  5' CCA GGG TGG GCA CCA CCT GGT GGT TGA TGT GCT TGA AGC CCA TCT CGC GGG CCT TGT AGT AGA TGG CGC AGG CCA GGC GCA TGT GCT TCC AGT AGT CGA TGT GGT CGC GCA GG  3'

13856-307-2D (SEQ.ID.NO:72)  5' GCC GTG CTT CTT GAT GCA GCC GGT AGG GGC GGT CAG GTA CAC CTC CAG GCT CAC GTC CTG CAG GGT CCA CTT CTC GTT GCT GTA CTG GCT GTT GTA GAT CG  3'

13856-307-2F (SEQ.ID.NO:73)  5' GGT GCG GAT CCC CTC GTG CAC GTA GTA CAG GCC GTA GTA GTC CAC CTG GCC CTC CAC CAC GGT CAC GCT GGC CTC CTC ACA GAT GTA AAT GTG GGT CC  3'

13856-307-2H (SEQ.ID.NO:74)  5' GGG TGG CGG CGC TGT GGT TGG CCA GGT GCT GGC GGA TCG TCT CGG GGC TGC TCA CCT CGT TGC TGC TGA ACA CGC TGG TGG GCA CA GGA TCA CCT GGC TCC GGC GTG C  3'

FIG.19A 13856-307-2J (SEQ.ID.NO:75)  5' GCA GTT GAT CCG GCC CTT GTG GCT GCT GTT GAA GGC GGT CAG GAT AGG GGC GCT GTC GAC GCT GTC GCG GTG CAG CAG CTT GGT GGT GTG GCA GGG GTT GCC GGT GTC GGG  3'

13856-307-2L (SEQ.ID.NO:76)  5' CGT AGG TCA GGG TCA CGA TAG CGC TCT TGT GCT TCA CGT TGT GGC CGG TCC AGT GCC AGG TGC TGC TCA CGG CGG TGT ACA GCT TGC AGT GCT TCT TGA AGC GGT ACC GC  3'

13856-307-2M (SEQ.ID.NO:77)  5' TTT AGA TGC TCA TGA AGC CGG TGC TCA CGG TGA TGG TCT TGG GGA TCT TCA CCT GGC TCA GGA ACT GGT CGC GCT GCC ACT CGC TGT CGT AGG TCA GGG TCA CGA TAG CGC  3'

13856-307-2PA (SEQ.ID.NO:78)  5' CGA GCT GAT ATC GAA TTC AGA TCT GCC ACC ATG GAG ACC CTG TGC AGC CG  3'

13856-307-2PM (SEQ.ID.NO:79)  5' GGT TGC AGA TCT AGA CTC GAG TTT AGA TGC TCA TGA AGC CGG TGC  3'

13856-307-2PE (SEQ.ID.NO:80)  5' CCG GCT GCA TCA AGA AGC ACG  3'

13856-307-2PI (SEQ.ID.NO:81)  5' GGC CAA CCA CAG CGC CGC C  3'

13856-307-2PD (SEQ.ID.NO:82)  5' GCC GTG CTT CTT GAT GCA GCC  3'

13856-307-2PH (SEQ.ID.NO:83)  5' GGG TGG CGG CGC TGT GG  3'

13856-307-2PL (SEQ.ID.NO:84)  5' CGT AGG TCA GGG TCA CGA TAG C  3'

FIG.19B

Oligonucleotides used in the generation of synthetic HPV 16 E7.

13856-307-7A (SEQ.ID.NO:85)  5' GGC CGG AGA TCT GAT ATC GAA TTC GCC ACC
ATG CAC GGC GAC ACC CCC ACC CTG CAC GAG TAC ATG CTG GAC CTG CAG CCC GAG
ACC ACC GAC CTG TAC GGC TAC GGC     C  3'

13856-307-7C (SEQ.ID.NO:86)  5' GCC GAG CCC GAC CGC GCC CAC TAC AAC ATC
GTG ACC TTC TGC TGC AAG TGC GAC AGC ACC CTG CGC CTG TGC GTG CAG AGC ACC
CAC GTC GAC ATC CGC ACC CTG G  3'

13856-307-7B (SEQ.ID.NO:87)  5' GGG CGC GGT CGG GCT CGG CCT GGC CGG CGG
GGC CGT CGA TCT CGT CCT CTT CCT CGC TGC TGT CGT TCA GCT GGC CGT AGC CGT
ACA GGT CGG TGG  3'

13856-307-7D (SEQ.ID.NO:88)  5' CCG CGG CAG ATC TAG ACT CGA GTT TAG GGC
TTC TGG CTG CAG ATT GGG CAC ACG ATT CCC AGG GTG CCC ATC AGC AGG TCC TCC
AGG GTG CGG ATG TCG ACG TGG G  3'

13856-307-7PA (SEQ.ID.NO:89)  5' GGC CGG AGA TCT GAT ATC GAA TTC G  3'

13856-307-7PD (SEQ.ID.NO:90)  5' CCG CGG CAG ATC TAG ACT CG  3'

FIG.20

Oligonucleotides Used for Construction of HPV6a E7 Gene

A. DNA Template Oligos

LS207 (105-mer) (SEQ.ID.NO:91)  5' GTC ACA GAT CTG ATA TCG AAT TCC ACC ATG CAC GGC CGC CAC GTG ACC CTG AAG GAC ATC GTG CTG GAC CTG CAG CCT CCC GAC CCC GTG GGC CTG CAC TGC TAC  3'

LS208 (105-mer) (SEQ.ID.NO:92)  5' CTG GAA GTG CTG CTT CAG GGG CTG GCT GTC CTG GCC GTC CAC CTC GTC CAC CTC GTC CTC GCT GCT GTC CAC CAG CTG CTC GTA GCA GTG CAG GCC CAC GGG GTC  3'

LS209 (107-mer) (SEQ.ID.NO:93)  5' CCA GCC CCT GAA GCA GCA CTT CCA GAT CGT GAC CTG CTG CTG CGG CTG CGA CAG CAA CGT GCG CCT GGT GGT GCA GTG CAC CGA GAC CGA CAT CCG CGA GGT GCA GC  3'

LS210 (102-mer) (SEQ.ID.NO:94)  5' CAG TCA GAT CTA GAG ATA TCT TTA GGT CTT GGG AGC GCA GAT GGG GCA CAC GAT GTT CAG GGT ACC AGC AGA GCT GCT G CAC CTC GCG GAT GTC GGT CTC  3'

B. PCR Amplification Primers

LS211 (24-mer) (SEQ.ID.NO:95)  5' GTC ACA GAT CTG ATA TCG AAT TCC  3'

LS212 (26-mer) (SEQ.ID.NO:96)  5' CAG TCA GAT CTA GAG ATA TCT TTA GG  3'

FIG.21

Oligonucleotides Used for Construction of HPV18 E7 Gene

A. DNA Template Oligos

LS201 (109-mer) (SEQ.ID.NO:97)  5' GTC ACA GAT CTG ATA TCG AAT TCC ACC ATG
CAC GGC CCC AAG GCC ACC CTG CAG GAC ATC GTG CTG CAC CTG GAG CCC CAG AAC GAG
ATC CCC GTG GAC CTG CTG TGC     C 3'

LS202 (111-mer) (SEQ.ID.NO:98)  5' GGG CTC GGC CCT GCG AGC GGG CAG GTG CTG
GTG GTT CAC GCC GTC GAT CTC GTC GTT CTC CTC CTC GCT GTC GCT CAG CTG CTC GTG
GCA CAG CAG GTC CAC GGG GAT CTC 3'

LS203 (108-mer) (SEQ.ID.NO:99)  5' GCC CGC TCG CAG GGC CGA GCC CCA GCG CCA
CAC CAT GCT GTG CAT GTG CTG CAA GTG CGA GGC CCG CAT CGA GCT GGT GGT GGA GAG
CAG CGC TGA CGA CCT GCG CGC 3'

LS204 (109-mer) (SEQ.ID.NO:100)  5' CAG TCA GAT CTA GAG ATA TCT TTA CTG CTG
GCT GGC GCA CCA GGG GCA CAC GAA GCT CAG GGT GTT CAG GAA CAG CTG CTG GAA GGC
GCG CAG GTC GTC AGC GCT GCT C 3'

B. PCR Amplification Primers

LS205 (26-mer) (SEQ.ID.NO:101)  5' GTC ACA GAT CTG ATA TCG AAT TCC AC 3'

LS206 (27-mer) (SEQ.ID.NO:102)  5' CAG TCA GAT CTA GAG ATA TCT TTA CTG 3'

FIG.22

Oligonucleotides used in the construction of HPV6 E2

6A  1-84 (90mer) (SEQ.ID.NO:103)  5' GAA TTC AGA TCT GAT ATC ACC ATG GAG GCC ATC GCC AAG CGC CTG GAC GCC TGC CAG GAG CAG CTG CTG GAG CTG TAC GAG GAG AAC AGC  3'

6B  65-157 (92mer) (SEQ.ID.NO:104)  5' CCT TGT ACA GCA GCA CGC TCT CGT GGC GCA TGC ACT TCC AGT GCA GCA CGT GCT TGT GCA GGT CGG TGC TGT TCT CCT CGT ACA GCT CCA GC  3'

6C  132-227 (96mer) (SEQ.ID.NO:105)  5' CCA CGA GAG CGT GCT GCT GTA CAA GGC CAA GCA GAT GGG CCT GAG CCA CAT CGG CAT GCA GGT GGT GCC TCC TCT GAA GGT GAG CGA GGC CAA GGG  3'

6D  202-304 (103mer) (SEQ.ID.NO:106)  5' GCA GGG TCC AGG GCT CCA TGC TGT ACT CGG TGC GCA GCA GGC TCT CGA GGT GCA TCT GCA TCT CGA TGG CGT TGT GGC CCT TGG CCT CGC TCA CCT TCA GAG G  3'

6E  276-373 (98mer) (SEQ.ID.NO:107)  5' CGA GTA CAG CAT GGA GCC CTG GAC CCT GCA GGA GAC CAG CTA CGA GAT GTG GCA GAC CCC TCC AAG CGC TGC TTC AAG AAG CGC GGC AAG AC CGT GG  3'

6F  347-448 (102mer) (SEQ.ID.NO:108)  5' CGT TGT CCT GCA CGT ACA CGT CGG TCC ACA CCA CGT AGT CCA TGG TGT TGT TGG CGC AGC CGT CGA ACT TCA CCT CCA CGG TCT TGC CGC GCT TCT TGA AGC  3'

6G  425-526 (102mer) (SEQ.ID.NO:109)  5' CCG ACG TGT ACG TGC AGG ACA ACG ACA CCT GGG TGA AGG TGC ACA GCA TGG TGG ACG CCA AGG CAT CTA CT ACA CCT GTG GCC AGT TCA AGA CCT ACT ACG  3'

6H  495-586 (92mer) (SEQ.ID.NO:110)  5' GCT GCC GTA GCA CAC CTC CCA GTG CTT GGT GCT GCC GTA CTT CTC GGC CTC CTT CAC GAA GTT CAC GTA GTA GGT CTT GAA CTG GCC ACA GG  3'

6I  500-591 (94mer) (SEQ.ID.NO:111)  5' GCA CTG GGA GGT GTG CTA CGG CAG CAC CGT GAT CTG CAG CCC CGC TAG CGT GAG CAG CAC CAC CCA GGA GGT GAG CAT CCC CGA GAG CAC CAC C  3'

6J  636-732 (97mer) (SEQ.ID.NO:112)  5' GCG AGG AGG GGT CTG CAC GGC GTC CTC CTT GGT GCT GCT GCT CAC CAG GGT GCT GGT CTG GCG GGA GTA GGT GGT GCT CTC GGG GAT GCT CAC C  3'

FIG.23A 6K  708-804 (97mer) (SEQ.ID.NO:113)  5' GGA CGC CGT GCA GAC CCC TCC TCG CAA GCG CGC CCG CGG CGT GCA GCA GAG CCC CTG CAA CGC CCT GTG CGT GGC CCA CAT CGG CCC CGT GGA CAG C  3'

6L  780-873 (94mer) (SEQ.ID.NO:114)  5' GGC GCT GCT GTT GCT GTT GTT GCG GCG CTG GTG CTG GTC GTG GTT GTT GGT GAT CAG GTT GTG GTT GCC GCT GTC CAC GGG GCC GAT GTG GGC C  3'

6M  849-943 (95mer) (SEQ.ID.NO:115)  5' CCG CAA CAA CAG CAA CAG CAG CGC CAC TCC CAT CGT GCA GTT CCA GGG CGA GAG CAA CTG CCT GAA GTG CTT CCG CTA CCG CCT GAA CGA TCG CC  3'

6N  917-1012 (96mer) (SEQ.ID.NO:116)  5' CGT GCT TGT GGG GAG CCT TGC TGC TGG CCC AGT GCC AGG TGC TGC TGA TCA GGT CGA ACA GGT GGC GGT GGC GAT CGT CAG GCG GTA GCG GAA GC  3'

6O  989-1083 (95mer) (SEQ.ID.NO:117)  5' GCA GCA AGG CTC CCC ACA AGC ACG CCA TCG TGA CCG TGA CCT ACG ACA GCG AGG AGC AGC GCC AGC AGT CCT GGA CG TGG TGA AGA TCC CTC CC  3'

6P  1059-1154 (96mer) (SEQ.ID.NO:118)  5' CTC GAG AGA TCT CCC GGG TCT AGA GCT TAC AGC AGG TGC AGG CTC ATG AAG CCC AGC TTG TGG CTG ATG GTG GAG GGA TCT TCA CCA CGT CCA GG  3'

6PA  25mer (SEQ.ID.NO:119)  5' GAA TTC AGA TCT GAT ATC ACC ATG   G 3'

6PD  21mer (SEQ.ID.NO:120)  5' GCA GGG TCC AGG GCT CCA TGC 3'

6PE  25mer (SEQ.ID.NO:121)  5' CGA GTA CAG CAT GGA GCC CTG GAC C 3'

6PH  25mer (SEQ.ID.NO:122)  5' GCT GCC GTA GCA CAC CTC CCA GTG C 3'

6PI  21mer (SEQ.ID.NO:123)  5' GCA CTG GGA GGT GTG CTA CGG 3'

6PL  23mer (SEQ.ID.NO:124)  5' GGC GCT GCT GTT GCT GTT GTT GC 3'

6PM  22mer (SEQ.ID.NO:125)  5' CCG CAA CAA CAG CAA CAG CAG C 3'

6PP  26mer (SEQ.ID.NO:126)  5' CTC GAG AGA TCT CCC GGG TCT AGA GC 3'

FIG.23B

Oligonucleotides used to construct HPV18 E2

18A  1-97 (97mer) (SEQ.ID.NO:127)  5' GAA TTC AGA TCT GAT ATC ACC ATG CAG ACT CCC AAG GAG ACC CTG AGC GAG CGC CTG AGC GCC CTG CAG GA CAA GAT CAT CGA CCA CTA CGA GAA CG  3'

18B  69-166 (98mer) (SEQ.ID.NO:128)  5' CGA AGA AGA TGG CGT TCT CCC AGC GGA TCA GCT GCC AGT ACT GGA TCT GGC TGT CGA TGT CCT TGC TGT CGT TCT CGT AGT GGT CGA TGA TCT TGT CC  3'

18C  141-234 (94mer) (SEQ.ID.NO:129)  5' CCG CTG GGA GAA CGC CAT CTT CTT CGC CGC TCG CGA GCA CGG GAT CCA GAC CCT GAA CCA CCA GGT GGT GCC CGC CTA CAA CAT CAG CAA GAG C  3'

18D  211-304 (94mer) (SEQ.ID.NO:130)  5' CCT CGG TCT TGT AGG CGC TCT GGG CCA GGC CCT GCA GGG CCA TCT GCA GCT CGA TGG CCT TGT GGG CCT GCT CTT GCT GAT GTT GTA GGC GGG  3'

18E  281-371 (91mer) (SEQ.ID.NO:131)  5' CCC AGA GCG CCT ACA AGA CCG AGG ACT GGA CCC TGC AGG ACA CCT GCG AGG AGC TGT GGA ACA CCG AGC CCA CCC ACT GCT TCA AGA AGG G  3'

18F  348-441 (94mer) (SEQ.ID.NO:132)  5' GCT GTC CCA GGC CAC GTA GTT CAT GCA GTT GTC CTT GTT GCC GTC GAA GTA CAC CTG CAC GGT CTG CCT CCT TCT TGA AGC AGT GGG TGG GC  3'

18G  416-505 (90mer) (SEQ.ID.NO:133)  5' GCA TGA ACT ACG TGG CCT GGG ACA GCG TGT ACT ACA TGA CCG ACG CCG GCA CCT GGG ACA AGA CCG CCA CCT GCG TGA GCC ACC GCG GCC  3'

18H  481-572 (92mer) (SEQ.ID.NO:134)  5' CCG TAC TTC TCG CAC TCG CTC TTG AAC TCG ATG TAG AAG GTG TTG TAG CCC TCC TTC ACG TAG TAC AGG CCG CGG TGG CTC ACG CAG GTG GC  3'

18I  543-636 (94mer) (SEQ.ID.NO:135)  5' CGA GTT CAA GAG CGA GTG CGA GAA GTA CGG CAA CAC CGG CAC CTG GGA GGT GCA CTT CGG CAA CAA CGT GAT CGA CTG CAA CGA CAG CAT GTG C  3'

18J  609-708 (100mer) (SEQ.ID.NO:136)  5' GCT GTA GGG GCT GGG AGT GTG CTG CAG CTG CTT CAC CAG CTG GGT GGC GCT CAC GGT GTC GTC GCT GGT GCT GCA CAT GCT GTC GTT GCA GTC GAT CAC G  3'

FIG.24A 18K  687-779 (93mer) (SEQ.ID.NO:137)  5' GCA CAC TCC CAG CCC CTA CAG CAG
CAC CGT GAG CGT GGG CAC CGC CAA GAC CTA CGG CCA GAC CAG CGC CGC CAC TCG
CCC TGG CCA CTG CGG  3'

18L  758-853 (96mer) (SEQ.ID.NO:138)  5' GCT TGT TGT TGC CGG TGG CGG TGG
CGG CGC CCA GCA GAG GGT TCA CGG GCC CGC AGT GCT GCT TCT CGG CCA GGC CGC
AGT GGC CAG GGC GAG TGG  3'

18M  829-925 (97mer) (SEQ.ID.NO:139)  5' GCC ACC GCC ACC GGC AAC AAC AAG
CGC CGC AAG CTG TGC AGC GGC AAC ACC ACT CCC ATC ATC CAC CTG AAG GGC GAC
CGC AAC AGC CTG AAG TGC C  3'

18N  900-996 (97mer) (SEQ.ID.NO:140)  5' GGC GCC GGT CCA GTG CCA GGT GCT
GCT GAT GTC GCG GTA GTG GTC GCT GTG CTT GCG CAG GCG GTA CCG CAG GCA CTT
CAG GCT GTT GCG GTC GCC C  3'

18O  974-1072 (99mer) (SEQ.ID.NO:141)  5' GCA CCT GGC ACT GGA CCG GCG
CCG GGA ACG AGA AGA CCG GCA TCC TGA CCG TGA CCT ACC ACA GCG AGA CCC AGC
GCA CCA AGT TCC TGA ACA CCG TGG  3'

18P  1048-1145 (98mer) (SEQ.ID.NO:142)  5' CTC GAG AGA TCT CCC GGG TCT
AGA GCT TAC ATG GTC ATG TAG CCC ACC AGG ATC TGC ACG CTG TCG GGG ATG GCC
ACG GTG TTC AGG AAC TTG GTG CG  3'

18PA 25mer (SEQ.ID.NO:143)  5' GAA TTC AGA TCT GAT ATC ACC ATG    C 3'

18PD 23mer (SEQ.ID.NO:144)  5' CCT CGG TCT TGT AGG CGC TCT GG  3'

18PE 21mer (SEQ.ID.NO:145)  5' CCC AGA GCG CCT ACA AGA CCG  3'

18PH 21mer (SEQ.ID.NO:146)  5' CCG TAC TTC TCG CAC TCG CTC  3'

18PI 20mer (SEQ.ID.NO:147)  5' CGA GTT CAA GAG CGA GTG CG  3'

18PL 21mer (SEQ.ID.NO:148)  5' GCT TGT TGT TGC CGG TGG CGG  3'

18PM 25mer (SEQ.ID.NO:149)  5' GCC ACC GCC ACC GGC AAC AAC AAG C  3'

18PP 26mer (SEQ.ID.NO:150)  5' CTC GAG AGA TCT CCC GGG TCT AGA GC  3'

FIG.24B

SEQUENCE LISTING

<160> NUMBER OF SEQ ID NOS: 150

<210> SEQ ID NO 1
<211> LENGTH: 1518
<212> TYPE: DNA
<213> ORGANISM: Artificial Sequence
<220> FEATURE:
<223> OTHER INFORMATION: Codon-Optimized HPV16 L1

<400> SEQUENCE: 1

```
atgagcctgt ggctgcccag cgaggccacc gtgtacctgc ctcccgtgcc cgtgagcaag      60
gtggtgagca ccgacgagta cgtggcccgc accaacatct actaccacgc cggcaccagc     120
cgcctgctgg ccgtgggcca ccctacttc cccatcaaga agcccaacaa caacaagatc     180
ctggtgccca aggtgagcgg cctgcagtac cgcgtgttcc gcatccacct gcccgacccc     240
aacaagttcg gcttccccga cacaagcttc tacaaccccg acacccagcg cctggtgtgg     300
```

```
gcctgcgtgg gcgtggaggt gggccgcggc cagcccctgg gcgtgggcat cagcggccac      360
cccctgctga caagctgga cgacaccgag aacgccagcg cctacgccgc caacgccggc      420
gtggacaacc gcgagtgcat cagcatggac tacaagcaga cccagctgtg cctgatcggc      480
tgcaagcctc ccatcggcga gcactggggc aagggcagcc cctgcaccaa cgtggccgtg      540
aaccccggcg actgccctcc cctggagctg atcaacaccg tgatccagga cggcgacatg      600
gtggacaccg gcttcggcgc catggacttc accaccctgc aggccaacaa gagcgaggtg      660
cccctggaca tctgcaccag catctgcaag tacccgact acatcaagat ggtgagcgag      720
ccctacggca cagcctgtt cttctacctg cgccgcgagc agatgttcgt gcgccacctg      780
ttcaaccgcg ccggcgccgt gggcgagaac gtgcccgacg acctgtacat caagggcagc      840
ggcagcaccc ccaacctggc cagcagcaac tacttcccca ctcccagcgg cagcatggtg      900
accagcgacg cccaaatctt caacaagccc tactggctgc agcgcgccca gggccacaac      960
aacggcatct gctggggcaa ccagctgttc gtgaccgtgg tggacaccac ccgcagcacc     1020
aacatgagcc tgtgcgccgc catcagcacc agcgagacca cctacaagaa caccaacttc     1080
aaggagtacc tgcgccacgg cgaggagtac gacctgcagt tcatcttcca gctgtgcaag     1140
atcaccctga ccgccgacgt gatgacctac atccacagca tgaacagcac catcctggag     1200
gactggaact tcggcctgca gccccctccc ggcggtaccc tggaggacac ctaccgcttc     1260
gtgaccagcc aggccatcgc ctgccagaag cacacccctc ccgctcccaa ggaggatccc     1320
ctgaagaagt acaccttctg ggaggtgaac ctgaaggaga agttcagcgc cgacctggac     1380
cagttccccc tgggccgcaa gttcctgctg caggccggcc tgaaggccaa gcccaagttc     1440
accctgggca gcgcaaggc caccccacc accagcagca ccagcaccac cgccaagcgc     1500
aagaagcgca agctgtaa                                                    1518

<210> SEQ ID NO 2
<211> LENGTH: 1950
<212> TYPE: DNA
<213> ORGANISM: Artificial Sequence
<220> FEATURE:
<223> OTHER INFORMATION: Mutant, Codon-Optimized HPV16 E1

<400> SEQUENCE: 2
atggccgacc ccgccggcac caacggcgag gagggcaccg gctgcaacgg ctggttctac       60
gtggaggccg tggtggagaa gaagaccggc gacgccatca gcgacgacga gaacgagaac      120
gacagcgaca ccggcgagga cctggtggac ttcatcgtga cgacaacga ctacctgacc      180 caggccgaga ccgagaccgc ccacgccctg ttcaccgccc aggaggccaa gcagcaccgc      240
gacgccgtgc aggtgctgaa gcgcaagtac ctgggcagcc ccctgagcga catcagcggc      300
tgcgtcgaca caacatcag cccccgcctg aaggccatct gcatcgagaa gcagagccgc      360
gccgccaagc gccgcctgtt cgagagcgag gacagcggct acggcaacac cgaggtggag      420
acccagcaga tgctgcaggt ggagggccgc cacgagaccg agaccccctg cagccagtac      480
agcggcggca gcggcggcgg ctgcagccag tacagcagcg gcagcggcgg cgagggcgtg      540
agcgagcgcc acaccatctg ccagaccccct ctgaccaaca tcctgaacgt gctgaagacc      600
agcaacgcca aggccgccat gctggccaag ttcaaggagc tgtacggcgt gagcttcagc      660
gagctggtgc ccccttcaa gagcaacaag agcacctgct gcgactggtg catcgccgcc      720
ttcggcctga ccccagcat cgccgacagc atcaagaccc tgctgcagca gtactgcctg      780
tacctgcaca tccagagcct ggcctgcagc tggggcatgg tggtgctgct gctggtgcgc      840
```

-continued

```
tacaagtgcg gcaagaaccg cgagaccatc gagaagctgc tgagcaagct gctgtgcgtg      900
agccccatgt gcatgatgat cgagcctccc aagcttcgca gcaccgccgc cgccctgtac      960
tggtacaaga ccggcatcag caacatcagc gaggtgtacg cgacacccc cgagtggatc      1020 cagcgccaga ccgtgctgca gcacagcttc aacgactgca ccttcgagct gagccagatg     1080
gtgcagtggg cctacgacaa cgacatcgtg acgacagcg agatcgccta caagtacgcc      1140
cagctggccg acaccaacag caacgccagc gccttcctga gagcaacag ccaggccaag      1200 atcgtgaagg actgcgccac catgtgccgc cactacaagc gcgccgagaa gaagcagatg     1260
agcatgagcc agtggatcaa gtaccgctgc gaccgcgtgg acgacggcgg cgaccgcaag     1320
cagatcgtga tgttcctgcg ctaccagggc gtggaattca tgagcttcct gaccgccctg     1380
aagcgcttcc tgcagggcat ccccaagaag aactgcatcc tgctgtacgg cgccgccaac     1440
accgacaaga gcctgttcgg catgagcctg atgaagttcc tgcagggcag cgtgatctgc     1500
ttcgtgaaca gcaagagcca cttctggctg cagcccctgg ccgacgccaa gatcggcatg     1560
ctggacgacg ccaccgtgcc ctgctggaac tacatcgacg acaacctgcg caacgccctg     1620
gacggcaacc tggtgagcat ggacgtgaag caccgcccc tggtgcagct gaagtgccct      1680
cccctgctga tcaccagcaa catcaacgcc ggcaccgaca gccgctggcc ctacctgcac     1740
aaccgcctgg tggtgttcac cttccccaac gagttcccct cgacgagaa cggtaacccc      1800 gtgtacgagc tgaacgacaa gaactggaag agcttcttca gccgcacctg gagccgcctg     1860
agcctgcacg aggacgagga caaggagaac gacggcgaca gcctgcccac cttcaagtgc     1920
gtgagcggcc agaacaccaa caccctgtaa                                      1950
```

<210> SEQ ID NO 3
<211> LENGTH: 1098
<212> TYPE: DNA
<213> ORGANISM: Artificial Sequence
<220> FEATURE:
<223> OTHER INFORMATION: Mutant, Codon-Optimized HPV16 E2

<400> SEQUENCE: 3

```
atggagaccc tgtgccagcg cctgaacgtg tgccaggaca agatcctgac ccactacgag      60
aacgacagca ccgacctgcg cgaccacatc gactactgga gcacatgcg cctggcctgc      120 gccatctact acaaggcccg cgagatgggc ttcaagcaca tcaaccacca ggtggtgccc      180
accctggccg tgagcaagaa caaggccctg caggccgccg agctgcagct gaccctggag      240
accatctaca acagccagta cagcaacgag aagtggaccc tgcaggacgt gagcctggag      300
gtgtacctga ccgccccac cggctgcatc aagaagcacg gctacaccgt ggaggtgcag      360
ttcgacggcg acatctgcaa caccatgcac tacaccaact ggacccacat ctacatctgc      420
gaggaggcca gcgtgaccgt ggtggagggc caggtggact actacggcct gtactacgtg      480
cacgagggca tccgcaccta cttcgtgcag ttcaaggacg acgccgagaa gtacagcaag      540
aacaaggtgt gggaggtgca cgccggcggc caggtgatcc tgtgccccac cagcgtgttc      600
agcagcaacg aggtgagcag ccccgagacc atccgccagc cctggccaa ccacagcgcc      660 gccacccaca ccaaggccgt ggccctgggc accgaggaga cccagaccac catccagcgc      720
ccccgcagcg agcccgacac cggcaacccc tgccacacca ccaagctgct gcaccgcgac      780
agcgtggaca cgccccccat cctgaccgcc ttcaacagca gccacaaggg ccgcatcaac      840
tgcaacagca acaccacccc catcgtgcac ctgaagggcg acgccaacac cctgaagtgc      900
```

```
ctgcgctacc gcttcaagaa gcactgcaag ctgtacaccg ccgtgagcag cacctggcac      960
tggaccggcc acaacgtgaa gcacaagagc gccatcgtga ccctgaccta cgacagcgag     1020
tggcagcgcg accagttcct gagccaggtg aagatcccca agaccatcac cgtgagcacc     1080
ggcttcatga gcatctaa                                                   1098
```

<210> SEQ ID NO 4
<211> LENGTH: 297
<212> TYPE: DNA
<213> ORGANISM: Artificial Sequence
<220> FEATURE:
<223> OTHER INFORMATION: Mutant, Codon-Optimized HPV16 E7

<400> SEQUENCE: 4

```
atgcacggcg acaccccac cctgcacgag tacatgctgg acctgcagcc cgagaccacc       60
gacctgtacg gctacggcca gctgaacgac agcagcgagg aggaggacga gatcgacggc     120
cccgccggcc aggccgagcc cgaccgcgcc cactacaaca tcgtgacctt ctgctgcaag     180
tgcgacagca ccctgcgcct gtgcgtgcag agcacccacg tggacatccg caccctggag     240
gacctgctga tgggcaccct gggcatcgtg tgccccatct gcagccagaa gccctaa       297
```

<210> SEQ ID NO 5
<211> LENGTH: 297
<212> TYPE: DNA
<213> ORGANISM: Artificial Sequence
<220> FEATURE:
<223> OTHER INFORMATION: Codon-Optimized HPV6a E7

<400> SEQUENCE: 5

```
atgcacggcc gccacgtgac cctgaaggac atcgtgctgg acctgcagcc tcccgacccc      60
gtgggcctgc actgctacga gcagctggtg gacagcagcg aggacgaggt ggacgaggtg     120
gacggccagg acagccagcc cctgaagcag cacttccaga tcgtgacctg ctgctgcggc     180
tgcgacagca acgtgcgcct ggtggtgcag tgcaccgaga ccgacatccg cgaggtgcag     240
cagctcctgc tgggtaccct gaacatcgtg tgccccatct gcgctcccaa gacctaa      297
```

<210> SEQ ID NO 6
<211> LENGTH: 318
<212> TYPE: DNA
<213> ORGANISM: Artificial Sequence
<220> FEATURE:
<223> OTHER INFORMATION: Codon-Optimized HPV18 E7

<400> SEQUENCE: 6

```
atgcacggcc ccaaggccac cctgcaggac atcgtgctgc acctggagcc ccagaacgag      60
atccccgtgg acctgctgtg ccacgagcag ctgagcgaca gcgaggagga gaacgacgag     120
atcgacggcg tgaaccacca gcacctgccc gctcgcaggg ccgagcccca gcgccacacc     180
atgctgtgca tgtgctgcaa gtgcgaggcc cgcatcgagc tggtggtgga gagcagcgct     240
gacgacctgc gcgccttcca gcagctgttc ctgaacaccc tgagcttcgt gtgcccctgg     300
tgcgccagcc agcagtaa                                                   318
```

<210> SEQ ID NO 7
<211> LENGTH: 1107
<212> TYPE: DNA
<213> ORGANISM: Artificial Sequence
<220> FEATURE:
<223> OTHER INFORMATION: Codon-Optimized HPV6a E2

<400> SEQUENCE: 7

-continued

| | |
|---|---|
| atggaggcca tcgccaagcg cctggacgcc tgccaggagc agctgctgga gctgtacgag | 60 |
| gagaacagca ccgacctgca caagcacgtg ctgcactgga agtgcatgcg ccacgagagc | 120 |
| gtgctgctgt acaaggccaa gcagatgggc ctgagccaca tcggcatgca ggtggtgcct | 180 |
| cctctgaagg tgagcgaggc caagggccac aacgccatcg agatgcagat gcacctcgag | 240 |
| agcctgctgc gcaccgagta cagcatggag ccctggaccc tgcaggagac cagctacgag | 300 |
| atgtggcaga cccctcccaa gcgctgcttc aagaagcgcg gcaagaccgt ggaggtgaag | 360 |
| ttcgacggct cgccaacaa caccatggac tacgtggtgt ggaccgacgt gtacgtgcag | 420 |
| gacaacgaca cctgggtgaa ggtgcacagc atggtggacg ccaagggcat ctactacacc | 480 |
| tgtggccagt tcaagaccta ctacgtgaac ttcgtgaagg aggccgagaa gtacggcagc | 540 |
| accaagcact gggaggtgtg ctacggcagc accgtgatct gcagccccgc tagcgtgagc | 600 |
| agcaccaccc aggaggtgag catccccgag agcaccacct acactcccgc ccagaccagc | 660 |
| accctggtga gcagcagcac caaggaggac gccgtgcaga cccctcctcg caagcgcgcc | 720 |
| cgcggcgtgc agcagagccc ctgcaacgcc ctgtgcgtgg cccacatcgg ccccgtggat | 780 |
| agcggcaacc acaacctgat caccaacaac cacgaccagc accagcgccg caacaacagc | 840 |
| aacagcagcg ccactcccat cgtgcagttc cagggcgaga gcaactgcct gaagtgcttc | 900 |
| cgctaccgcc tgaacgatcg ccaccgccac ctgttcgacc tgatcagcag cacctggcac | 960 |
| tgggccagca gcaaggctcc ccacaagcac gccatcgtga ccgtgaccta cgacagcgag | 1020 |
| gagcagcgcc agcagttcct ggacgtggtg aagatccctc ccaccatcag ccacaagctg | 1080 |
| ggcttcatga gcctgcacct gctgtaa | 1107 |

<210> SEQ ID NO 8
<211> LENGTH: 1098
<212> TYPE: DNA
<213> ORGANISM: Artificial Sequence
<220> FEATURE:
<223> OTHER INFORMATION: Codon-Optimized HPV18 E2

<400> SEQUENCE: 8

| | |
|---|---|
| atgcagactc ccaaggagac cctgagcgag cgcctgagcg ccctgcagga caagatcatc | 60 |
| gaccactacg agaacgacag caaggacatc gacagccaga tccagtactg gcagctgatc | 120 |
| cgctgggaga cgccatctt cttcgccgct cgcgagcacg ggatccagac cctgaaccac | 180 |
| caggtggtgc ccgcctacaa catcagcaag agcaaggccc acaaggccat cgagctgcag | 240 |
| atggccctgc agggcctggc ccagagcgcc tacaagaccg aggactggac cctgcaggac | 300 |
| acctgcgagg agctgtggaa caccgagccc acccactgct tcaagaaggg aggccagacc | 360 |
| gtgcaggtgt acttcgacgg caacaaggac aactgcatga actacgtggc ctgggacagc | 420 |
| gtgtactaca tgaccgacgc cggcacctgg gacaagaccg ccacctgcgt gagccaccgc | 480 |
| ggcctgtact acgtgaagga gggctacaac accttctaca tcgagttcaa gagcgagtgc | 540 |
| gagaagtacg gcaacaccgg cacctggcag gtgcacttcg gcaacaacgt gatcgactgc | 600 |
| aacgacagca tgtgcagcac cagcgacgac accgtgagcg ccacccagct ggtgaagcag | 660 |
| ctgcagcaca ctcccagccc ctacagcagc cgtgagcg tgggcaccgc caagacctac | 720 |
| ggccagacca cgccgccac tcgccctggc cactgcggcc tggccgagaa gcagcactgc | 780 |
| gggcccgtga accctctgct gggcgccgcc accgccaccg gcaacaacaa gcgccgcaag | 840 |
| ctgtgcagcg gcaacaccac tcccatcatc cacctgaagg gcgaccgcaa cagcctgaag | 900 |

```
tgcctgcggt accgcctgcg caagcacagc gaccactacc gcgacatcag cagcacctgg    960
cactggaccg gcgccgggaa cgagaagacc ggcatcctga ccgtgaccta ccacagcgag   1020
acccagcgca ccaagttcct gaacaccgtg gccatccccg acagcgtgca gatcctggtg   1080
ggctacatga ccatgtaa                                                 1098

<210> SEQ ID NO 9
<211> LENGTH: 129
<212> TYPE: DNA
<213> ORGANISM: Artificial Sequence
<220> FEATURE:
<223> OTHER INFORMATION: Codon-Optimized HPV16 L1 fragment

<400> SEQUENCE: 9
atgagcctgt ggctgcccag cgaggccacc gtgtacctgc ctcccgtgcc cgtgagcaag     60
gtggtgagca ccgacgagta cgtggcccgc accaacatct actaccacgc cggcaccagc    120
cgcctgctg                                                            129

<210> SEQ ID NO 10
<211> LENGTH: 129
<212> TYPE: DNA
<213> ORGANISM: Artificial Sequence
<220> FEATURE:
<223> OTHER INFORMATION: Codon-Optimized HPV16 L1 fragment

<400> SEQUENCE: 10
cgcatccacc tgcccgaccc caacaagttc ggcttccccg acacaagctt ctacaacccc     60
gacacccagc gcctggtgtg ggcctgcgtg ggcgtggagg tgggccgcgg ccagcccctg    120
ggcgtgggc                                                            129

<210> SEQ ID NO 11
<211> LENGTH: 129
<212> TYPE: DNA
<213> ORGANISM: Artificial Sequence
<220> FEATURE:
<223> OTHER INFORMATION: Codon-Optimized HPV16 L1 fragment

<400> SEQUENCE: 11
gagtgcatca gcatggacta caagcagacc cagctgtgcc tgatcggctg caagcctccc     60
atcggcgagc actggggcaa gggcagcccc tgcaccaacg tggccgtgaa ccccggcgac    120
tgccctccc                                                            129

<210> SEQ ID NO 12
<211> LENGTH: 132
<212> TYPE: DNA
<213> ORGANISM: Artificial Sequence
<220> FEATURE:
<223> OTHER INFORMATION: Codon-Optimized HPV16 L1 fragment

<400> SEQUENCE: 12
gccaacaaga gcgaggtgcc cctggacatc tgcaccagca tctgcaagta ccccgactac     60
atcaagatgg tgagcgagcc ctacggcgac agcctgttct tctacctgcg ccgcgagcag    120
atgttcgtgc gc                                                        132

<210> SEQ ID NO 13
<211> LENGTH: 129
<212> TYPE: DNA
<213> ORGANISM: Artificial Sequence
<220> FEATURE:
<223> OTHER INFORMATION: Codon-Optimized HPV16 L1 fragment
```

<400> SEQUENCE: 13
gccagcagca actacttccc cactcccagc ggcagcatgg tgaccagcga cgcccaaatc    60
ttcaacaagc cctactggct gcagcgcgcc cagggccaca acaacggcat ctgctggggc   120
aaccagctg                                                          129

<210> SEQ ID NO 14
<211> LENGTH: 135
<212> TYPE: DNA
<213> ORGANISM: Artificial Sequence
<220> FEATURE:
<223> OTHER INFORMATION: Codon-Optimized HPV16 L1 fragment

<400> SEQUENCE: 14
gagtacctgc gccacggcga ggagtacgac ctgcagttca tcttccagct gtgcaagatc    60
accctgaccg ccgacgtgat gacctacatc cacagcatga acagcaccat cctggaggac   120
tggaacttcg gcctg                                                   135

<210> SEQ ID NO 15
<211> LENGTH: 135
<212> TYPE: DNA
<213> ORGANISM: Artificial Sequence
<220> FEATURE:
<223> OTHER INFORMATION: Codon-Optimized HPV16 L1 fragment

<400> SEQUENCE: 15
gctcccaagg aggatcccct gaagaagtac accttctggg aggtgaacct gaaggagaag    60
ttcagcgccg acctggacca gttcccccctg gccgcaagt tcctgctgca ggccggcctg   120
aaggccaagc ccaag                                                   135

<210> SEQ ID NO 16
<211> LENGTH: 135
<212> TYPE: DNA
<213> ORGANISM: Artificial Sequence
<220> FEATURE:
<223> OTHER INFORMATION: Codon-Optimized HPV16 L1 fragment

<400> SEQUENCE: 16
gttggggtcg gcaggtgga tgcggaacac gcggtactgc aggccgctca ccttgggcac    60
caggatcttg ttgttgttgg gcttcttgat ggggaagtag gggtggccca cggccagcag   120
gcggctggtg ccggc                                                   135

<210> SEQ ID NO 17
<211> LENGTH: 132
<212> TYPE: DNA
<213> ORGANISM: Artificial Sequence
<220> FEATURE:
<223> OTHER INFORMATION: Codon-Optimized HPV16 L1 fragment

<400> SEQUENCE: 17
cttgtagtcc atgctgatgc actcgcggtt gtccacgccg gcgttggcgg cgtaggcgct    60
ggcgttctcg gtgtcgtcca gcttgttcag caggggtgg ccgctgatgc ccacgcccag   120
gggctggccg cg                                                      132

<210> SEQ ID NO 18
<211> LENGTH: 129
<212> TYPE: DNA
<213> ORGANISM: Artificial Sequence
<220> FEATURE:

-continued

<223> OTHER INFORMATION: Codon-Optimized HPV16 L1 fragment

<400> SEQUENCE: 18
caggggcacc tcgctcttgt tggcctgcag ggtggtgaag tccatggcgc cgaagccggt 60
gtccaccatg tcgccgtcct ggatcacggt gttgatcagc tccaggggag ggcagtcgcc 120
ggggttcac 129

<210> SEQ ID NO 19
<211> LENGTH: 132
<212> TYPE: DNA
<213> ORGANISM: Artificial Sequence
<220> FEATURE:
<223> OTHER INFORMATION: Codon-Optimized HPV16 L1 fragment

<400> SEQUENCE: 19
gggagtgggg aagtagttgc tgctggccag gttggcggtg ctgccgctgc ccttgatgta 60
caggtcgtcg ggcacgttct cgcccacggc gccggcgcgg ttgaacaggt ggcgcacgaa 120
catctgctcg cg 132

<210> SEQ ID NO 20
<211> LENGTH: 144
<212> TYPE: DNA
<213> ORGANISM: Artificial Sequence
<220> FEATURE:
<223> OTHER INFORMATION: Codon-Optimized HPV16 L1 fragment

<400> SEQUENCE: 20
ctcctcgccg tggcgcaggt actccttgaa gttggtgttc ttgtaggtgg tctcgctggt 60
gctgatggcg gcgcacaggc tcatgttggt gctgcgggtg gtgtccacca cggtcacgaa 120
cagctggttg ccccagcaga tgcc 144

<210> SEQ ID NO 21
<211> LENGTH: 132
<212> TYPE: DNA
<213> ORGANISM: Artificial Sequence
<220> FEATURE:
<223> OTHER INFORMATION: Codon-Optimized HPV16 L1 fragment

<400> SEQUENCE: 21
cttcagggga tcctccttgg gagcgggagg ggtgtgcttc tggcaggcga tggcctggct 60
ggtcacgaag cggtaggtgt cctccagggt accgccggga gggggctgca ggccgaagtt 120
ccagtcctcc ag 132

<210> SEQ ID NO 22
<211> LENGTH: 123
<212> TYPE: DNA
<213> ORGANISM: Artificial Sequence
<220> FEATURE:
<223> OTHER INFORMATION: Codon-Optimized HPV16 L1 fragment

<400> SEQUENCE: 22
cactagagat ctgaattctt acagcttgcg cttcttgcgc ttggcggtgg tgctggtgct 60
gctggtggtg ggggtggcct tgcgcttgcc cagggtgaac ttgggcttgg ccttcaggcc 120
ggc 123

<210> SEQ ID NO 23
<211> LENGTH: 21
<212> TYPE: DNA
<213> ORGANISM: Artificial Sequence

```
<220> FEATURE:
<223> OTHER INFORMATION: Codon-Optimized HPV16 L1 fragment

<400> SEQUENCE: 23
cgcggccagc ccctgggcgt g                                              21

<210> SEQ ID NO 24
<211> LENGTH: 24
<212> TYPE: DNA
<213> ORGANISM: Artificial Sequence
<220> FEATURE:
<223> OTHER INFORMATION: Codon-Optimized HPV16 L1 fragment

<400> SEQUENCE: 24
gcccacgccc aggggctggc cgcg                                           24

<210> SEQ ID NO 25
<211> LENGTH: 21
<212> TYPE: DNA
<213> ORGANISM: Artificial Sequence
<220> FEATURE:
<223> OTHER INFORMATION: Codon-Optimized HPV16 L1 fragment

<400> SEQUENCE: 25
gccaacaaga gcgaggtgcc c                                              21

<210> SEQ ID NO 26
<211> LENGTH: 24
<212> TYPE: DNA
<213> ORGANISM: Artificial Sequence
<220> FEATURE:
<223> OTHER INFORMATION: Codon-Optimized HPV16 L1 fragment

<400> SEQUENCE: 26
caggggcacc tcgctcttgt tggc                                           24

<210> SEQ ID NO 27
<211> LENGTH: 23
<212> TYPE: DNA
<213> ORGANISM: Artificial Sequence
<220> FEATURE:
<223> OTHER INFORMATION: Codon-Optimized HPV16 L1 fragment

<400> SEQUENCE: 27
gccagcagca actacttccc cac                                            23

<210> SEQ ID NO 28
<211> LENGTH: 23
<212> TYPE: DNA
<213> ORGANISM: Artificial Sequence
<220> FEATURE:
<223> OTHER INFORMATION: Codon-Optimized HPV16 L1 fragment

<400> SEQUENCE: 28
gggagtgggg aagtagttgc tgc                                            23

<210> SEQ ID NO 29
<211> LENGTH: 24
<212> TYPE: DNA
<213> ORGANISM: Artificial Sequence
<220> FEATURE:
<223> OTHER INFORMATION: Codon-Optimized HPV16 L1 fragment

<400> SEQUENCE: 29
ctggaggact ggaacttcgg cctg                                           24
```

<210> SEQ ID NO 30
<211> LENGTH: 24
<212> TYPE: DNA
<213> ORGANISM: Artificial Sequence
<220> FEATURE:
<223> OTHER INFORMATION: Codon-Optimized HPV16 L1 fragment

<400> SEQUENCE: 30
caggccgaag ttccagtcct ccag                                          24

<210> SEQ ID NO 31
<211> LENGTH: 25
<212> TYPE: DNA
<213> ORGANISM: Artificial Sequence
<220> FEATURE:
<223> OTHER INFORMATION: Codon-Optimized HPV16 L1 fragment

<400> SEQUENCE: 31
cactagagat ctgaattctt acagc                                         25

<210> SEQ ID NO 32
<211> LENGTH: 38
<212> TYPE: DNA
<213> ORGANISM: Artificial Sequence
<220> FEATURE:
<223> OTHER INFORMATION: Codon-Optimized HPV16 L1 fragment

<400> SEQUENCE: 32
catctcagat ctgccaccat gagcctgtgg ctgcccag                           38

<210> SEQ ID NO 33
<211> LENGTH: 129
<212> TYPE: DNA
<213> ORGANISM: Artificial Sequence
<220> FEATURE:
<223> OTHER INFORMATION: Codon-Optimized HPV16 E1 fragment

<400> SEQUENCE: 33
atggccgacc ccgccggcac caacggcgag gagggcaccg gctgcaacgg ctggttctac    60
gtggaggccg tggtggagaa gaagaccggc gacgccatca gcgacgacga gaacgagaac   120
gacagcgac                                                          129

<210> SEQ ID NO 34
<211> LENGTH: 132
<212> TYPE: DNA
<213> ORGANISM: Artificial Sequence
<220> FEATURE:
<223> OTHER INFORMATION: Codon-Optimized HPV16 E1 fragment

<400> SEQUENCE: 34
gtgctgcttg gcctcctggg cggtgaacag ggcgtgggcg gtctcggtct cggcctgggt    60
caggtagtcg ttgtcgttca cgatgaagtc caccaggtcc tcgccggtgt cgctgtcgtt   120
ctcgttctcg tc                                                      132

<210> SEQ ID NO 35
<211> LENGTH: 132
<212> TYPE: DNA
<213> ORGANISM: Artificial Sequence
<220> FEATURE:
<223> OTHER INFORMATION: Codon-Optimized HPV16 E1 fragment

<400> SEQUENCE: 35
gcccaggagg ccaagcagca ccgcgacgcc gtgcaggtgc tgaagcgcaa gtacctgggc    60

```
agcccctga gcgacatcag cggctgcgtc gacaacaaca tcagccccg cctgaaggcc    120 atctgcatcg ag                                                       132

<210> SEQ ID NO 36
<211> LENGTH: 131
<212> TYPE: DNA
<213> ORGANISM: Artificial Sequence
<220> FEATURE:
<223> OTHER INFORMATION: Codon-Optimized HPV16 E1 fragment

<400> SEQUENCE: 36
ctcgtggcgg ccctccacct gcagcatctg ctgggtctcc acctcggtgt tgccgtagcc    60
gctgtcctcg ctctcgaaca ggcggcgctt ggcggcgcgg ctctgcttct cgatgcagat   120
ggccttcagg c                                                        131

<210> SEQ ID NO 37
<211> LENGTH: 132
<212> TYPE: DNA
<213> ORGANISM: Artificial Sequence
<220> FEATURE:
<223> OTHER INFORMATION: Codon-Optimized HPV16 E1 fragment

<400> SEQUENCE: 37
caggtggagg gccgccacga gaccgagacc ccctgcagcc agtacagcgg cggcagcggc    60
ggcggctgca gccagtacag cagcggcagc ggcggcgagg gcgtgagcga gcgccacacc   120
atctgccaga cc                                                       132

<210> SEQ ID NO 38
<211> LENGTH: 135
<212> TYPE: DNA
<213> ORGANISM: Artificial Sequence
<220> FEATURE:
<223> OTHER INFORMATION: Codon-Optimized HPV16 E1 fragment

<400> SEQUENCE: 38
cttgaagggg cgcaccagct cgctgaagct cacgccgtac agctccttga acttggccag    60
catggcggcc ttggcgttgc tggtcttcag cacgttcagg atgttggtca gagggtctg    120 gcagatggtg tggcg                                                    135

<210> SEQ ID NO 39
<211> LENGTH: 135
<212> TYPE: DNA
<213> ORGANISM: Artificial Sequence
<220> FEATURE:
<223> OTHER INFORMATION: Codon-Optimized HPV16 E1 fragment

<400> SEQUENCE: 39
gagctggtgc gccccttcaa gagcaacaag agcacctgct gcgactggtg catcgccgcc    60
ttcggcctga cccccagcat cgccgacagc atcaagaccc tgctgcagca gtactgcctg   120
tacctgcaca tccag                                                    135

<210> SEQ ID NO 40
<211> LENGTH: 136
<212> TYPE: DNA
<213> ORGANISM: Artificial Sequence
<220> FEATURE:
<223> OTHER INFORMATION: Codon-Optimized HPV16 E1 fragment

<400> SEQUENCE: 40
```

```
catggggctc acgcacagca gcttgctcag cagcttctcg atggtctcgc ggttcttgcc      60
gcacttgtag cgcaccagca gcagcaccac catgccccag ctgcaggcca ggctctggat     120
gtgcaggtac aggcag                                                     136
```

<210> SEQ ID NO 41
<211> LENGTH: 132
<212> TYPE: DNA
<213> ORGANISM: Artificial Sequence
<220> FEATURE:
<223> OTHER INFORMATION: Codon-Optimized HPV16 E1 fragment

<400> SEQUENCE: 41

```
ctgctgtgcg tgagccccat gtgcatgatg atcgagcctc ccaagcttcg cagcaccgcc      60
gccgccctgt actggtacaa gaccggcatc agcaacatca gcgaggtgta cggcgacacc     120
cccgagtgga tc                                                         132
```

<210> SEQ ID NO 42
<211> LENGTH: 129
<212> TYPE: DNA
<213> ORGANISM: Artificial Sequence
<220> FEATURE:
<223> OTHER INFORMATION: Codon-Optimized HPV16 E1 fragment

<400> SEQUENCE: 42

```
ggcgatctcg ctgtcgtcca cgatgtcgtt gtcgtaggcc actgcacca tctggctcag       60 ctcgaaggtg cagtcgttga agctgtgctg cagcacggtc tggcgctgga tccactcggg     120
ggtgtcgcc                                                             129
```

<210> SEQ ID NO 43
<211> LENGTH: 129
<212> TYPE: DNA
<213> ORGANISM: Artificial Sequence
<220> FEATURE:
<223> OTHER INFORMATION: Codon-Optimized HPV16 E1 fragment

<400> SEQUENCE: 43

```
gtggacgaca gcgagatcgc ctacaagtac gcccagctgg ccgacaccaa cagcaacgcc      60
agcgccttcc tgaagagcaa cagccaggcc aagatcgtga aggactgcgc caccatgtgc     120
cgccactac                                                             129
```

<210> SEQ ID NO 44
<211> LENGTH: 129
<212> TYPE: DNA
<213> ORGANISM: Artificial Sequence
<220> FEATURE:
<223> OTHER INFORMATION: Codon-Optimized HPV16 E1 fragment

<400> SEQUENCE: 44

```
gtagcgcagg aacatcacga tcttgcttgcg gtcgccgccg tcgtccacgc ggtcgcagcg      60
gtacttgatc cactggctca tgctcatctg cttcttctcg gcgcgcttgt agtggcggca     120
catggtggc                                                             129
```

<210> SEQ ID NO 45
<211> LENGTH: 129
<212> TYPE: DNA
<213> ORGANISM: Artificial Sequence
<220> FEATURE:
<223> OTHER INFORMATION: Codon-Optimized HPV16 E1 fragment

<400> SEQUENCE: 45

```
cagatcgtga tgttcctgcg ctaccagggc gtggaattca tgagcttcct gaccgccctg    60
aagcgcttcc tgcagggcat ccccaagaag aactgcatcc tgctgtacgg cgccgccaac   120
accgacaag                                                            129

<210> SEQ ID NO 46
<211> LENGTH: 130
<212> TYPE: DNA
<213> ORGANISM: Artificial Sequence
<220> FEATURE:
<223> OTHER INFORMATION: Codon-Optimized HPV16 E1 fragment

<400> SEQUENCE: 46
gccgatcttg gcgtcggcca ggggctgcag ccagaagtgg ctcttgctgt tcacgaagca    60
gatcacgctg ccctgcagga acttcatcag gctcatgccg acaggctct tgtcggtgtt   120 ggcggcgccg                                                           130

<210> SEQ ID NO 47
<211> LENGTH: 129
<212> TYPE: DNA
<213> ORGANISM: Artificial Sequence
<220> FEATURE:
<223> OTHER INFORMATION: Codon-Optimized HPV16 E1 fragment

<400> SEQUENCE: 47
ctggccgacg ccaagatcgg catgctggac gacgccaccg tgccctgctg gaactacatc    60
gacgacaacc tgcgcaacgc cctggacggc aacctggtga gcatggacgt gaagcaccgc   120
cccctggtg                                                            129

<210> SEQ ID NO 48
<211> LENGTH: 132
<212> TYPE: DNA
<213> ORGANISM: Artificial Sequence
<220> FEATURE:
<223> OTHER INFORMATION: Codon-Optimized HPV16 E1 fragment

<400> SEQUENCE: 48
gaactcgttg gggaaggtga acaccaccag gcggttgtgc aggtagggcc agcggctgtc    60
ggtgccggcg ttgatgttgc tggtgatcag caggggaggg cacttcagct gcaccagggg   120
gcggtgcttc ac                                                        132

<210> SEQ ID NO 49
<211> LENGTH: 126
<212> TYPE: DNA
<213> ORGANISM: Artificial Sequence
<220> FEATURE:
<223> OTHER INFORMATION: Codon-Optimized HPV16 E1 fragment

<400> SEQUENCE: 49
gtgttcacct tccccaacga gttccccttc gacgagaacg taacccccgt gtacgagctg    60
aacgacaaga actggaagag cttcttcagc cgcacctgga gccgcctgag cctgcacgag   120
gacgag                                                               126

<210> SEQ ID NO 50
<211> LENGTH: 105
<212> TYPE: DNA
<213> ORGANISM: Artificial Sequence
<220> FEATURE:
<223> OTHER INFORMATION: Codon-Optimized HPV16 E1 fragment
```

-continued

```
<400> SEQUENCE: 50
catgagagat ctttacaggg tgttggtgtt ctggccgctc acgcacttga aggtgggcag      60
gctgtcgccg tcgttctcct tgtcctcgtc ctcgtgcagg ctcag                    105

<210> SEQ ID NO 51
<211> LENGTH: 23
<212> TYPE: DNA
<213> ORGANISM: Artificial Sequence
<220> FEATURE:
<223> OTHER INFORMATION: Codon-Optimized HPV16 E1 fragment

<400> SEQUENCE: 51
gcctgaaggc catctgcatc gag                                             23

<210> SEQ ID NO 52
<211> LENGTH: 23
<212> TYPE: DNA
<213> ORGANISM: Artificial Sequence
<220> FEATURE:
<223> OTHER INFORMATION: Codon-Optimized HPV16 E1 fragment

<400> SEQUENCE: 52
ctcgatgcag atggccttca ggc                                             23

<210> SEQ ID NO 53
<211> LENGTH: 21
<212> TYPE: DNA
<213> ORGANISM: Artificial Sequence
<220> FEATURE:
<223> OTHER INFORMATION: Codon-Optimized HPV16 E1 fragment

<400> SEQUENCE: 53
gagctggtgc gccccttcaa g                                               21

<210> SEQ ID NO 54
<211> LENGTH: 21
<212> TYPE: DNA
<213> ORGANISM: Artificial Sequence
<220> FEATURE:
<223> OTHER INFORMATION: Codon-Optimized HPV16 E1 fragment

<400> SEQUENCE: 54
cttgaagggg cgcaccagct c                                               21

<210> SEQ ID NO 55
<211> LENGTH: 21
<212> TYPE: DNA
<213> ORGANISM: Artificial Sequence
<220> FEATURE:
<223> OTHER INFORMATION: Codon-Optimized HPV16 E1 fragment

<400> SEQUENCE: 55
ctgctgtgcg tgagccccat g                                               21

<210> SEQ ID NO 56
<211> LENGTH: 21
<212> TYPE: DNA
<213> ORGANISM: Artificial Sequence
<220> FEATURE:
<223> OTHER INFORMATION: Codon-Optimized HPV16 E1 fragment

<400> SEQUENCE: 56 catgggctc acgcacagca g                                                21
```

<210> SEQ ID NO 57
<211> LENGTH: 21
<212> TYPE: DNA
<213> ORGANISM: Artificial Sequence
<220> FEATURE:
<223> OTHER INFORMATION: Codon-Optimized HPV16 E1 fragment

<400> SEQUENCE: 57
gccaccatgt gccgccacta c                                    21

<210> SEQ ID NO 58
<211> LENGTH: 21
<212> TYPE: DNA
<213> ORGANISM: Artificial Sequence
<220> FEATURE:
<223> OTHER INFORMATION: Codon-Optimized HPV16 E1 fragment

<400> SEQUENCE: 58
gtagtggcgg cacatggtgg c                                    21

<210> SEQ ID NO 59
<211> LENGTH: 21
<212> TYPE: DNA
<213> ORGANISM: Artificial Sequence
<220> FEATURE:
<223> OTHER INFORMATION: Codon-Optimized HPV16 E1 fragment

<400> SEQUENCE: 59
ctggccgacg ccaagatcgg c                                    21

<210> SEQ ID NO 60
<211> LENGTH: 21
<212> TYPE: DNA
<213> ORGANISM: Artificial Sequence
<220> FEATURE:
<223> OTHER INFORMATION: Codon-Optimized HPV16 E1 fragment

<400> SEQUENCE: 60
gccgatcttg gcgtcggcca g                                    21

<210> SEQ ID NO 61
<211> LENGTH: 24
<212> TYPE: DNA
<213> ORGANISM: Artificial Sequence
<220> FEATURE:
<223> OTHER INFORMATION: Codon-Optimized HPV16 E1 fragment

<400> SEQUENCE: 61
gtgttcacct tccccaacga gttc                                 24

<210> SEQ ID NO 62
<211> LENGTH: 24
<212> TYPE: DNA
<213> ORGANISM: Artificial Sequence
<220> FEATURE:
<223> OTHER INFORMATION: Codon-Optimized HPV16 E1 fragment

<400> SEQUENCE: 62
gaactcgttg gggaaggtga acac                                 24

<210> SEQ ID NO 63
<211> LENGTH: 25
<212> TYPE: DNA
<213> ORGANISM: Artificial Sequence
<220> FEATURE:
<223> OTHER INFORMATION: Codon-Optimized HPV16 E1 fragment

```
<400> SEQUENCE: 63
catgagagat ctttacaggg tgttg                                          25

<210> SEQ ID NO 64
<211> LENGTH: 38
<212> TYPE: DNA
<213> ORGANISM: Artificial Sequence
<220> FEATURE:
<223> OTHER INFORMATION: Codon-Optimized HPV16 E1 fragment

<400> SEQUENCE: 64
catctcagat ctgccaccat ggccgacccc gccggcac                            38

<210> SEQ ID NO 65
<211> LENGTH: 99
<212> TYPE: DNA
<213> ORGANISM: Artificial Sequence
<220> FEATURE:
<223> OTHER INFORMATION: Codon-Optimized HPV16 E2 fragment

<400> SEQUENCE: 65
atggagaccc tgtgccagcg cctgaacgtg tgccaggaca agatcctgac ccactacgag    60
aacgacagca ccgacctgcg cgaccacatc gactactgg                           99

<210> SEQ ID NO 66
<211> LENGTH: 104
<212> TYPE: DNA
<213> ORGANISM: Artificial Sequence
<220> FEATURE:
<223> OTHER INFORMATION: Codon-Optimized HPV16 E2 fragment

<400> SEQUENCE: 66
ccaccaggtg gtgcccaccc tggccgtgag caagaacaag gccctgcagg ccgccgagct    60
gcagctgacc ctggagacga tctacaacag ccagtacagc aacg                    104

<210> SEQ ID NO 67
<211> LENGTH: 108
<212> TYPE: DNA
<213> ORGANISM: Artificial Sequence
<220> FEATURE:
<223> OTHER INFORMATION: Codon-Optimized HPV16 E2 fragment

<400> SEQUENCE: 67
ccggctgcat caagaagcac ggctacaccg tggaggtgca gttcgacggc gacatctgca    60
acaccatgca ctacaccaac tggacccaca tttacatctg tgaggagg               108

<210> SEQ ID NO 68
<211> LENGTH: 104
<212> TYPE: DNA
<213> ORGANISM: Artificial Sequence
<220> FEATURE:
<223> OTHER INFORMATION: Codon-Optimized HPV16 E2 fragment

<400> SEQUENCE: 68
cgtgcacgag gggatccgca cctacttcgt gcagttcaag gacgacgccg agaagtacag    60
caagaacaag gtgtgggagg tgcacgccgg aggccaggtg atcc                    104

<210> SEQ ID NO 69
<211> LENGTH: 110
<212> TYPE: DNA
<213> ORGANISM: Artificial Sequence
<220> FEATURE:
<223> OTHER INFORMATION: Codon-Optimized HPV16 E2 fragment
```

```
<400> SEQUENCE: 69
ggccaaccac agcgccgcca cccacaccaa ggccgtggcc ctgggcaccg aggagaccca    60
gaccacaatc cagcgccctc gcagcgagcc cgacaccggc aaccoctgcc              110

<210> SEQ ID NO 70
<211> LENGTH: 107
<212> TYPE: DNA
<213> ORGANISM: Artificial Sequence
<220> FEATURE:
<223> OTHER INFORMATION: Codon-Optimized HPV16 E2 fragment

<400> SEQUENCE: 70
gccacaaggg ccggatcaac tgcaacagca acaccacccc tatcgtgcac ctgaagggcg    60
acgccaacac cctgaagtgc ctgcggtacc gcttcaagaa gcactgc                 107

<210> SEQ ID NO 71
<211> LENGTH: 113
<212> TYPE: DNA
<213> ORGANISM: Artificial Sequence
<220> FEATURE:
<223> OTHER INFORMATION: Codon-Optimized HPV16 E2 fragment

<400> SEQUENCE: 71
ccagggtggg caccacctgg tggttgatgt gcttgaagcc catctcgcgg gccttgtagt    60
agatggcgca ggccaggcgc atgtgcttcc agtagtcgat gtggtcgcgc agg          113

<210> SEQ ID NO 72
<211> LENGTH: 101
<212> TYPE: DNA
<213> ORGANISM: Artificial Sequence
<220> FEATURE:
<223> OTHER INFORMATION: Codon-Optimized HPV16 E2 fragment

<400> SEQUENCE: 72
gccgtgcttc ttgatgcagc cggtaggggc ggtcaggtac acctccaggc tcacgtcctg    60
cagggtccac ttctcgttgc tgtactggct gttgtagatc g                       101

<210> SEQ ID NO 73
<211> LENGTH: 98
<212> TYPE: DNA
<213> ORGANISM: Artificial Sequence
<220> FEATURE:
<223> OTHER INFORMATION: Codon-Optimized HPV16 E2 fragment

<400> SEQUENCE: 73
ggtgcggatc ccctcgtgca cgtagtacag gccgtagtag tccacctggc cctccaccac    60
ggtcacgctg gcctcctcac agatgtaaat gtgggtcc                           98

<210> SEQ ID NO 74
<211> LENGTH: 110
<212> TYPE: DNA
<213> ORGANISM: Artificial Sequence
<220> FEATURE:
<223> OTHER INFORMATION: Codon-Optimized HPV16 E2 fragment

<400> SEQUENCE: 74
gggtggcggc gctgtggttg ccaggtgct ggcggatcgt ctcggggctg ctcacctcgt     60
tgctgctgaa cacgctggtg gggcacagga tcacctggcc tccggcgtgc               110

<210> SEQ ID NO 75
```

<211> LENGTH: 111
<212> TYPE: DNA
<213> ORGANISM: Artificial Sequence
<220> FEATURE:
<223> OTHER INFORMATION: Codon-Optimized HPV16 E2 fragment

<400> SEQUENCE: 75
gcagttgatc cggcccttgt ggctgctgtt gaaggcggtc aggatagggg cgctgtcgac    60
gctgtcgcgg tgcagcagct tggtggtgtg cagggggttg ccggtgtcgg g             111

<210> SEQ ID NO 76
<211> LENGTH: 110
<212> TYPE: DNA
<213> ORGANISM: Artificial Sequence
<220> FEATURE:
<223> OTHER INFORMATION: Codon-Optimized HPV16 E2 fragment

<400> SEQUENCE: 76
cgtaggtcag ggtcacgata gcgctcttgt gcttcacgtt gtggccggtc cagtgccagg    60
tgctgctcac ggcggtgtac agcttgcagt gcttcttgaa gcggtaccgc                110

<210> SEQ ID NO 77
<211> LENGTH: 111
<212> TYPE: DNA
<213> ORGANISM: Artificial Sequence
<220> FEATURE:
<223> OTHER INFORMATION: Codon-Optimized HPV16 E2 fragment

<400> SEQUENCE: 77
tttagatgct catgaagccg gtgctcacgg tgatggtctt ggggatcttc acctggctca    60
ggaactggtc gcgctgccac tcgctgtcgt aggtcagggt cacgatagcg c             111

<210> SEQ ID NO 78
<211> LENGTH: 50
<212> TYPE: DNA
<213> ORGANISM: Artificial Sequence
<220> FEATURE:
<223> OTHER INFORMATION: Codon-Optimized HPV16 E2 fragment

<400> SEQUENCE: 78
cgagctgata tcgaattcag atctgccacc atggagaccc tgtgccagcg                50

<210> SEQ ID NO 79
<211> LENGTH: 45
<212> TYPE: DNA
<213> ORGANISM: Artificial Sequence
<220> FEATURE:
<223> OTHER INFORMATION: Codon-Optimized HPV16 E2 fragment

<400> SEQUENCE: 79
ggttgcagat ctagactcga gtttagatgc tcatgaagcc ggtgc                     45

<210> SEQ ID NO 80
<211> LENGTH: 21
<212> TYPE: DNA
<213> ORGANISM: Artificial Sequence
<220> FEATURE:
<223> OTHER INFORMATION: Codon-Optimized HPV16 E2 fragment

<400> SEQUENCE: 80
ccggctgcat caagaagcac g                                               21

<210> SEQ ID NO 81
<211> LENGTH: 19

```
<212> TYPE: DNA
<213> ORGANISM: Artificial Sequence
<220> FEATURE:
<223> OTHER INFORMATION: Codon-Optimized HPV16 E2 fragment

<400> SEQUENCE: 81
ggccaaccac agcgccgcc                                                       19

<210> SEQ ID NO 82
<211> LENGTH: 21
<212> TYPE: DNA
<213> ORGANISM: Artificial Sequence
<220> FEATURE:
<223> OTHER INFORMATION: Codon-Optimized HPV16 E2 fragment

<400> SEQUENCE: 82
gccgtgcttc ttgatgcagc c                                                    21

<210> SEQ ID NO 83
<211> LENGTH: 17
<212> TYPE: DNA
<213> ORGANISM: Artificial Sequence
<220> FEATURE:
<223> OTHER INFORMATION: Codon-Optimized HPV16 E2 fragment

<400> SEQUENCE: 83
gggtggcggc gctgtgg                                                         17

<210> SEQ ID NO 84
<211> LENGTH: 22
<212> TYPE: DNA
<213> ORGANISM: Artificial Sequence
<220> FEATURE:
<223> OTHER INFORMATION: Codon-Optimized HPV16 E2 fragment

<400> SEQUENCE: 84
cgtaggtcag ggtcacgata gc                                                   22

<210> SEQ ID NO 85
<211> LENGTH: 109
<212> TYPE: DNA
<213> ORGANISM: Artificial Sequence
<220> FEATURE:
<223> OTHER INFORMATION: Codon-Optimized HPV16 E7 fragment

<400> SEQUENCE: 85
ggccggagat ctgatatcga attcgccacc atgcacggcg acacccccac cctgcacgag          60
tacatgctgg acctgcagcc cgagaccacc gacctgtacg gctacggcc                     109

<210> SEQ ID NO 86
<211> LENGTH: 106
<212> TYPE: DNA
<213> ORGANISM: Artificial Sequence
<220> FEATURE:
<223> OTHER INFORMATION: Codon-Optimized HPV16 E7 fragment

<400> SEQUENCE: 86
gccgagcccg accgcgccca ctacaacatc gtgaccttct gctgcaagtg cgacagcacc          60
ctgcgcctgt gcgtgcagag cacccacgtc gacatccgca ccctgg                        106

<210> SEQ ID NO 87
<211> LENGTH: 96
<212> TYPE: DNA
<213> ORGANISM: Artificial Sequence
<220> FEATURE:
```

```
<223> OTHER INFORMATION: Codon-Optimized HPV16 E7 fragment

<400> SEQUENCE: 87
gggcgcggtc gggctcggcc tggccggcgg ggccgtcgat ctcgtcctct tcctcgctgc      60
tgtcgttcag ctggccgtag ccgtacaggt cggtgg                               96

<210> SEQ ID NO 88
<211> LENGTH: 106
<212> TYPE: DNA
<213> ORGANISM: Artificial Sequence
<220> FEATURE:
<223> OTHER INFORMATION: Codon-Optimized HPV16 E7 fragment

<400> SEQUENCE: 88
ccgcggcaga tctagactcg agtttagggc ttctggctgc agattgggca cacgattccc      60
agggtgccca tcagcaggtc ctccagggtg cggatgtcga cgtggg                    106

<210> SEQ ID NO 89
<211> LENGTH: 25
<212> TYPE: DNA
<213> ORGANISM: Artificial Sequence
<220> FEATURE:
<223> OTHER INFORMATION: Codon-Optimized HPV16 E7 fragment

<400> SEQUENCE: 89
ggccggagat ctgatatcga attcg                                           25

<210> SEQ ID NO 90
<211> LENGTH: 20
<212> TYPE: DNA
<213> ORGANISM: Artificial Sequence
<220> FEATURE:
<223> OTHER INFORMATION: Codon-Optimized HPV16 E7 fragment

<400> SEQUENCE: 90
ccgcggcaga tctagactcg                                                 20

<210> SEQ ID NO 91
<211> LENGTH: 105
<212> TYPE: DNA
<213> ORGANISM: Artificial Sequence
<220> FEATURE:
<223> OTHER INFORMATION: Codon-Optimized HPV6a E7 fragment

<400> SEQUENCE: 91
gtcacagatc tgatatcgaa ttccaccatg cacggccgcc acgtgaccct gaaggacatc      60
gtgctggacc tgcagcctcc cgaccccgtg ggcctgcact gctac                     105

<210> SEQ ID NO 92
<211> LENGTH: 105
<212> TYPE: DNA
<213> ORGANISM: Artificial Sequence
<220> FEATURE:
<223> OTHER INFORMATION: Codon-Optimized HPV6a E7 fragment

<400> SEQUENCE: 92
ctggaagtgc tgcttcaggg gctggctgtc ctggccgtcc acctcgtcca cctcgtcctc      60
gctgctgtcc accagctgct cgtagcagtg caggcccacg ggtc                      105

<210> SEQ ID NO 93
<211> LENGTH: 107
<212> TYPE: DNA
<213> ORGANISM: Artificial Sequence
```

<220> FEATURE:
<223> OTHER INFORMATION: Codon-Optimized HPV6a E7 fragment

<400> SEQUENCE: 93 ccagccctg aagcagcact tccagatcgt gacctgctgc tgcggctgcg acagcaacgt    60
gcgcctggtg gtgcagtgca ccgagaccga catccgcgag gtgcagc                107

<210> SEQ ID NO 94
<211> LENGTH: 102
<212> TYPE: DNA
<213> ORGANISM: Artificial Sequence
<220> FEATURE:
<223> OTHER INFORMATION: Codon-Optimized HPV6a E7 fragment

<400> SEQUENCE: 94
cagtcagatc tagagatatc tttaggtctt gggagcgcag atggggcaca cgatgttcag    60
ggtacccagc aggagctgct gcacctcgcg gatgtcggtc tc                      102

<210> SEQ ID NO 95
<211> LENGTH: 24
<212> TYPE: DNA
<213> ORGANISM: Artificial Sequence
<220> FEATURE:
<223> OTHER INFORMATION: PCR Primer

<400> SEQUENCE: 95
gtcacagatc tgatatcgaa ttcc                                           24

<210> SEQ ID NO 96
<211> LENGTH: 26
<212> TYPE: DNA
<213> ORGANISM: Artificial Sequence
<220> FEATURE:
<223> OTHER INFORMATION: PCR Primer

<400> SEQUENCE: 96
cagtcagatc tagagatatc tttagg                                         26

<210> SEQ ID NO 97
<211> LENGTH: 109
<212> TYPE: DNA
<213> ORGANISM: Artificial Sequence
<220> FEATURE:
<223> OTHER INFORMATION: Codon-Optimized HPV18 E7 fragment

<400> SEQUENCE: 97
gtcacagatc tgatatcgaa ttccaccatg cacggcccca aggccaccct gcaggacatc    60
gtgctgcacc tggagcccca gaacgagatc ccgtggacc tgctgtgcc                109

<210> SEQ ID NO 98
<211> LENGTH: 111
<212> TYPE: DNA
<213> ORGANISM: Artificial Sequence
<220> FEATURE:
<223> OTHER INFORMATION: Codon-Optimized HPV18 E7 fragment

<400> SEQUENCE: 98
gggctcggcc ctgcgagcgg gcaggtgctg gtggttcacg ccgtcgatct cgtcgttctc    60
ctcctcgctg tcgctcagct gctcgtggca cagcaggtcc acgggatct c              111

<210> SEQ ID NO 99
<211> LENGTH: 108
<212> TYPE: DNA

<213> ORGANISM: Artificial Sequence
<220> FEATURE:
<223> OTHER INFORMATION: Codon-Optimized HPV18 E7 fragment

<400> SEQUENCE: 99

```
gcccgctcgc agggccgagc cccagcgcca caccatgctg tgcatgtgct gcaagtgcga      60
ggcccgcatc gagctggtgg tggagagcag cgctgacgac ctgcgcgc                  108
```

<210> SEQ ID NO 100
<211> LENGTH: 109
<212> TYPE: DNA
<213> ORGANISM: Artificial Sequence
<220> FEATURE:
<223> OTHER INFORMATION: Codon-Optimized HPV18 E7 fragment

<400> SEQUENCE: 100

```
cagtcagatc tagagatatc tttactgctg gctggcgcac caggggcaca cgaagctcag      60
ggtgttcagg aacagctgct ggaaggcgcg caggtcgtca gcgctgctc                 109
```

<210> SEQ ID NO 101
<211> LENGTH: 26
<212> TYPE: DNA
<213> ORGANISM: Artificial Sequence
<220> FEATURE:
<223> OTHER INFORMATION: PCR Fragment

<400> SEQUENCE: 101

```
gtcacagatc tgatatcgaa ttccac                                           26
```

<210> SEQ ID NO 102
<211> LENGTH: 27
<212> TYPE: DNA
<213> ORGANISM: Artificial Sequence
<220> FEATURE:
<223> OTHER INFORMATION: PCR Fragment

<400> SEQUENCE: 102

```
cagtcagatc tagagatatc tttactg                                          27
```

<210> SEQ ID NO 103
<211> LENGTH: 90
<212> TYPE: DNA
<213> ORGANISM: Artificial Sequence
<220> FEATURE:
<223> OTHER INFORMATION: Codon-Optimized HPV6 E2 fragment

<400> SEQUENCE: 103

```
gaattcagat ctgatatcac catggaggcc atcgccaagc gcctggacgc ctgccaggag      60
cagctgctgg agctgtacga ggagaacagc                                       90
```

<210> SEQ ID NO 104
<211> LENGTH: 92
<212> TYPE: DNA
<213> ORGANISM: Artificial Sequence
<220> FEATURE:
<223> OTHER INFORMATION: Codon-Optimized HPV6 E2 fragment

<400> SEQUENCE: 104

```
ccttgtacag cagcacgctc tcgtggcgca tgcacttcca gtgcagcacg tgcttgtgca      60
ggtcggtgct gttctcctcg tacagctcca gc                                    92
```

<210> SEQ ID NO 105
<211> LENGTH: 96

```
<212> TYPE: DNA
<213> ORGANISM: Artificial Sequence
<220> FEATURE:
<223> OTHER INFORMATION: Codon-Optimized HPV6 E2 fragment

<400> SEQUENCE: 105
ccacgagagc gtgctgctgt acaaggccaa gcagatgggc ctgagccaca tcggcatgca      60
ggtggtgcct cctctgaagg tgagcgaggc caaggg                                96

<210> SEQ ID NO 106
<211> LENGTH: 103
<212> TYPE: DNA
<213> ORGANISM: Artificial Sequence
<220> FEATURE:
<223> OTHER INFORMATION: Codon-Optimized HPV6 E2 fragment

<400> SEQUENCE: 106
gcagggtcca gggctccatg ctgtactcgg tgcgcagcag gctctcgagg tgcatctgca      60
tctcgatggc gttgtggccc ttggcctcgc tcaccttcag agg                        103

<210> SEQ ID NO 107
<211> LENGTH: 98
<212> TYPE: DNA
<213> ORGANISM: Artificial Sequence
<220> FEATURE:
<223> OTHER INFORMATION: Codon-Optimized HPV6 E2 fragment

<400> SEQUENCE: 107
cgagtacagc atggagccct ggaccctgca ggagaccagc tacgagatgt ggcagacccc      60
tcccaagcgc tgcttcaaga agcgcggcaa gaccgtgg                              98

<210> SEQ ID NO 108
<211> LENGTH: 102
<212> TYPE: DNA
<213> ORGANISM: Artificial Sequence
<220> FEATURE:
<223> OTHER INFORMATION: Codon-Optimized HPV6 E2 fragment

<400> SEQUENCE: 108
cgttgtcctg cacgtacacg tcggtccaca ccacgtagtc catggtgttg ttggcgcagc      60
cgtcgaactt cacctccacg gtcttgccgc gcttcttgaa gc                         102

<210> SEQ ID NO 109
<211> LENGTH: 102
<212> TYPE: DNA
<213> ORGANISM: Artificial Sequence
<220> FEATURE:
<223> OTHER INFORMATION: Codon-Optimized HPV6 E2 fragment

<400> SEQUENCE: 109
ccgacgtgta cgtgcaggac aacgacacct gggtgaaggt gcacagcatg gtggacgcca      60
agggcatcta ctacacctgt ggccagttca agacctacta cg                         102

<210> SEQ ID NO 110
<211> LENGTH: 92
<212> TYPE: DNA
<213> ORGANISM: Artificial Sequence
<220> FEATURE:
<223> OTHER INFORMATION: Codon-Optimized HPV6 E2 fragment

<400> SEQUENCE: 110
gctgccgtag cacacctccc agtgcttggt gctgccgtac ttctcggcct ccttcacgaa      60
```
gttcacgtag taggtcttga actggccaca gg 92

<210> SEQ ID NO 111
<211> LENGTH: 94
<212> TYPE: DNA
<213> ORGANISM: Artificial Sequence
<220> FEATURE:
<223> OTHER INFORMATION: Codon-Optimized HPV6 E2 fragment

<400> SEQUENCE: 111
gcactgggag gtgtgctacg gcagcaccgt gatctgcagc cccgctagcg tgagcagcac 60
cacccaggag gtgagcatcc ccgagagcac cacc 94

<210> SEQ ID NO 112
<211> LENGTH: 97
<212> TYPE: DNA
<213> ORGANISM: Artificial Sequence
<220> FEATURE:
<223> OTHER INFORMATION: Codon-Optimized HPV6 E2 fragment

<400> SEQUENCE: 112
gcgaggaggg gtctgcacgg cgtcctcctt ggtgctgctg ctcaccaggg tgctggtctg 60
ggcgggagtg taggtggtgc tctcggggat gctcacc 97

<210> SEQ ID NO 113
<211> LENGTH: 97
<212> TYPE: DNA
<213> ORGANISM: Artificial Sequence
<220> FEATURE:
<223> OTHER INFORMATION: Codon-Optimized HPV6 E2 fragment

<400> SEQUENCE: 113
ggacgccgtg cagacccctc ctcgcaagcg cgcccgcggc gtgcagcaga gcccctgcaa 60
cgccctgtgc gtggcccaca tcggccccgt ggacagc 97

<210> SEQ ID NO 114
<211> LENGTH: 94
<212> TYPE: DNA
<213> ORGANISM: Artificial Sequence
<220> FEATURE:
<223> OTHER INFORMATION: Codon-Optimized HPV6 E2 fragment

<400> SEQUENCE: 114
ggcgctgctg ttgctgttgt tgcggcgctg gtgctggtcg tggttgttgg tgatcaggtt 60
gtggttgccg ctgtccacgg ggccgatgtg ggcc 94

<210> SEQ ID NO 115
<211> LENGTH: 95
<212> TYPE: DNA
<213> ORGANISM: Artificial Sequence
<220> FEATURE:
<223> OTHER INFORMATION: Codon-Optimized HPV6 E2 fragment

<400> SEQUENCE: 115
ccgcaacaac agcaacagca cgccactcc catcgtgcag ttccagggcg agagcaactg 60
cctgaagtgc ttccgctacc gcctgaacga tcgcc 95

<210> SEQ ID NO 116
<211> LENGTH: 96
<212> TYPE: DNA
<213> ORGANISM: Artificial Sequence
<220> FEATURE:
<223> OTHER INFORMATION: Codon-Optimized HPV6 E2 fragment

```
<400> SEQUENCE: 116
cgtgcttgtg gggagccttg ctgctggccc agtgccaggt gctgctgatc aggtcgaaca      60
ggtggcggtg gcgatcgttc aggcggtagc ggaagc                               96

<210> SEQ ID NO 117
<211> LENGTH: 95
<212> TYPE: DNA
<213> ORGANISM: Artificial Sequence
<220> FEATURE:
<223> OTHER INFORMATION: Codon-Optimized HPV6 E2 fragment

<400> SEQUENCE: 117
gcagcaaggc tccccacaag cacgccatcg tgaccgtgac ctacgacagc gaggagcagc      60
gccagcagtt cctggacgtg gtgaagatcc ctccc                                95

<210> SEQ ID NO 118
<211> LENGTH: 96
<212> TYPE: DNA
<213> ORGANISM: Artificial Sequence
<220> FEATURE:
<223> OTHER INFORMATION: Codon-Optimized HPV6 E2 fragment

<400> SEQUENCE: 118
ctcgagagat ctcccgggtc tagagcttac agcaggtgca ggctcatgaa gcccagcttg      60
tggctgatgg tgggagggat cttcaccacg tccagg                               96

<210> SEQ ID NO 119
<211> LENGTH: 25
<212> TYPE: DNA
<213> ORGANISM: Artificial Sequence
<220> FEATURE:
<223> OTHER INFORMATION: Codon-Optimized HPV6 E2 fragment

<400> SEQUENCE: 119
gaattcagat ctgatatcac catgg                                           25

<210> SEQ ID NO 120
<211> LENGTH: 21
<212> TYPE: DNA
<213> ORGANISM: Artificial Sequence
<220> FEATURE:
<223> OTHER INFORMATION: Codon-Optimized HPV6 E2 fragment

<400> SEQUENCE: 120
gcagggtcca gggctccatg c                                               21

<210> SEQ ID NO 121
<211> LENGTH: 25
<212> TYPE: DNA
<213> ORGANISM: Artificial Sequence
<220> FEATURE:
<223> OTHER INFORMATION: Codon-Optimized HPV6 E2 fragment

<400> SEQUENCE: 121
cgagtacagc atggagccct ggacc                                           25

<210> SEQ ID NO 122
<211> LENGTH: 25
<212> TYPE: DNA
<213> ORGANISM: Artificial Sequence
<220> FEATURE:
<223> OTHER INFORMATION: Codon-Optimized HPV6 E2 fragment
```

```
<400> SEQUENCE: 122
gctgccgtag cacacctccc agtgc                                          25

<210> SEQ ID NO 123
<211> LENGTH: 21
<212> TYPE: DNA
<213> ORGANISM: Artificial Sequence
<220> FEATURE:
<223> OTHER INFORMATION: Codon-Optimized HPV6 E2 fragment

<400> SEQUENCE: 123
gcactgggag gtgtgctacg g                                              21

<210> SEQ ID NO 124
<211> LENGTH: 23
<212> TYPE: DNA
<213> ORGANISM: Artificial Sequence
<220> FEATURE:
<223> OTHER INFORMATION: Codon-Optimized HPV6 E2 fragment

<400> SEQUENCE: 124
ggcgctgctg ttgctgttgt tgc                                            23

<210> SEQ ID NO 125
<211> LENGTH: 22
<212> TYPE: DNA
<213> ORGANISM: Artificial Sequence
<220> FEATURE:
<223> OTHER INFORMATION: Codon-Optimized HPV6 E2 fragment

<400> SEQUENCE: 125
ccgcaacaac agcaacagca gc                                             22

<210> SEQ ID NO 126
<211> LENGTH: 26
<212> TYPE: DNA
<213> ORGANISM: Artificial Sequence
<220> FEATURE:
<223> OTHER INFORMATION: Codon-Optimized HPV6 E2 fragment

<400> SEQUENCE: 126
ctcgagagat ctcccgggtc tagagc                                         26

<210> SEQ ID NO 127
<211> LENGTH: 97
<212> TYPE: DNA
<213> ORGANISM: Artificial Sequence
<220> FEATURE:
<223> OTHER INFORMATION: Codon-Optimized HPV18 E2 fragment

<400> SEQUENCE: 127
gaattcagat ctgatatcac catgcagact cccaaggaga ccctgagcga gcgcctgagc    60
gccctgcagg acaagatcat cgaccactac gagaacg                             97

<210> SEQ ID NO 128
<211> LENGTH: 98
<212> TYPE: DNA
<213> ORGANISM: Artificial Sequence
<220> FEATURE:
<223> OTHER INFORMATION: Codon-Optimized HPV18 E2 fragment

<400> SEQUENCE: 128
cgaagaagat ggcgttctcc cagcggatca gctgccagta ctggatctgg ctgtcgatgt    60
ccttgctgtc gttctcgtag tggtcgatga tcttgtcc                            98
```

<210> SEQ ID NO 129
<211> LENGTH: 94
<212> TYPE: DNA
<213> ORGANISM: Artificial Sequence
<220> FEATURE:
<223> OTHER INFORMATION: Codon-Optimized HPV18 E2 fragment

<400> SEQUENCE: 129
ccgctgggag aacgccatct tcttcgccgc tcgcgagcac gggatccaga ccctgaacca    60
ccaggtggtg cccgcctaca acatcagcaa gagc                                94

<210> SEQ ID NO 130
<211> LENGTH: 94
<212> TYPE: DNA
<213> ORGANISM: Artificial Sequence
<220> FEATURE:
<223> OTHER INFORMATION: Codon-Optimized HPV18 E2 fragment

<400> SEQUENCE: 130
cctcggtctt gtaggcgctc tgggccaggc cctgcagggc catctgcagc tcgatggcct    60
tgtgggcctt gctcttgctg atgttgtagg cggg                                94

<210> SEQ ID NO 131
<211> LENGTH: 91
<212> TYPE: DNA
<213> ORGANISM: Artificial Sequence
<220> FEATURE:
<223> OTHER INFORMATION: Codon-Optimized HPV18 E2 fragment

<400> SEQUENCE: 131
cccagagcgc ctacaagacc gaggactgga ccctgcagga cacctgcgag gagctgtgga    60
acaccgagcc cacccactgc ttcaagaagg g                                   91

<210> SEQ ID NO 132
<211> LENGTH: 94
<212> TYPE: DNA
<213> ORGANISM: Artificial Sequence
<220> FEATURE:
<223> OTHER INFORMATION: Codon-Optimized HPV18 E2 fragment

<400> SEQUENCE: 132
gctgtcccag gccacgtagt tcatgcagtt gtccttgttg ccgtcgaagt acacctgcac    60
ggtctggcct cccttcttga agcagtgggt gggc                                94

<210> SEQ ID NO 133
<211> LENGTH: 90
<212> TYPE: DNA
<213> ORGANISM: Artificial Sequence
<220> FEATURE:
<223> OTHER INFORMATION: Codon-Optimized HPV18 E2 fragment

<400> SEQUENCE: 133
gcatgaacta cgtggcctgg acagcgtgt actacatgac cgacgccggc acctgggaca    60
agaccgccac ctgcgtgagc caccgcggcc                                     90

<210> SEQ ID NO 134
<211> LENGTH: 92
<212> TYPE: DNA
<213> ORGANISM: Artificial Sequence
<220> FEATURE:
<223> OTHER INFORMATION: Codon-Optimized HPV18 E2 fragment

```
<400> SEQUENCE: 134
ccgtacttct cgcactcgct cttgaactcg atgtagaagg tgttgtagcc ctccttcacg    60
tagtacaggc cgcggtggct cacgcaggtg gc                                  92

<210> SEQ ID NO 135
<211> LENGTH: 94
<212> TYPE: DNA
<213> ORGANISM: Artificial Sequence
<220> FEATURE:
<223> OTHER INFORMATION: Codon-Optimized HPV18 E2 fragment

<400> SEQUENCE: 135
cgagttcaag agcgagtgcg agaagtacgg caacaccggc acctgggagg tgcacttcgg    60
caacaacgtg atcgactgca cgacagcat gtgc                                 94

<210> SEQ ID NO 136
<211> LENGTH: 100
<212> TYPE: DNA
<213> ORGANISM: Artificial Sequence
<220> FEATURE:
<223> OTHER INFORMATION: Codon-Optimized HPV18 E2 fragment

<400> SEQUENCE: 136
gctgtagggg ctgggagtgt gctgcagctg cttcaccagc tgggtggcgc tcacggtgtc    60
gtcgctggtg ctgcacatgc tgtcgttgca gtcgatcacg                         100

<210> SEQ ID NO 137
<211> LENGTH: 93
<212> TYPE: DNA
<213> ORGANISM: Artificial Sequence
<220> FEATURE:
<223> OTHER INFORMATION: Codon-Optimized HPV18 E2 fragment

<400> SEQUENCE: 137
gcacactccc agcccctaca gcagcaccgt gagcgtgggc accgccaaga cctacggcca    60
gaccagcgcc gccactcgcc ctggccactg cgg                                 93

<210> SEQ ID NO 138
<211> LENGTH: 96
<212> TYPE: DNA
<213> ORGANISM: Artificial Sequence
<220> FEATURE:
<223> OTHER INFORMATION: Codon-Optimized HPV18 E2 fragment

<400> SEQUENCE: 138
gcttgttgtt gccggtggcg gtggcggcgc ccagcagagg gttcacgggc cgcagtgct    60 gcttctcggc caggccgcag tggccagggc gagtgg                              96

<210> SEQ ID NO 139
<211> LENGTH: 97
<212> TYPE: DNA
<213> ORGANISM: Artificial Sequence
<220> FEATURE:
<223> OTHER INFORMATION: Codon-Optimized HPV18 E2 fragment

<400> SEQUENCE: 139
gccaccgcca ccggcaacaa caagcgccgc aagctgtgca gcggcaacac cactcccatc    60
atccacctga agggcgaccg caacagcctg aagtgcc                             97

<210> SEQ ID NO 140
<211> LENGTH: 97
```

```
<212> TYPE: DNA
<213> ORGANISM: Artificial Sequence
<220> FEATURE:
<223> OTHER INFORMATION: Codon-Optimized HPV18 E2 fragment

<400> SEQUENCE: 140
ggcgccggtc cagtgccagg tgctgctgat gtcgcggtag tggtcgctgt gcttgcgcag     60
gcggtaccgc aggcacttca ggctgttgcg gtcgccc                              97

<210> SEQ ID NO 141
<211> LENGTH: 99
<212> TYPE: DNA
<213> ORGANISM: Artificial Sequence
<220> FEATURE:
<223> OTHER INFORMATION: Codon-Optimized HPV18 E2 fragment

<400> SEQUENCE: 141
gcacctggca ctggaccggc gccgggaacg agaagaccgg catcctgacc gtgacctacc     60
acagcgagac ccagcgcacc aagttcctga acaccgtgg                            99

<210> SEQ ID NO 142
<211> LENGTH: 98
<212> TYPE: DNA
<213> ORGANISM: Artificial Sequence
<220> FEATURE:
<223> OTHER INFORMATION: Codon-Optimized HPV18 E2 fragment

<400> SEQUENCE: 142
ctcgagagat ctcccgggtc tagagcttac atggtcatgt agcccaccag gatctgcacg     60
ctgtcgggga tggccacggt gttcaggaac ttggtgcg                             98

<210> SEQ ID NO 143
<211> LENGTH: 25
<212> TYPE: DNA
<213> ORGANISM: Artificial Sequence
<220> FEATURE:
<223> OTHER INFORMATION: Codon-Optimized HPV18 E2 fragment

<400> SEQUENCE: 143
gaattcagat ctgatatcac catgc                                           25

<210> SEQ ID NO 144
<211> LENGTH: 23
<212> TYPE: DNA
<213> ORGANISM: Artificial Sequence
<220> FEATURE:
<223> OTHER INFORMATION: Codon-Optimized HPV18 E2 fragment

<400> SEQUENCE: 144
cctcggtctt gtaggcgctc tgg                                             23

<210> SEQ ID NO 145
<211> LENGTH: 21
<212> TYPE: DNA
<213> ORGANISM: Artificial Sequence
<220> FEATURE:
<223> OTHER INFORMATION: Codon-Optimized HPV18 E2 fragment

<400> SEQUENCE: 145
cccagagcgc ctacaagacc g                                               21

<210> SEQ ID NO 146
<211> LENGTH: 21
<212> TYPE: DNA
```

```
<213> ORGANISM: Artificial Sequence
<220> FEATURE:
<223> OTHER INFORMATION: Codon-Optimized HPV18 E2 fragment

<400> SEQUENCE: 146
ccgtacttct cgcactcgct c                                        21

<210> SEQ ID NO 147
<211> LENGTH: 20
<212> TYPE: DNA
<213> ORGANISM: Artificial Sequence
<220> FEATURE:
<223> OTHER INFORMATION: Codon-Optimized HPV18 E2 fragment

<400> SEQUENCE: 147
cgagttcaag agcgagtgcg                                          20

<210> SEQ ID NO 148
<211> LENGTH: 21
<212> TYPE: DNA
<213> ORGANISM: Artificial Sequence
<220> FEATURE:
<223> OTHER INFORMATION: Codon-Optimized HPV18 E2 fragment

<400> SEQUENCE: 148
gcttgttgtt gccggtggcg g                                        21

<210> SEQ ID NO 149
<211> LENGTH: 25
<212> TYPE: DNA
<213> ORGANISM: Artificial Sequence
<220> FEATURE:
<223> OTHER INFORMATION: Codon-Optimized HPV18 E2 fragment

<400> SEQUENCE: 149
gccaccgcca ccggcaacaa caagc                                    25

<210> SEQ ID NO 150
<211> LENGTH: 26
<212> TYPE: DNA
<213> ORGANISM: Artificial Sequence
<220> FEATURE:
<223> OTHER INFORMATION: Codon-Optimized HPV18 E2 fragment

<400> SEQUENCE: 150
ctcgagagat ctcccgggtc tagagc                                   26
```

SYNTHETIC HUMAN PAPILLOMA VIRUS GENES

CROSS-REFERENCE TO RELATED APPLICATIONS

This application is a continuation of U.S. Ser. No. 09/642,405, filed Aug. 21, 2000, now U.S. Pat. No. 7,001,995, which claims priority to U.S. Provisional Application Ser. No. 60/150,728, filed Aug. 25, 1999, now expired, and U.S. Provisional Application Ser. No. 60/210,143, filed Jun. 7, 2000, now expired.

FIELD OF THE INVENTION

This invention relates to human papillomavirus (HPV) genes which have been codon-optimized for expression in a human cellular environment, and their use with adenoviral vectors and or plasmid vectors as vaccines.

BACKGROUND OF THE INVENTION

*Papillomavirus* infections occur in a variety of animals, including humans, sheep, dogs, cats, rabbits, snakes, monkeys and cows. Papillomaviruses infect epithelial cells, generally inducing benign epithelial or fibroepithelial tumors at the site of infection. Papillomaviruses are species specific infective agents; a human papillomavirus cannot infect a non-human.

Papillomaviruses are small (50–60 nm), nonenveloped, icosahedral DNA viruses what encode up to eight early and two late genes. The open reading frames (ORFs) of the virus are designated E1 to E7 and L1 and L2, where "E" denotes early and "L" denotes late. L1 and L2 code for virus capsid proteins. The early genes are associated with functions such as viral replication and cellular transformation.

In humans, different HPV types cause distinct diseases, ranging from benign warts (for examples HPV types 1, 2, 3) to highly invasive genital and anal carcinomas (HPV types 16 and 18). At present there is not a satisfactory therapeutic regimen for these diseases.

Immunological studies in animals have shown that the production of neutralizing antibodies to papillomavirus antigens prevents infection with the homologous virus. However, development of a vaccine has been hindered by the difficulties associated with culture of the papillomavirus in vitro.

Vaccination is an effective form of disease prevention and has proven successful against several types of viral infection. However, to date, attempts to generate an effective HPV vaccine have not been entirely successful.

SUMMARY OF THE INVENTION

This invention relates to oligonucleotides which encode a human papillomavirus (HPV) protein which has been codon-optimized for efficient expression in a host cell; preferably the oligonucleotides are DNA. In one embodiment, the polynucleotides encode a protein which retains its wild-type amino acid sequence. In an alternate embodiment, the polynucleotides encode a mutated form of a HPV protein which has reduced protein function as compared to wild-type protein, but which maintains immunogenicity. This invention also relates to the mutated HPV proteins so encoded.

In preferred embodiments, the protein is selected from the group consisting of: L1, L2, E1, E2, E4, E5, E6 and E7 proteins. Particularly preferred are L1, L2, E2, and E7 proteins.

Another aspect of this invention is a vector carrying the polynucleotides encoding a codon-optimized HPV protein. Yet another aspect of this invention are host cells containing these vectors.

In a preferred embodiment, the vector is an adenoviral vector. In a particularly preferred embodiment, the adenoviral vector is a vaccine vector comprising an adenoviral genome with a deletion in the E1 region, and an insert in the E1 region, wherein the insert comprises an expression cassette comprising:

a) a polynucleotide encoding an HPV protein selected from the group consisting of L1, E1, E2, and E7 proteins or mutant forms thereof, wherein the polynucleotide is codon-optimized for expression in a human host cell; and b) a promoter operably linked to the polynucleotide.

Another type of vector which is envisioned by this invention is a shuttle plasmid vector comprising a plasmid portion and an adenoviral portion, the adenoviral portion comprising: an adenoviral genome with a deletion in the E1 region, and an insert in the E1 region, wherein the insert comprises an expression cassette comprising:

a) a polynucleotide encoding an HPV protein selected from the group consisting of L1, E1, E2, and E7 proteins, wherein the polynucleotide is codon-optimized for expression in a human host cell; and b) a promoter operably linked to the polynucleotide.

This invention also is directed to plasmid vaccine vectors, which comprise a plasmid portion and an expressible cassette comprising a) a polynucleotide encoding an HPV protein selected from the group consisting of L1, E1, E2, and E7 proteins, wherein the polynucleotide is codon-optimized for expression in a human host cell; and b) a promoter operably linked to the polynucleotide.

This invention also relates to vaccine compositions comprising a vector which carries the oligonucleotides to a human host, and allows for expression of the encoded protein. The protein is expressed in an amount sufficient to induce an immune response. In preferred embodiments, the vector is a plasmid vector or an adenoviral vector.

This invention also relates to a method of making a HPV protein comprising expressing in a host cell a synthetic polynucleotide encoding a human papillomavirus (HPV) protein, or mutated form of a HPV protein which has reduced protein function as compared to wild-type protein, but which maintains immunogenicity, the polynucleotide sequence comprising codons optimized for expression in a human host.

BRIEF DECRIPTION OF THE DRAWINGS

FIG. 1 is the nucleotide sequence of a codon-optimized HPV16 L1 gene (SEQ.ID.NO:1).

FIG. 2 is the nucleotide sequence of a codon-optimized HPV16 E1 gene (SEQ.ID.NO:2). In this particular sequence, there are further mutations which changes the amino acid sequence of the expressed protein—the glycine residue at position 428 has been converted to aspartic acid, and the tryptophan residue at position 439 is now arginine.

FIG. 3 is the nucleotide sequence of a codon-optimized HPV16 E2 gene (SEQ.ID.NO:3). In this particular sequence, the glutamic acid residue at position 39 has been changed to an alanine, and the isoleucine residue at position 73 has also been changed to an alanine.

FIG. 4 is the nucleotide sequence of a codon-optimized HPV16 E7 gene.(SEQ.ID.NO:4). In this particular sequence, the cysteine residue at position 24 has been changed to glycine, and the glutamic acid residue at position 26 has been changed to a glycine.

FIG. 5 is the nucleotide sequence of a codon-optimized HPV6a E7 gene (SEQ.ID.NO:5).

FIG. 6 is the nucleotide sequence of a codon-optimized HPV18 E7 gene (SEQ.ID.NO:6).

FIG. 7 is the nucleotide sequence of a codon-optimized HPV6a E2 gene (SEQ.ID.NO:7).

FIG. 8 is the nucleotide sequence of a codon-optimized HPV18 E2 gene (SEQ.ID.NO:8).

FIG. 17 is a table of oligonucleotides (SEQ.ID.NOS: 9–32) used to generate synthetic HPV16 L1.

FIG. 18 is a table of oligonucleotides (SEQ.ID.NOS: 33–64) used to generate synthetic HPV16 E1.

FIG. 19 is a table of oligonucleotides (SEQ.ID.NOS: 65–84) used to generate synthetic HPV16 E2.

FIG. 20 is a table of oligonucleotides (SEQ.ID.NOS: 85–90) used to generate synthetic HPV16 E7.

FIG. 21 is a table of oligonucleotides (SEQ.ID.NOS: 91–96) used to generate synthetic HPV6a E7.

FIG. 22 is a table of oligonucleotides (SEQ.ID.NOS: 97–102) used to generate synthetic HPV18 E7.

FIG. 23 is a table of oligonucleotides (SEQ.ID.NOS: 103–126) used to generate synthetic HPV6a E2.

FIG. 24 is a table of oligonucleotides (SEQ.ID.NOS: 127–150) used to generate synthetic HPV18 E2.

Figure 25:
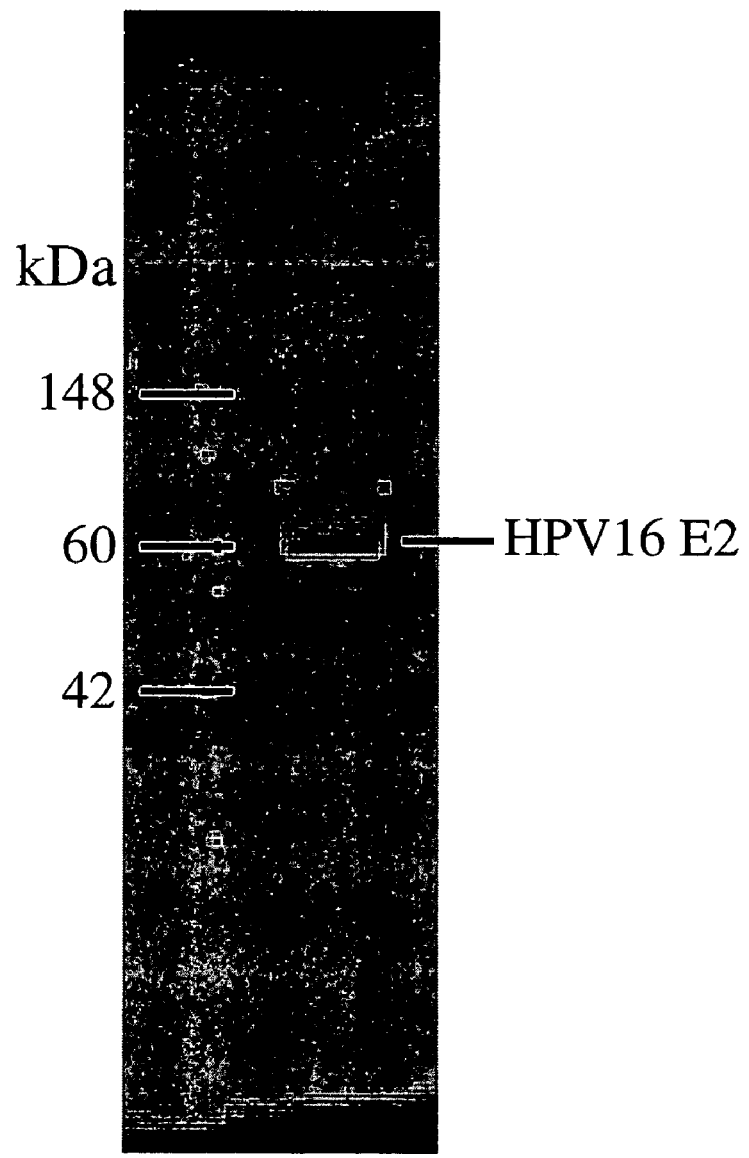

FIG. 25 is a Western blot of JCL-031 cell lysate. Cell lysate was prepared from JCL-031 cells grown in selection medium containing 400 µg/mL G418. The immunoblot was developed with anti-HPV 16 E2 (goat 248) antisera. Positions of molecular weight markers are indicated.

Figure 26:
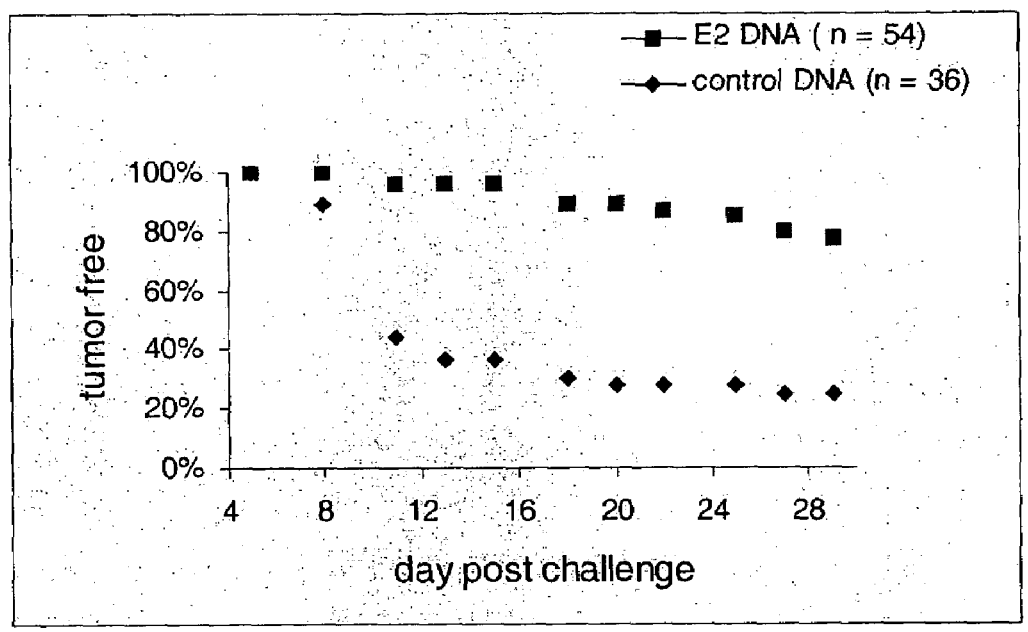

FIG. 26 shows protection from JCL-031 cell-induced tumor outgrowth. E2 DNA- or control DNA-immunized mice were challenged by subcutaneous injection of $5 \times 10^5$ JCL-031 cells into the left inguinal region. Beginning five days after this challenge, all animals were observed at two or three day intervals until four weeks after inoculation. Tumors were detected and monitored by visual inspection, palpation of the inguinal region, and measurement of tumor diameter with calipers.

The term "promoter" as used herein refers to a recognition site on a DNA strand to which the RNA polymerase binds. The promoter forms an initiation complex with RNA polymerase to initiate and drive transcriptional activity. The complex can be modified by activating sequences termed "enhancers" or inhibiting sequences termed "silencers".

The term "cassette" refers to the sequence of the present invention which contains the nucleic acid sequence which is to be expressed. The cassette is similar in concept to a cassette tape; each cassette has its own sequence. Thus by interchanging the cassette, the vector will express a different sequence. Because of the restrictions sites at the 5' and 3' ends, the cassette can be easily inserted, removed or replaced with another cassette.

The term "vector" refers to some means by which DNA fragments can be introduced into a host organism or host tissue. There are various types of vectors including plasmid, virus (including adenovirus), bacteriophages and cosmids.

The term "effective amount" means sufficient vaccine composition is introduced to produce the adequate levels of the polypeptide, so that an immune response results. One skilled in the art recognizes that this level may vary.

"Synthetic" means that the HPV gene has been modified so that it contains codons which are preferred for human expression. In many cases, the amino acids encoded by the gene remain the same. In some embodiments, the synthetic gene may encode a modified protein.

The term "native" means that the gene contains the DNA sequence as found in occurring in nature. It is a wild type sequence of viral origin.

DETAILED DESCRIPTION OF THE INVENTION

Synthetic DNA molecules encoding various HPV proteins are provided. The codons of the synthetic molecules are designed so as to use the codons preferred by the projected host cell, which is preferred embodiments is a human cell. The synthetic molecules may be used as a polynucleotide vaccine which provides effective immunoprophylaxis against papillomavirus infection through neutralizing antibody and cell-mediated immunity. The synthetic molecules may be used as an immunogenic composition. This invention provides polynucleotides which, when directly introduced into a vertebrate in vivo, including mammals such as primates and humans, induce the expression of encoded proteins within the animal.

The gene encoding a L1, E1, E2 and/or E7 from any serotype HPV can be modified in accordance with this invention. It is preferred that the HPV chosen be one which is known to cause a pathological condition in humans. For this reason, it is preferred that the HPV gene be selected from the group consisting of: HPV6a, HPV6b, HPV11, HPV16, HPV18, HPV31, HPV33, HPV35, HPV39, HPV45, HPV51, HPV52, HPV56, HPV58, HPV68 or variants thereof. The vaccine formulation of this invention may contain a mixture of HPV type protein genes (for example, genes from HPV6, 11, 16 and 18), and/or it may also contain a mixture of protein genes (i.e. L1, E1, E2, and/or E7).

Codon Optimization

The wild-type sequences for many HPV genes are known. In accordance with this invention, HPV gene segments were converted to sequences having identical translated sequences but with alternative codon usage as defined by Lathe, 1985 "Synthetic Oligonucleotide Probes Deduced from Amino Acid Sequence Data: Theoretical and Practical Considerations" *J. Molec. Biol.* 183:1–12, which is hereby incorporated by reference. The methodology may be summarized as follows:

1. Identify placement of codons for proper open reading frame.

2. Compare wild type codon for observed frequency of use by human genes.

3. If codon is not the most commonly employed, replace it with an optimal codon for high expression in human cells.

4. Repeat this procedure until the entire gene segment has been replaced.

5. Inspect new gene sequence for undesired sequences generated by these codon replacements (e.g., "ATTTA" sequences, inadvertent creation of intron splice recognition sites, unwanted restriction enzyme sites, etc.) and substitute codons that eliminate these sequences.

6. Assemble synthetic gene segments and test for improved expression.

In accordance with this invention, it has been found that the use of alternative codons encoding the same protein sequence may remove the constraints on expression of HPV proteins by human cells.

These methods were used to create the following synthetic gene segments for various papillomavirus genes creating a gene comprised entirely of codons optimized for high level expression. While the above procedure provides a summary of our methodology for designing codon-optimized genes for DNA vaccines, it is understood by one skilled in the art that similar vaccine efficacy or increased expression of genes may be achieved by minor variations in the procedure or by minor variations in the sequence.

In some embodiments of this invention, alterations have been made (particularly in the E-protein native protein sequences) to reduce or eliminate protein function while preserving immunogenicity. Mutations which decrease enzymatic function are known. Certain alterations were made for purposes of expanding safety margins and/or improving expression yield. These modifications are accomplished by a change in the codon selected to one that is more highly expressed in mammalian cells. In the case of HPV16 E1, for example two mutations were introduced: glycine at amino acid number 482 was changed to aspartic acid by conversion of GGC to GAC; and tryptophan was changed to arginine at position 439 by conversion of TGG to CGC.

For HPV16 E2, conversion of glutamic acid at position 39 to alanine and isoleucine at position 73 to alanine by conversion of both codons each to GCC.

For HPV16 E7, conversion of cysteine at position 24 to glycine and glutamic acid at position 26 to glycine was permitted by alteration of TGC and the GAG respectively both to GGC.

The codon-optimized genes are then assembled into an expression cassette which comprises sequences designed to provide for efficient expression of the protein in a human cell. The cassette preferably contains the codon-optimized gene, with related transcriptional and translations control sequences operatively linked to it, such as a promoter, and termination sequences. In a preferred embodiment, the promoter is the cytomegalovirus promoter with the intron A sequence (CMV-intA), although those skilled in the art will recognize that any of a number of other known promoters such as the strong immunoglobulin, or other eukaryotic gene promoters may be used. A preferred transcriptional terminator is the bovine growth hormone terminator, although other known transcriptional terminators may also be used. The combination of CMVintA-BGH terminator is particularly preferred.

Examples of preferred gene sequences are given in SEQ.ID.NOS: 1–8.

Vectors

In accordance with this invention, the expression cassette encoding at least one HPV protein is then inserted into a vector. The vector is preferably a plasmid or an adenoviral vector, although linear DNA linked to a promoter, or other vectors, such as adeno-associated virus or a modified vaccinia virus vector may also be used.

If the vector chosen is an adenovirus, it is preferred that the vector be a so-called first-generation adenoviral vector. These adenoviral vectors are characterized by having a non-functional E1 gene region, and preferably a deleted adenoviral E1 gene region. In some embodiments, the expression cassette is inserted in the position where the adenoviral E1 gene is normally located. In addition, these vectors optionally have a non-functional or deleted E3 region. The adenoviruses can be multiplied in known cell lines which express the viral E1 gene, such as 293 cells, or PerC.6 cells.

For convenience in manipulating the adenoviral vector, the adenovirus may be in a shuttle plasmid form. This invention is also directed to a shuttle plasmid vector which comprises a plasmid portion and an adenovirus portion, the adenovirus portion comprising an adenoviral genome which has a deleted E1 and optional E3 deletion, and has an inserted expression cassette comprising at least one codon-optimized HPV gene. In preferred embodiments, there is a restriction site flanking the adenoviral portion of the plasmid so that the adenoviral vector can easily be removed. The shuttle plasmid may be replicated in prokaryotic cells or eukaryotic cells.

Standard techniques of molecular biology for preparing and purifying DNA constructs enable the preparation of the adenoviruses, shuttle plasmids and DNA immunogens of this invention.

If the vector chosen is plasmid DNA, it is preferred that the vector contain one or more promoters recognized by mammalian or insect cells. In a preferred embodiment, the plasmid would contain a strong promoter such as, but not limited to the CMV promoter. The gene to be expressed would be linked to such a promoter. An example of such a plasmid would be the mammalian expression plasmid V1Jns as described (J. Shiver et. al. 1996, in *DNA Vaccines*, eds., M. Liu, et al. N.Y. Acad. Sci., N.Y., 772:198–208 and is herein incorporated by reference).

In some embodiment of this invention, the both the vaccine plasmid and the adenoviral vectors may be administered to a vertebrate in order to induce an immune response. In this case, the two vectors are administered in a "prime and boost" regimen. For example the first type of vector is administered, then after a predetermined amount of time, for example, 1 month, 2 months, six months, or other appropriate interval, a second type of vector is administered. Preferably the vectors carry expression cassettes encoding the same polynucleotide or combination of polynucleotides.

Thus, another aspect of this invention is a method for inducing an immune response against human papillomavirus in a vertebrate, comprising A) introducing into the vertebrate a first vector comprising a polynucleotide encoding an HPV protein selected from the group consisting of L1, E1, E2, and E7 proteins, wherein the polynucleotide is codon-optimized for expression in a human host cell;

B) allowing a predetermined amount of time to pass; and

C) introducing into the vertebrate a second vector comprising adenoviral vaccine vector comprising an adenoviral genome with a deletion in the E1 region, and an insert in the E1 region, wherein the insert comprises an expression cassette comprises i) a polynucleotide encoding an HPV protein selected from the group consisting of L1, E1, E2, and E7 proteins or mutant forms thereof, wherein the polynucleotide is codon-optimized for expression in a human host cell; and ii) a promoter operably linked to the polynucleotide.

In general, is preferred that the first vector be a plasmid vaccine vector and the second vector be an adenoviral vector. Thus this invention is directed to a method for inducing immune responses in a vertebrate comprising:

A) introducing into the vertebrate a plasmid vaccine, wherein the plasmid vaccine comprises a plasmid portion and an expression cassette portion, the expression cassette portion comprising:

i) a polynucleotide encoding an HPV protein selected from the group consisting of L1, E1, E2, and E7 proteins, wherein the polynucleotide is codon-optimized for expression in a human host cell; and ii) a promoter operably linked to the polynucleotide;

B) allowing a predetermined amount of time to pass; and

C) introducing into the vertebrate an adenoviral vaccine vector comprising an adenoviral genome with a deletion in the E1 region, and an insert in the E1 region, wherein the insert comprises an expression cassette comprising:

i) a polynucleotide encoding an HPV protein selected from the group consisting of L1, E1, E2, and E7 proteins or mutant forms thereof, wherein the polynucleotide is codon-optimized for expression in a human host cell; and ii) a promoter operably linked to the polynucleotide.

In yet another embodiment of the invention, the codon-optimized genes may be introduced into a recipient by way of a plasmid or adenoviral vector, as a "prime", and then a "boost" is accomplished by introducing into the recipient a polypeptide or protein which is essentially the same as that which is encoded by the codon-optimized gene. Fragments of a full length protein may be substituted, especially those which are immunogenic and/or include an epitope.

The amount of expressible DNA or transcribed RNA to be introduced into a vaccine recipient will depend partially on the strength of the transcriptional and translational promoters used and on the immunogenicity of the expressed gene product. In general, an immunologically or prophylactically effective dose of about 1 ng to 100 mg, and preferably about 10 μg to 300 μg of a plasmid vaccine vector is administered directly into muscle tissue. An effective dose for recombinant adenovirus is approximately $10^6$–$10^{12}$ particles and preferably about $10^7$–$10^{11}$ particles. Subcutaneous injection, intradermal introduction, impression through the skin, and other modes of administration such as intraperitoneal, intravenous, or inhalation delivery are also contemplated. It is also contemplated that booster vaccinations may be provided. Parenteral administration, such as intravenous, intramuscular, subcutaneous or other means of administration with adjuvants such as interleukin-12 protein, concurrently with or subsequent to parenteral introduction of the vaccine of this invention is also advantageous.

The vaccine vectors of this invention may be naked, that is, unassociated with any proteins, adjuvants or other agents which impact on the recipients' immune system. In this case, it is desirable for the vaccine vectors to be in a physiologically acceptable solution, such as, but not limited to, sterile saline or sterile buffered saline or the DNA may be associated with an adjuvant known in the art to boost immune responses, such as a protein or other carrier. Agents which assist in the cellular uptake of DNA, such as, but not limited to, calcium ions, may also be used to advantage. These agents are generally referred to herein as transfection facilitating reagents and pharmaceutically acceptable carriers. Techniques for coating microprojectiles coated with polynucleotide are known in the art and are also useful in connection with this invention.

The following examples are offered by way of illustration and are not intended to limit the invention in any manner.

EXAMPLES

Example 1

Synthetic Gene Construction

Synthetic gene sequences for human papillomavirus proteins L1, E1, E2, and E7 were generated by reverse translation of amino acid sequences using the most frequently used codons found in highly expressed mammalian genes. (R. Lathe, 1985, *J. Mol. Biol.* 183: 1–12, which is hereby incorporated by reference). Some adjustments to these codon-optimized sequences were made to introduce or remove restriction sites. Oligonucleotides based on these sequences were chemically synthesized (Midland Certified Reagents; Midland, Tex.) and assembled by PCR amplification. (J. Haas et. al., 1996, *Current Biology* 6:315–324; and *PCR Protocols*, M. Innis, et al, eds., Academic Press, 1990, both of which are hereby incorporated by reference).

Full-length sequences were cloned into the mammalian expression vector V1Jns (J. Shiver et. al. 1996, in *DNA Vaccines*, eds., M. Liu, et al. N.Y. Acad. Sci., N.Y., 772: 198–208, which is hereby incorporated by reference) and sequenced by standard methodology. In cases where the actual sequence differed from the expected and resulted in amino acid substitution, that sequence was corrected by PCR mutagenesis as previously described (*PCR Protocols*, M. Innis, et al, eds., Academic Press, 1990, pg 177–180).

Protein expression was evaluated by transient transfection of equal quantities of plasmid DNA into 293 (transformed embryonic human kidney) cells which were harvested at 48 hr post DNA addition. Cell lysates were normalized to provide equal protein loadings. Analysis was by indirect immunofluorescence or immunoblot (Western) analysis using sera prepared to each of the HPV proteins. (Current Protocols in Molecular Biology, eds., F. Ausabel, et. Al., John Wiley and Sons, 1998, which is hereby incorporated by reference).

Example 2

Synthesis of HPV 16 L1

The gene encoding HPV16 L1 was prepared by the annealing and extension of the 14 oligomers listed in FIG. 17. Five separate extension reactions were performed to create fragments of the gene, designated L1A, L1B, L1C, L1D and L1E by PCR using conditions similar to those described in EXAMPLE 3 and 4, below.

L1A was constructed using oligomer sequences MN4A1 (SEQ.ID.NO:9), MN4A2 (SEQ.ID.NO:16) and MN4A3 (SEQ.ID.NO:10) which were amplified using the oligomers MN604 (SEQ.ID.NO:32) and MN596 (SEQ.ID.NO:24).

L1B was constructed using oligomer sequences MN4A4 (SEQ.ID.NO:17), MN4A5 (SEQ.ID.NO:11) and MN4A6 (SEQ.ID.NO:18) and were amplified using the oligomers MN595 (SEQ.ID.NO:23) and MN598 (SEQ.ID.NO:26).

L1C was created using oligomer sequences MN4A7 (SEQ.ID.NO:12) and MN4A8 (SEQ.ID.NO:19) and were amplified using the oligomers MN597 (SEQ.ID.NO:25) and MN602 (SEQ.ID.NO:30).

L1D was created using oligomer sequences MN4A9 (SEQ.ID.NO:13), MN4A10 (SEQ.ID.NO:20) and MN4A11 (SEQ.ID.NO:14) which were amplified using the oligomers MN597 (SEQ.ID.NO:25) and MN602 (SEQ.ID.NO:30).

L1E was created using oligomer sequences MN4A12 (SEQ.ID.NO:21), MN4A13 (SEQ.ID.NO:15) and MN4A14 (SEQ.ID.NO:22) which were amplified using the oligomers MN601 (SEQ.ID.NO:29) and MN603 (SEQ.ID.NO:31).

Fragments L1A, L1B, L1C, L1D and L1E resulting from the PCR reactions were gel separated on low melting point agarose with the appropriately-sized products excised and purified using the Agarase™ method (Boehringer Mannheim Biochemicals) as recommended by the manufacturer. Fragments L1A, L1B and L1C were combined in a subsequent PCR reaction using oligomers MN604 (SEQ.ID.NO:32) and MN600 (SEQ.ID.NO:28) to assemble L1A-B-C; fragments L1D and L1E were assembled to L1D-E by subsequent PCR with the oligomers MN599 (SEQ.ID.NO:27) and MN603 (SEQ.ID.NO:31). The complete gene was then assembled by additional PCR reactions in which fragments L1A-B-C, L1D-E were combined with oligomers MN604 (SEQ.ID.NO:32) and MN603 (SEQ.ID.NO:31) in a final series of PCR reactions. The resulting 1.5 kb product was gel isolated, digested with Bgl II and subcloned into the V1Jns and sequenced. In instances where a mutation was observed, it was corrected by PCR mutagenesis as described in EXAMPLE 1. DNA was isolated from a clone with the correct HPV16 L1 DNA sequence and proper orientation within V1Jns for use in transient transfection assays as described in EXAMPLE 1.

Transfection Results (HPV16 L1)

Figure 9:
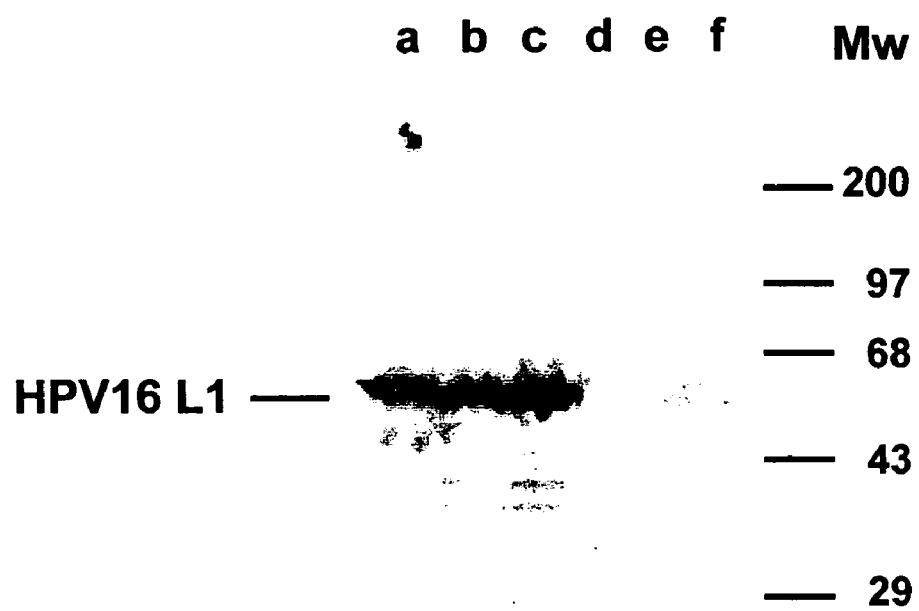
FIG. 9 shows the results of immunoblot analysis of lysates of 293 cells transiently-transfected with native (lanes d, e, f) or synthetic (a, b, c) HPV16 L1 sequences in the expression vector V1Jns.

FIG. 9 shows the HPV16 L1 immunoblot results of lysates of 293 cells transiently-transfected with the V1Jns plasmid containing either the native or the codon-optimized, synthetic HPV16 L1. Lanes a, b and c are the expression levels achieved using the synthetic HPV16 L1 expression construct. High levels of immunoreactive material are apparent in each of these lanes with the predominant band at approximately 55 kDa, consistent with the expected molecular weight for full-length HPV16 L1. In contrast, virtually no immunoreactive material is apparent in the lanes containing lysates transfected with the native HPV16 L1/V1Jns plasmid (lanes d, e, and f). Since all cell lysate loadings were normalized and equivalent DNA amounts were used in the transfections, these findings indicate that the synthetic gene sequence greatly increased the levels of HPV16 L1 protein accumulation relative to that of the native gene sequence.

Example 3

Synthesis of HPV 16 E1

The gene encoding the modified form of HPV16 E1 was assembled from a series of fragments: E1A, E1B, E1C, E1D, E1E and E1F, using the oligomers listed in FIG. 18. E1A was formed by assembly of oligomers MN605 (SEQ.ID.NO:33), MN606 (SEQ.ID.NO:34) and MN607 (SEQ.ID.NO:35) and amplified using oligomers MN636 (SEQ.ID.NO:64) and MN624 (SEQ.ID.NO:52).

E1B was formed by assembly of oligomers MN608 (SEQ.ID.NO:36), MN609 (SEQ.ID.NO:37) and MN610 (SEQ.ID.NO:38) which were amplified with oligomers MN623 (SEQ.ID.NO:51) and MN626 (SEQ.ID.NO:54).

E1C was formed by assembly of oligomers MN611 (SEQ.ID.NO:39) and MN612 (SEQ.ID.NO:40) which were amplified with oligomers MN625 (SEQ.ID.NO:53) and MN628 (SEQ.ID.NO:56).

E1D was formed by assembly of oligomers MN613 (SEQ.ID.NO:41), MN614 (SEQ.ID.NO:42) and MN615 (SEQ.ID.NO:43) which were amplified with oligomers MN627 (SEQ.ID.NO:55) and MN630 (SEQ.ID.NO:58).

E1E was formed by assembly of oligomers MN616 (SEQ.ID.NO:44), MN617 (SEQ.ID.NO:45) and MN618 (SEQ.ID.NO:46) which were amplified with oligomers MN629 (SEQ.ID.NO:57) and MN632 (SEQ.ID.NO:60).

E1F was formed by assembly of oligomers MN619 (SEQ.ID.NO:47), MN620 (SEQ.ID.NO:48) and MN621 (SEQ.ID.NO:49) which were amplified with oligomers MN631 (SEQ.ID.NO:59) and MN635 (SEQ.ID.NO:63).

Products of these PCR reactions were gel isolated and combined in subsequent rounds of PCR to form a 2 kb gene fragment encoding HPV16 µl using methods described above. The resulting HPV16 E1 was inserted into the V1Jns expression vector as above and utilized in transient transfection studies as described in EXAMPLE 1.

Transfection Results (HPV16 E1)

Figure 10:
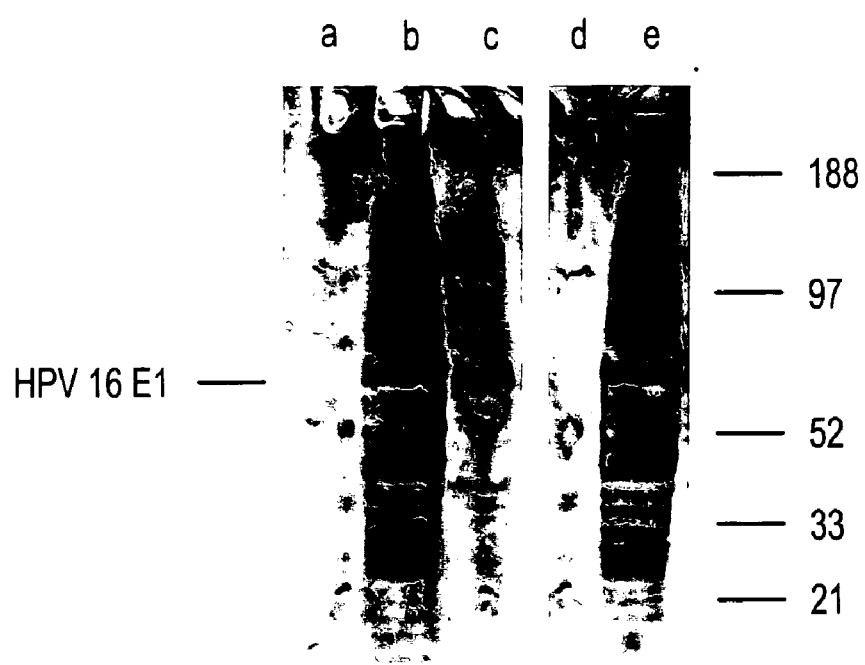
FIG. 10 shows the results of immunoblot analysis of lysates of 293 cells transiently-transfected with native or synthetic HPV16 E1 sequences in the expression vector V1Jns. Lanes a and d contain native HPV16 E1 sequences; lanes b and e contain synthetic HPV16 E1, and lane c is a mock-transfected control.

FIG. 10 shows the HPV16 E1 immunoblot results of lysates of 293 cells transiently-transfected with the V1Jns plasmid containing either the native, or the codon-optimized, synthetic HPV16 E1. Lanes b and e are the expression levels achieved using the codon-optimized HPV16 E1 expression construct. High levels of HPV16 E1-specific immunostaining are apparent with a predominant band in lanes b and e at 72 kDa, consistent with the expected size for full-length HPV16 E1. In addition, there a number of smaller immunoreactive products which appear to be E1-specific as they are not observed in the mock transfected control (lane c).

A very different expression profile is observed in lysates of cells transfected with the native HPV16 E1/V1Jns construct, however. As shown in lanes a and d, only minimal amounts of immunoreactive material can be visualized which is not present in the mock transfection control. Since all cell lysate loadings were normalized and equivalent DNA amounts were used in the transfections these findings indicate that the synthetic gene sequence greatly increased the levels of HPV16 E1 protein accumulation relative to that of the native gene sequence.

Example 4

Synthesis of HPV 16 E2

Fragment AD. A 50 µl reaction containing oligonucleotides 13856-307-2A (SEQ.ID.NO:65), 13856-307-2B (SEQ.ID.NO:71), 13856-307-2C (SEQ.ID.NO:66), and 13856-307-2D (SEQ.ID.NO:72), at 150 nM each, dNTPs 0.5 mM each, Native buffer (Stratagene; La Jolla, Calif.) and 1 µL Native Pfu DNA polymerase (Stratagene) was incubated in a GeneAmp 9700 thermocycler (Perkin Elmer Applied Biosystems; Foster City, Calif.) under the following conditions: 95° C., 2 min.; 20 cycles of 95° C., 45 sec.; 55° C., 45 sec.; and 72° C., 2.5 min. Added to the reaction were primers 13856-307-2PA (SEQ.ID.NO:78) and 13856-307-2PD (SEQ.ID.NO:82) to a final concentration of 400 nM each, and 1 µL of Native Pfu DNA polymerase. The mixture was incubated for 2 min at 95° C. and then 25 cycles of 95° C., 45 sec; 55° C., 45 sec; and 72° C., 2.5 min. The gel-isolated full-length fragment AD was amplified for 20 cycles under the same conditions using primers 13856-307-2PA (SEQ.ID.NO:78) and 13856-307-2PD (SEQ.ID.NO:82).

Fragment EH. A 50 µl reaction containing oligonucleotides 13856-307-2E (SEQ.ID.NO:67), 13856-307-2F (SEQ.ID.NO:73), 13856-307-2G (SEQ.ID.NO:68), and 13856-307-2H (SEQ.ID.NO:74) at 150 nM each, dNTPs 0.5 mM each, Native buffer and 1 µL Native Pfu DNA polymerase was incubated under the following conditions: 95° C., 2 min; 20 cycles of 95° C., 2 min.; 45 sec.; 55° C., 45 sec.; and 72° C., 2.5 min. Added to the reaction were primers 13856-307-2PE (SEQ.ID.NO:80) and 13856-307-2PH (SEQ.ID.NO:83) to a final concentration of 400 nM each, and 1 µL of Native Pfu DNA polymerase. The mixture was incubated for 95° C., 2 min.; then 25 cycles of 95° C., 45 sec.; 55° C., 45 sec.; and 72° C., 2.5 min.

Fragment IL. A 50 µl reaction containing oligonucleotides 13856-307-21 (SEQ.ID.NO:69), 13856-307-2J (SEQ.ID.NO:75), 13856-307-2K (SEQ.ID.NO:70), and 13856-307-2L (SEQ.ID.NO:76) at 150 nM each, dNTPs 0.5 mM each, Native buffer and 1 µL Native Pfu DNA polymerase was incubated under the following conditions: 95° C., 2 min; 20 cycles of 95° C., 2 min.; 45 sec.; 55° C., 45 sec.; and 72° C., 2.5 min. Added to the reaction were primers 13856-307-2PI (SEQ.ID.NO:81) and 13856-307-2PL (SEQ.ID.NO. 84) to a final concentration of 400 nM each, and 1 µL of Native Pfu DNA polymerase. The mixture was incubated at 95° C., 2 min.; then 25 cycles of 95° C., 45 sec.; 55° C., 45 sec.; and 72° C., 2.5 min.

Fragment AH. A 50 µl reaction containing 1.5 µl each of AD and EH PCR products, dNTPs 0.5 mM each, Native buffer and 1 µL Native Pfu DNA polymerase was incubated under the following conditions: 95° C., 2 min; 20 cycles of 95° C., 45 sec.; 55° C., 45 sec.; and 72° C., 3.5 min. Added to the reaction were primers 13856-307-2PA (SEQ.ID.NO: 78) and 13856-307-2PH (SEQ.ID.NO:83) to a final concentration of 400 nM each, and 1 µL of Native Pfu DNA polymerase. The mixture was incubated at 95° C., 2 min.; then 25 cycles of 95° C., 45 sec.; 55° C., 45 sec.; and 72° C., 3.5 min.

Fragment IM. A 50 µl reaction containing 1 µl of IL PCR product, oligonucleotides 13856-307-2M (SEQ.ID.NO:77) and 13856-307-2PI (SEQ.ID.NO:81) each at a final concentration of 400 nM, dNTPs 0.5 mM each, Native buffer and 1 µL Native Pfu DNA polymerase was incubated under the following conditions: 95° C., 2 min; 25 cycles of 95° C., 45 sec.; 55° C., 45 sec.; and 72° C, 4 min.

Assembly of AM, full-length HPV16 E2. A 50 µl reaction containing 1.5 µl each of fragments AH and IM, dNTPs 0.5 mM each, Native buffer and 1 µL Native Pfu DNA polymerase was incubated under the following conditions: 95° C., 2 min; 20 cycles of 95° C., 45 sec.; 55° C., 45 sec.; and 72° C., 4 min. Added to the reaction were primers 13856-307-2PA (SEQ.ID.NO:78) and 13856-307-2PM (SEQ.ID.NO:79) at a final concentration of 400 µM each, and 1 µL of Native Pfu DNA polymerase. The mixture was incubated at 95° C., 2 min.; then 25 cycles of 95° C., 45 sec.; 55° C., 45 sec.; and 72° C., 4 min. The resultant full-length fragment was isolated by electrophoresis through a 1.2% agarose gel the DNA recovered with a QIAquick column (Qiagen; Santa Clarita, Calif.) and subcloned into the expression vector V1Jns for evaluation.

Transfection Results (HPV16 E2)

Figure 11:
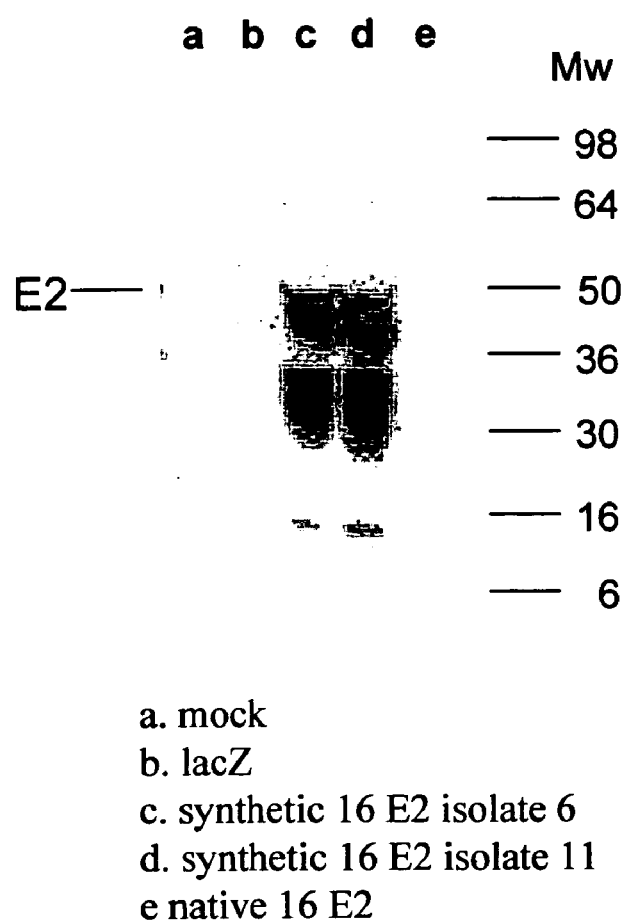
FIG. 11 shows the results of immunoblot analysis of lysates of 293 cells transiently-transfected with native or synthetic HPV16 E2 sequences in the expression vector V1Jns. Lane a is mock-infected; lane b is lacZ control; lane c contains a synthetic HPV16 E2 isolate #6; lane d contains synthetic HPV16 E2 isolate #11, and lane e has native HPV16 E2.

FIG. 11 shows the HPV16 E2 immunoblot results of lysates of 293 cells transiently-transfected with the V1Jns plasmid containing either the native, or the synthetic HPV16 E2. Lanes c and d are the expression levels achieved using the codon-optimized HPV16 E2 expression construct. High levels of HPV16 E2-specific immunostaining are visible which appear to be E2-specific as they are not observed in the mock transfected control (lane c).

A very different expression profile is observed in lysates of cells transfected with the native HPV16 E21V1Jns construct, however. As shown in lane e, no immunoreactive material can be visualized. Since all cell lysate loadings were normalized and equivalent DNA amounts were used in the transfections, these findings indicate that the synthetic gene sequence greatly increased the levels of HPV16 E2 protein accumulation relative to those of the native gene sequence.

Example 5

Synthesis of HPV 16 E7

The gene encoding HPV16 E7 was assembled from a series of fragments, made using oligomers listed in FIG. 20.

A 50 µl reaction containing oligonucleotides 13856-307-7A (SEQ.ID.NO:85), 13856-307-7B (SEQ.ID.NO:87), 13856-307-7C (SEQ.ID.NO:86), and 13856-307-7D (SEQ.ID.NO:88) at 150 nM each, dNTPs 0.5 mM each, Native buffer (Stratagene; La Jolla, Calif.) and 1 µL Native Pfu DNA polymerase (Stratagene) was incubated in a GeneAmp 9700 thermocycler (Perkin Elmer Applied Biosystems; Foster City, Calif.) under the following conditions: 95° C., 2 min; 20 cycles of 95° C., 45 sec.; 55° C., 45 sec. and 72° C., 2.5 min. Added to the reaction were primers 13856-307-7PA (SEQ.ID.NO:89) and 13856-307-7PD (SEQ.ID.NO:90) to a final concentration of 400 nM), and 1 µL of Native Pfu DNA polymerase. The mixture was incubated for 25 cycles of 95° C., 45 sec.; 55° C., 45 sec. and 72° C., 2.5 min.

The resultant full-length fragment was isolated by electrophoresis through a 1.2% agarose gel in TBE (Current Protocols in Molecular Biology, eds., F. Ausabel, et. al., John Wiley and Sons, 1998, which is hereby incorporated by reference), stained with ethidium bromide, cut from the gel and recovered through a GenElute column (Supleco; Bellefonte, Pa.) and resuspended in 20 μl water. The sequence was further amplified in a 51 μl reaction containing 2 μl of fragment, 0.5 μM each of oligonucleotides 13856-307-7PA (SEQ.ID.NO:89) and 13856-307-7PD, (SEQ.ID.NO:90) dNTPs 0.5 mM each, Native buffer and Native Pfu DNA polymerase. The reaction was subjected to 20 cycles of 95° C., 45 sec.; 55° C., 45 sec. and 72° C., 2.5 min. The final amplified product isolated by electrophoresis as described above; the DNA recovered with a QIAquick column (Qiagen; Santa Clarita, Calif.) and subcloned into V1Jns.

Transfection Results (HPV16 E7)

Figure 12:
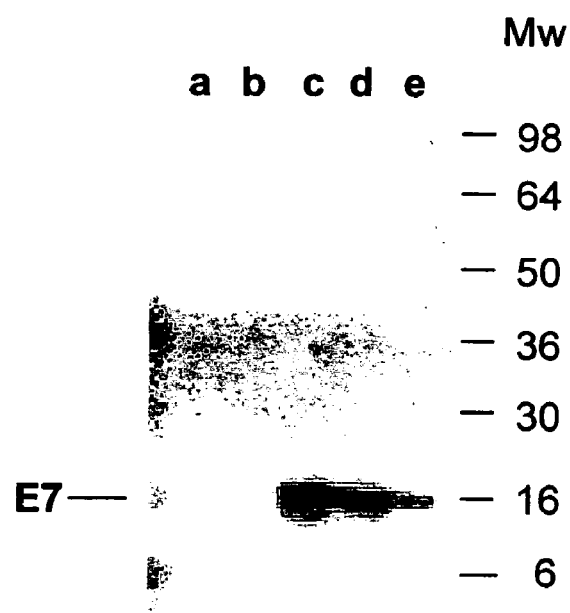
FIG. 12 shows the results of immunoblot analysis of lysates of 293 cells transiently-transfected with native or synthetic HPV16 E7 sequences in the expression vector V1Jns. Lane a is mock-infected; lane b is lacZ control; lane c contains synthetic HPV16 E7 isolate #2; lane d is synthetic HPV16 E7 isolate 4; and lane e is native HPV16 E7.

FIG. 12 shows the HPV16 E7 immunoblot results of lysates of 293 cells transiently-transfected with the V1Jns plasmid containing either the native (lane e) or synthetic HPV16 E7 (lanes c and d). High levels of HPV16 E7-specific immunostaining are visible in the synthetic HPV16 E7 gene cell lysate lanes which are considerably more intense in appearance than that of the native HPV16 E7 gene cell lysate (lane e). Lanes a and b are negative transfection controls which show the antibody staining is specific to HPV16 E7 sequences. Since all cell lysate loadings were normalized and equivalent DNA amounts were used in the transfections, these findings indicate that the synthetic gene sequence greatly increased the levels of HPV16 E2 protein accumulation relative to those of the native gene sequence.

Example 6

Synthesis of the E7 and E2-Encoding Genes from HPV6a and HPV18

The genes encoding HPV6a E7 and HPV 18 E7 were constructed using similar methods as described in EXAMPLE 4, except that the oligomers used to create the HPV6a E7 and HPV 18 E7 genes contain the sequences listed in FIG. 21 and FIG. 22, respectively. The construction of the synthetic genes encoding HPV6a E2 and HPV18 E2 was performed in a similar manner as detailed in EXAMPLE 5 using the oligomer sequences listed in FIG. 23 and FIG. 24 respectively.

Transfection Results: HPV6a E7 and HPV 18 E7

Figure 13:
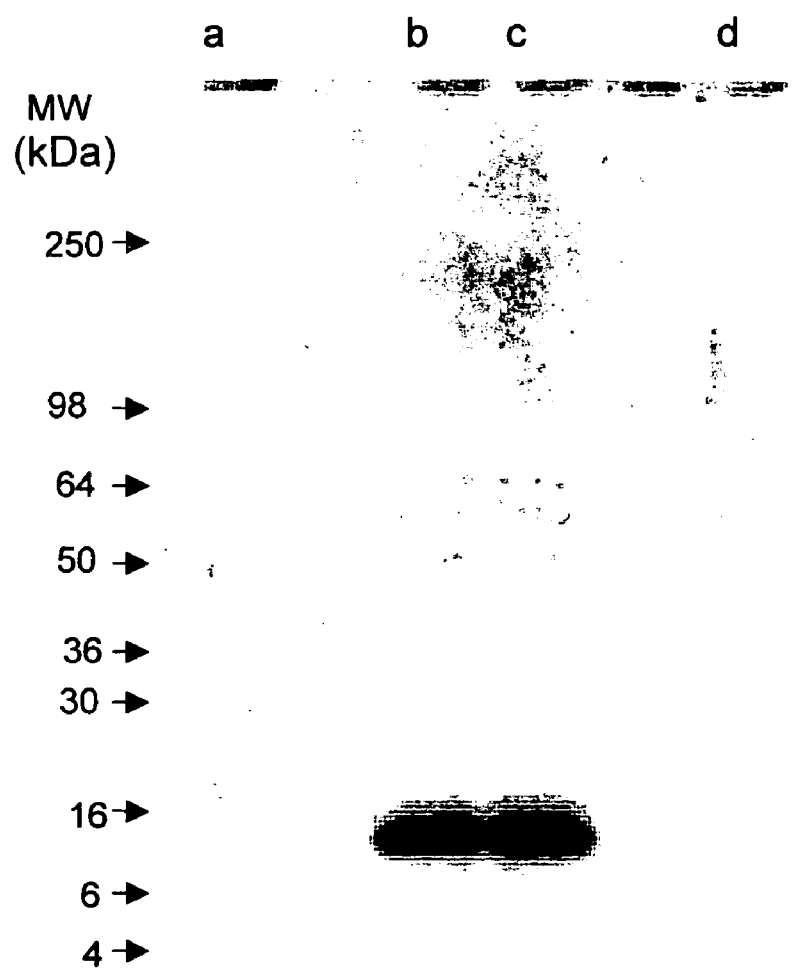
FIG. 13 shows the results of immunoblot analysis of lysates of 293 cells transiently-transfected with synthetic HPV6a E7 sequences in the expression vector V1Jns. Lanes b and c contain synthetic HPV6a E7 sequences; lane d contains a lacZ control, and lane a is a mock-transfected control.
Figure 14:
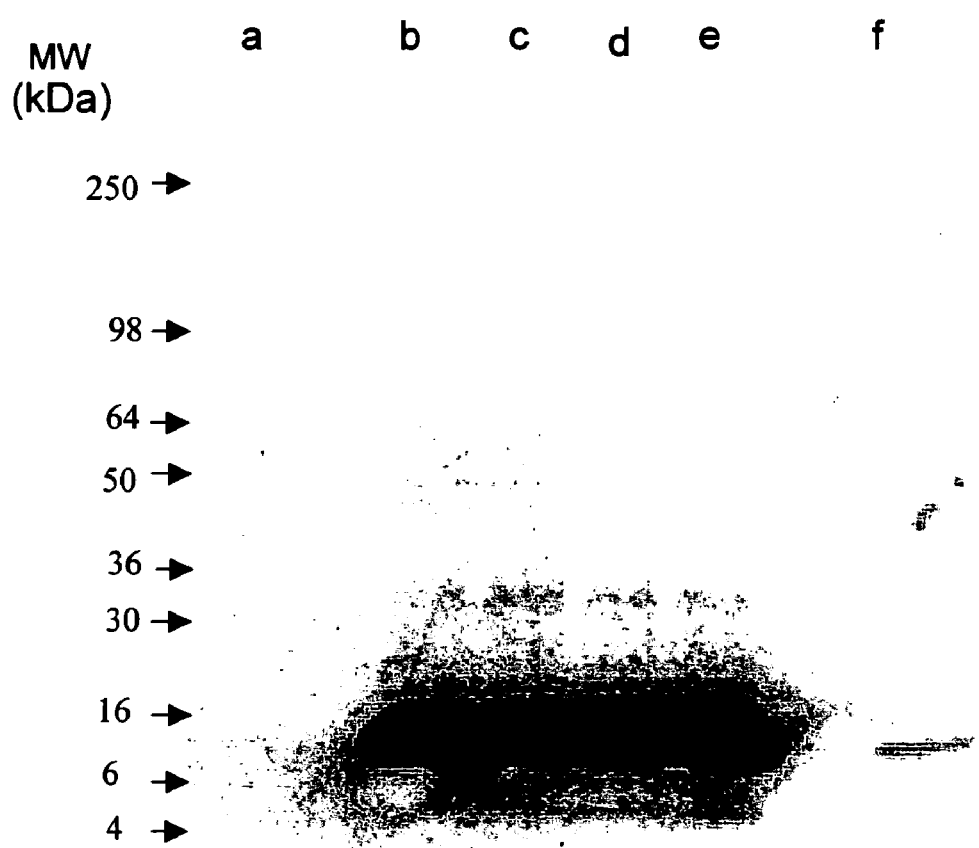
FIG. 14 shows the results of immunoblot analysis of lysates of 293 cells transiently-transfected with synthetic HPV18 E7 sequences in the expression vector V1Jns. Lanes b, c, d, and e contain synthetic HPV18 E7 sequences; lane f contains synthetic HPV16 E7 as an antibody control, and lane a is a mock-transfected control.

FIG. 13 shows the HPV6a E7 immunoblot results of lysates of 293 cells transiently-transfected with the V1Jns plasmid containing synthetic HPV6a E7 (lanes b and c). High levels of HPV6a E7-specific immunostaining are visible in the region expected for full-length HPV6a E7. A similar profile is found in FIG. 14 by HPV18 E7 immunoblot analysis of lysates of 293 cells transiently-transfected with the V1Jns plasmid containing synthetic HPV6a E7 (lanes b, c, d and e). High levels of HPV18 E7-specific immunostaining are visible where full-length HPV18 E7 would be found as indicated by the location of the purified HPV18 protein control (lane f). There does not appear to be any stained material in the negative control lane a which indicates the staining in the other lanes is HPV18 E7-specific.

Figure 15:
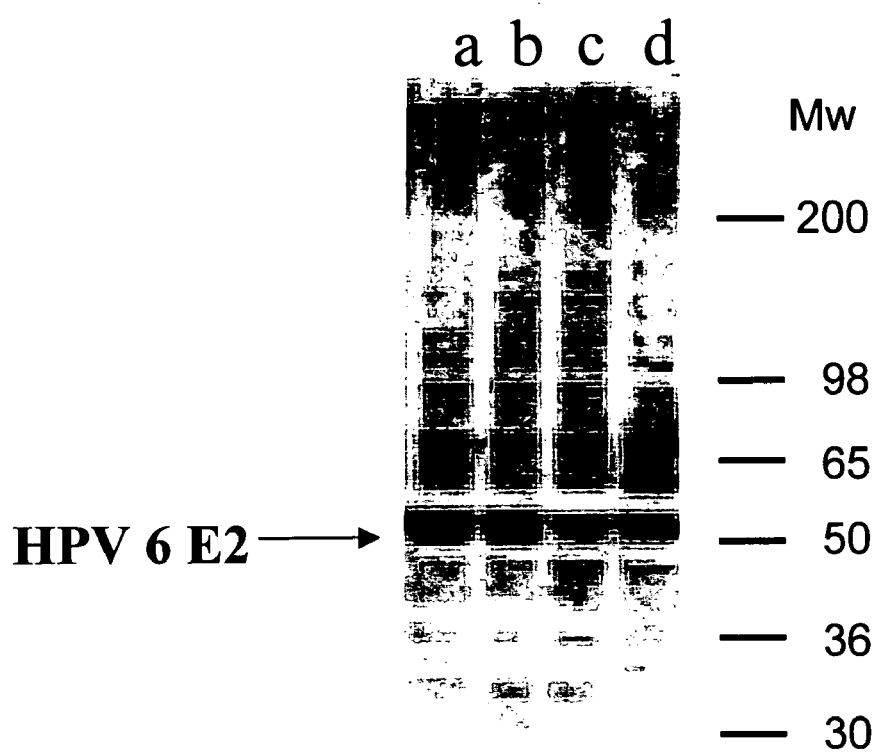
FIG. 15 shows the results of immunoblot analysis of lysates of 293 cells transiently-transfected with synthetic HPV6a E2 sequences in the expression vector V1Jns. Lanes a and b contain synthetic E2 sequences; lane c is a beta-gal control, and lane d is mock-transfected.
Figure 16:
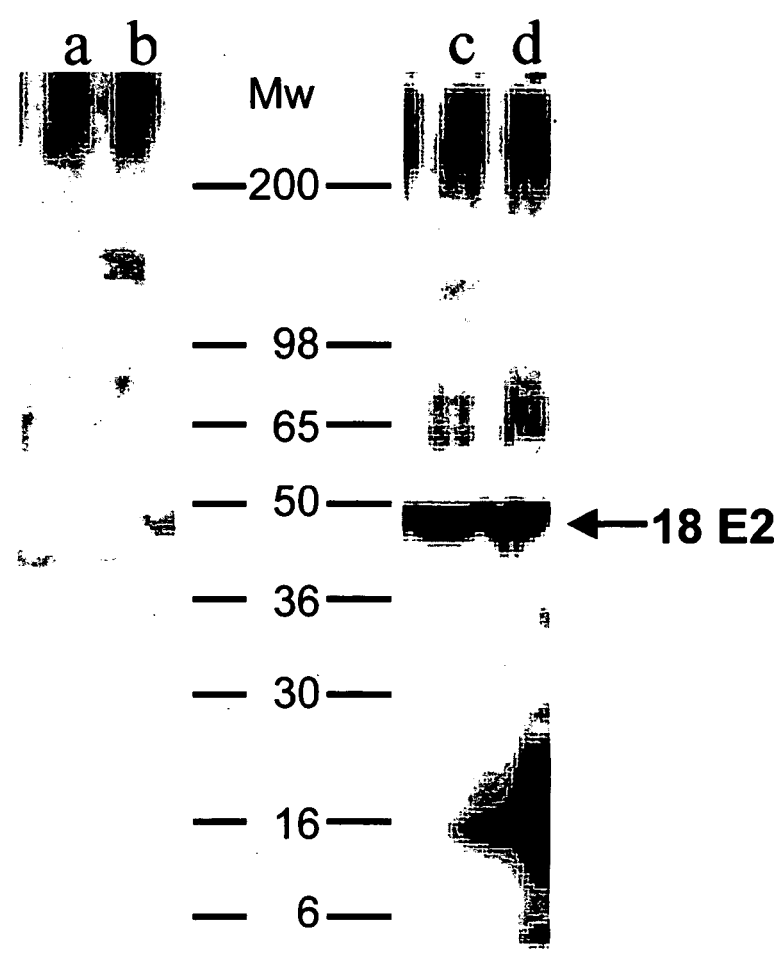
FIG. 16 shows the results of immunoblot analysis of lysates of 293 cells transiently-transfected with synthetic HPV18 E2 sequences in the expression vector V1Jns. Lane a is beta-gal control; lane b is mock transfected; and lanes c and d have synthetic sequences.

Expression of the synthetic gene encoding HPV6a E2 in V1Jns was evaluated by immunoblot analysis of transfected 293 cells which is shown in FIG. 15. Lanes a and b are cell lysates of the synthetic HPV6a E2 transfectants; lanes c and d are negative controls. The analogous experiment is shown for HPV118 E2 expression in FIG. 16. Lanes c and d are the cell lysates of transfections receiving the synthetic HPV18 E2 gene; lanes a and b are the negative controls. Both of these figures show measurable levels of E2 product accumulation when the codon-optimized, synthetic gene is expressed in mammalian cells.

These results indicate that the synthetic gene rebuilding is not limited to HPV16 genes. Rather, codon optimization of other HPV types also permits significant levels of E7 and E2 product accumulation in mammalian cells.

Example 7

Construction of Replication-Defective FG-Ad Expressing HPV Antigen

Starting Vectors

Shuttle vector pHCMVIBGHpA1 contains Ad5 sequences from bp1 to bp 341 and bp 3534 to bp 5798 with a expression cassette containing human cytomegalovirus (HCMV) promoter plus intron A and bovine growth hormone polyadenylation signal.

The adenoviral backbone vector pAdE1-E3- (also named as pHVad1) contains all Ad5 sequences except those nucleotides encompassing the E1 and E3 region.

Construction of Ad5. HPV16 E2

1. Construction of adenoviral shuttle plasmid pA1-CMVI-HPV16 E2 containing HPV16 E2 under the control of human CMV promoter and intron A.

The HPV16 E2 insert was excised from pV1JnS—HPV16 E2 by restriction enzyme Bgl II, EcoRI and then cloned into Bgl II, EcoRI digested shuttle vector pHCMVIBGHpA1.

2. Homologous recombination to generate plasmid form of recombinant adenoviral vector pAd-CMVI-HPV16 E2 containing HPV16 E2 expression cassette.

Shuttle plasmid pA1-CMVI-HPV16 E2 was digested with restriction enzymes BstZ17 and SgrA1 and then co-transformed into E. coli strain BJ5183 with linearized (ClaI digested) adenoviral backbone plasmid pAdE1-E3-. A colony was verified by PCR analysis. The vector was transformed to competent E. coli HB101 for large quantity production of the plasmid.

3. Generation of recombinant adenovirus Ad.CMVI-HPV16 E2 in 293 cells.

The pAd plasmid was linearized by restriction enzyme PacI and transfected to 293 cells using $CaPO_4$ method (Invitrogen kit). Ten days later, 10 plaques were picked and grown in 293 cells in 35-mm plates. PCR analysis of the adenoviral DNA showed virus were positive for HPV16 E2.

4. Evaluation of large scale recombinant adenovirus Ad.C-MVI-HPV16 E2

A selected clone was grown into large quantities through multiple rounds of amplification in 293 cells. Expression of HPV16 E2 was also verified by ELISA and Western blot analysis of the 293 or COS cells infected with the recombinant adenovirus. The recombinant adenovirus was used for evaluation in mice and rhesus monkeys.

Method of Treatment

A person in need of therapeutic or prophylactic immunization against infection with human papillomavirus virus is injected with HPV DNA encoding all or part of; HPV L1, E1, E2, E4 or E7 and combinations thereof. The injection may be i.p., subcutaneous, intramuscular or intradermal. The HPV DNA may be used as a primer of the immune response or may be used as a booster of the immune response. The injection of DNA may antedate, coincide or follow injection of the person with a pharmaceutical composition comprising HPV virus like particles (containing only L1 protein or containing both L1 and L2 proteins, or containing mutant forms of one or more proteins), capsomeres, inactivated HPV, attenuated HPV, compositions comprising HPV-derived proteins, or combinations thereof.

Example 8

The Use of a Synthetically-Expressed HPV E Protein as a Model Tumor Antigen

Generation of a Tumor Cell Line that Expresses HPV 16 E2.

A Not I-Hind III restriction digest fragment containing the synthetic coding sequence for HPV 16 E2 (see above) was ligated with Not I, Hind III digested expression vector pBJ/neo/CCR2B which has a neomycin resistance marker and drives the expression of the transgene with the HCMV immediate early promoter. The resultant plasmid, pBJ-16 E2, was characterized by restriction digestion, sequence analysis of the cloning junctions, and the ability to induce E2 protein expression in transiently-transfected A293 or CT26 cells. A stable cell line was generated transfection of CT26 cells using Lipofectamine (Gibco BRL). CT26 cells, a fully-transformed line derived from a BALB/c mouse colon carcinoma, have been widely used to present model tumor antigens. (Brattain et al., 1980 Cancer Research 40:2142–2146; Fearon, E. et al., 1988 Cancer Research, 48:2975–2980; both of which are incorporated by reference).

After 48 hours, cells were trypsinized, diluted 1:10, 1:100, 1:1000 or 1:10000 into medium and plated in 100 mm$^2$ plates. After 24 hours, the medium was replaced with selection medium containing 400 µg/mL G418. After two to three weeks, well-isolated colonies of cells were recovered using cloning rings and transferred to 48-well plates. One clone was positive for E2 expression by immunoblot analysis and was subjected to two further rounds of cloning by limiting dilution. One G418 resistant, E2-positive clonal isolate was used to established the cell line JCL-031. (FIG. 25).

When inoculated into (syngeneic) BALB/c mice by subcutaneous injection, JCL-031 cell induced tumors with the kinetics similar to those as the parental CT26 line. Cells cultured from recovered tumors were G418 resistant and expressed E2.

Induction of Immunity in Mice by Immunization with V1Jns:E2 DNA.

BALB/c mice were immunized multiple times by intramuscular injection with the DNA V1Jns: 16E2. Spleens from two randomly-chosen mice in each dose group were pooled, splenocytes prepared, and assayed in an murine interferon gamma Elispot assay. (Lalvani et al. 1997 J. Exp. Med. 186: 859–865; Forsthuber, T., et al 1996 Science 271: 1728–1730;. Chu, R. et al. 1997. J. Exp. Med. 186: 1623–1631, each of which is incorporated by reference.) Splenocyte cultures were incubated at 37° C. for 24 hr. in the presence of a pool of 36 overlapping 20 amino acid residue peptides (final concentration, 4 µg/mL each) scanning the full length of HPV 16 E2. Interferon gamma was captured on the substrate by monoclonal antibody (mAb) R4-6A2 (Pharmagin), and detected with biotinylated mAb XMG1.2 (Pharmagin) and a strepavidin-alkaline phosphatase conjugate (Pharmagin). Results are shown in Table A, below. The immunized mice developed CD4$^+$ immune responses to HPV (Table A, below).

Immunization with E2 DNA did not induce detectable anti-E2 antibody responses.

TABLE A

| Dose Group | Immunization | E2-specific spots (per 10$^6$ cells) |
|---|---|---|
| 1 | E2 DNA 1 | 392 |
| 2 | E2 DNA 2 | 96 |
| 3 | E2 DNA 3 | 134 |
| 4 | Control DNA 1 | 0 |
| 5 | Control DNA 2 | 2 |

Protection from Challenge with JCL-031 Cells.

BALB/c mice, immunized with V1Jns:E2 DNA, or control DNA, were challenged by subcutaneous injection of 5×10$^5$ JCL-031 cells into the left inguinal region. Tumor growth was monitored by palpation or caliper measurement for a four-week period. FIG. 26 reports the fraction of each dose group that remained tumor free. The group that had been immunized with an E2-expressing plasmid was significantly protected from tumor development compared to the control group.

What is claimed is:

1. A method for inducing immune responses to HPV16 in a human subject which comprises administering to the subject a composition comprising between 1 ng and 100 mg of a plasmid vaccine vector and a pharmaceutically acceptable carrier, said plasmid vaccine vector comprising a synthetic polynucleotide, the synthetic polynucleotide comprising a sequence encoding a codon-optimized human papillomavirus serotype 16 (HPV16) protein, wherein said polynucleotide sequence comprises codons that are optimized for high-level expression in a human host.

2. A method for inducing immune responses to HPV16 in a human subject which comprises administering to the subject between $10^{11}$–$10^{12}$ particles of an adenoviral vector carrying a synthetic polynucleotide, the synthetic polynucleotide comprising a sequence encoding a codon-optimized human papillomavirus serotype 16 (HPV 16) protein, wherein said polynucleotide sequence comprises codons that are optimized for high-level expression in a human host.

3. A method for inducing an immune response against human papillomavirus type 16 (HPV16) in a human subject, comprising
   a) administering to the subject a first vector comprising a polynucleotide encoding a codon-optimized HPV16 protein selected from the group consisting of L1, E1, E2, and E7 proteins, wherein said polynucleotide is codon-optimized for expression in a human host cell;
   b) allowing a predetermined amount of time to pass; and
   c) administering to said subject a second vector comprising adenoviral vaccine vector comprising an adenoviral genome with a deletion in the E1 region, and an insert in the E1 region, wherein the insert comprises an expression cassette comprises i) a polynucleotide encoding a codon-optimized HPV 16 protein selected from the group consisting of L1, E1, E2, and E7 proteins, wherein said polynucleotide is codon-optimized for expression in a human host cell; and ii) a promoter operably linked to the polynucleotide.

4. A method for inducing immune responses to HPV16 in a human subject comprising a) administering to the subject a plasmid vaccine, wherein the plasmid vaccine comprises a plasmid portion and an expression cassette portion, the expression cassette portion comprising:

i) a polynucleotide encoding a codon-optimized HPV16 protein selected from the group consisting of L1, E1, E2, and E7 proteins, wherein said polynucleotide is codon-optimized for expression in a human host cell; and ii) a promoter operably linked to the polynucleotide;

b) allowing a predetermined amount of time to pass; and c) administering to said subject an adenoviral vaccine vector comprising an adenoviral genome with a deletion in the E1 region, and an insert in the E1 region, wherein the insert comprises an expression cassette comprising:

i) a polynucleotide encoding a codon-optimized HPV16 protein selected from the group consisting of L1, E1, E2, and E7 proteins, wherein said polynucleotide is codon-optimized for expression in a human host cell; and ii) a promoter operably linked to the polynucleotide.

* * * * *